US009970030B2

(12) United States Patent
Cameron et al.

(10) Patent No.: US 9,970,030 B2
(45) Date of Patent: May 15, 2018

(54) METHODS FOR INCREASING CAS9-MEDIATED ENGINEERING EFFICIENCY

(71) Applicant: Caribou Biosciences, Inc., Berkeley, CA (US)

(72) Inventors: Peter Sean Cameron, San Francisco, CA (US); Rachel E. Haurwitz, Kensington, CA (US); Andrew P. May, San Francisco, CA (US); Christopher H. Nye, San Jose, CA (US); Megan van Overbeek, Oakland, CA (US)

(73) Assignee: Caribou Biosciences, Inc., Berkeley, CA (US)

( * ) Notice: Subject to any disclaimer, the term of this patent is extended or adjusted under 35 U.S.C. 154(b) by 0 days. days.

(21) Appl. No.: 14/836,753

(22) Filed: Aug. 26, 2015

(65) Prior Publication Data

US 2016/0257973 A1 Sep. 8, 2016

Related U.S. Application Data

(60) Provisional application No. 62/042,358, filed on Aug. 27, 2014, provisional application No. 62/047,495, filed on Sep. 8, 2014.

(51) Int. Cl.
| | |
|---|---|
| *C12N 15/63* | (2006.01) |
| *C12N 9/22* | (2006.01) |
| *C07H 21/04* | (2006.01) |
| *C12N 15/90* | (2006.01) |
| *C12N 15/11* | (2006.01) |
| *C12N 15/10* | (2006.01) |
| *A01K 67/00* | (2006.01) |

(52) U.S. Cl.
CPC ............. *C12N 15/907* (2013.01); *C12N 9/22* (2013.01); *C12N 15/102* (2013.01); *C12N 15/111* (2013.01); *C12Y 301/30* (2013.01); *C12N 2310/10* (2013.01); *C12N 2310/20* (2017.05)

(58) Field of Classification Search
CPC .. C12N 15/907; C12N 15/111; C12N 15/102; C12N 9/22; C12N 2310/10; C12N 2310/20; C12Y 301/30
See application file for complete search history.

(56) References Cited

U.S. PATENT DOCUMENTS

| | | |
|---|---|---|
| 8,697,359 B1 | 4/2014 | Zhang |
| 8,795,965 B2 | 5/2014 | Zhang |
| 8,771,945 B1 | 7/2014 | Zhang |
| 8,841,260 B2 | 9/2014 | Miller et al. |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Cong et al. |
| 8,932,814 B2 | 1/2015 | Zhang et al. |
| 8,945,839 B2 | 2/2015 | Zhang |
| 8,993,233 B2 | 3/2015 | Zhang et al. |
| 8,999,641 B2 | 5/2015 | Zhang et al. |
| 9,115,348 B2 | 8/2015 | Haurwitz et al. |
| 2011/0223638 A1 | 9/2011 | Wiedenheft et al. |
| 2014/0068797 A1 | 3/2014 | Doudna et al. |
| 2014/0080216 A1 | 3/2014 | Cost et al. |
| 2014/0090116 A1 | 3/2014 | Ainley et al. |
| 2014/0093913 A1 | 4/2014 | Cost et al. |
| 2014/0178561 A1 | 6/2014 | Mathis et al. |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0189896 A1 | 7/2014 | Zhang et al. |
| 2014/0242664 A1 | 8/2014 | Zhang et al. |
| 2014/0242699 A1 | 8/2014 | Zhang |
| 2014/0248702 A1 | 9/2014 | Cong et al. |
| 2014/0287938 A1 | 9/2014 | Zhang et al. |
| 2014/0288411 A1 | 9/2014 | Shapiro et al. |
| 2014/0288421 A1 | 9/2014 | Shapiro et al. |
| 2014/0294773 A1 | 10/2014 | Brouns et al. |
| 2014/0301990 A1 | 10/2014 | Gregory et al. |
| 2014/0302563 A1 | 10/2014 | Doudna et al. |
| 2014/0310830 A1 | 10/2014 | Zhang et al. |
| 2014/0315985 A1 | 10/2014 | May et al. |
| 2014/0336133 A1 | 11/2014 | Miller et al. |
| 2014/0349405 A1 | 11/2014 | Sontheimer et al. |

(Continued)

FOREIGN PATENT DOCUMENTS

| | | |
|---|---|---|
| WO | WO 2013141680 A1 | 9/2013 |
| WO | WO 2013142578 A1 | 9/2013 |
| WO | WO 2014/065596 A1 | 5/2014 |
| WO | WO 2014/093622 A2 | 6/2014 |
| WO | WO 2014150624 A1 | 9/2014 |
| WO | WO 2014/165825 | 10/2014 |
| WO | WO 2014/191518 | 12/2014 |
| WO | WO 2014/197568 | 12/2014 |
| WO | WO 2015071474 A2 | 5/2015 |

OTHER PUBLICATIONS

Fu et al. High-frequency off-target mutagenesis induced by CRISPR-Cas nucleases in human cells. Nat. Biotechnol. 31:822-827, 2013.*
Chen et al. Dynamic imaging of genomic loci in living human cells by an optimized CRISPR/Cas system. Cell 155:1479-1491, 2013.*
Wu et al. Genome-wide binding of the CRISPR endonuclease Cas9 in mammalian cells. Nat. Biotechnol. 32:670-675, 2014.*
Kuscu et al. Genome-wide analysis reveals characteristics of off-target sites bound by the Cas9 endonuclease. Nat. Biotechnol. 32:677-685, 2014.*

(Continued)

*Primary Examiner* — Quang Nguyen
(74) *Attorney, Agent, or Firm* — Gary R. Fabian; Barbara G. McClung

(57) ABSTRACT

Methods for use with Type II CRISPR-Cas9 systems for increasing Cas9-mediated genome engineering efficiency are disclosed. The methods can be used to decrease the number of off-target nucleic acid double-stranded breaks and/or to enhance homology-directed repair of a cleaved target nucleic acid.

19 Claims, 13 Drawing Sheets

(56) References Cited

U.S. PATENT DOCUMENTS

| | | |
|---|---|---|
| 2014/0356956 A1 | 12/2014 | Church et al. |
| 2014/0357530 A1 | 12/2014 | Zhang et al. |
| 2015/0011007 A1 | 1/2015 | Liu et al. |
| 2015/0020223 A1 | 1/2015 | Zhang et al. |
| 2015/0024499 A1 | 1/2015 | Brouns et al. |
| 2015/0031134 A1 | 1/2015 | Zhang et al. |
| 2015/0056705 A1 | 2/2015 | Conway et al. |
| 2015/0064789 A1 | 3/2015 | Paschon et al. |
| 2015/0072893 A1 | 3/2015 | Kampmann et al. |
| 2015/0073041 A1 | 3/2015 | Saltzman et al. |
| 2015/0079681 A1 | 3/2015 | Zhang |
| 2015/0086581 A1 | 3/2015 | Li et al. |
| 2015/0089681 A1 | 3/2015 | Van Der Oost et al. |
| 2015/0152398 A1 | 6/2015 | Doudna et al. |
| 2015/0159172 A1 | 6/2015 | Miller et al. |
| 2015/0184139 A1 | 7/2015 | Zhang et al. |
| 2015/0190427 A1 | 7/2015 | Hui et al. |
| 2015/0191744 A1 | 7/2015 | Wolfe et al. |
| 2015/0203872 A1 | 7/2015 | Zhang |
| 2015/0218253 A1 | 8/2015 | Liu et al. |
| 2015/0218573 A1 | 8/2015 | Loque et al. |
| 2015/0232882 A1 | 8/2015 | Zhang et al. |
| 2015/0232883 A1 | 8/2015 | Dahlman et al. |
| 2015/0247150 A1 | 9/2015 | Zhang et al. |
| 2015/0267205 A1 | 9/2015 | Froelich et al. |
| 2015/0284697 A1 | 10/2015 | Haurwitz et al. |
| 2015/0291965 A1 | 10/2015 | Zhang et al. |
| 2015/0291966 A1 | 10/2015 | Zhang et al. |
| 2015/0291967 A1 | 10/2015 | Mathis et al. |
| 2015/0306250 A1 | 10/2015 | Laterza et al. |
| 2015/0335708 A1 | 11/2015 | Froelich et al. |

OTHER PUBLICATIONS

Anders C., et al., "Structural basis of PAM-dependent target DNA recognition by the Cas9 endonuclease." Nature Sep. 25, 2014;513(7519):569-73. doi: 10.1038/nature13579. Epub Jul. 27, 2014.

Barrangou, R., et al., "CRISPR provides acquired resistance against viruses in prokaryotes," Science (2007) 315:1709-1712.

Cong, L., et al., "Multiplex genome engineering using CRISPR/Cas systems," Science (2013) 339:819-823.

Deltcheva, E., et al., "CRISPR RNA maturation by trans-encoded small RNA and host factor RNase III," Nature (2011) 471:602-607.

Garneau, J. E., et al., "The CRISPR/Cas bacterial immune system cleaves bacteriophage and plasmid DNA," Nature (2010) 468:67-71.

Gasiunas, G., et al., "Cas9-crRNA ribonucleoprotein complex mediates specific DNA cleavage for adaptive immunity in bacteria," Proc Natl Acad Sci USA (2012) 109: E2579-E2586.

Guilinger, J. P., et al., "Fusion of catalytically inactive Cas9 to FokI nuclease improves the specificity of genome modification," Nature Biotechnol. (2014) 32:577-583.

Jiang, W., et al., "RNA-guided editing of bacterial genomes using CRISPR-Cas systems," Nat. Biotechnol. (2013) 31: 233-239.

Jinek M., et al., "Structures of Cas9 endonucleases reveal RNA-mediated conformational activation." Science. Mar. 14, 2014;343(6176):1247997. doi: 10.1126/science.1247997. Epub Feb. 6, 2014.

Jinek, M., et al., "A programmable dual-RNA-guided DNA endonuclease in adaptive bacterial immunity," Science (2012) 337:816-821.

Makarova, K. S., et al., "Evolution and classification of the CRISPR-Cas systems," Nat Rev Microbiol (2011) 9:467-477.

Qi, L. S., et al., "Repurposing CRISPR as an RNA-Guided Platform for Sequence-Specific Control of Gene Expression," Cell (2013) 152, 1173-1183.

Sander, J. D. & Joung, J. K., "CRISPR-Cas systems for editing, regulating and targeting genomes," Nature Biotechnol. (2014) 32:347-355.

Sapranauskas, R., et al., "The *Streptococcus thermophilus* CRISPR/Cas system provides immunity in *Escherichia coli*," Nucleic Acids Res (2011) 39: 9275-9282).

Sternberg, S. H., et al., "DNA interrogation by the CRISPR RNA-guided endonuclease Cas9," Nature (2014) 507:62.

Tsai, S. Q., et al., "Dimeric CRISPR RNA-guided FokI nucleases for highly specific genome editing," Nature Biotechnol. (2014) 32:569-576.

Great Britain Patents Act 1977: Search Report under Section 17 for Application No. GB1703026.3, dated Mar. 30, 2017, which corresponds to the present U.S. Appl. No. 14/836,753.

\* cited by examiner

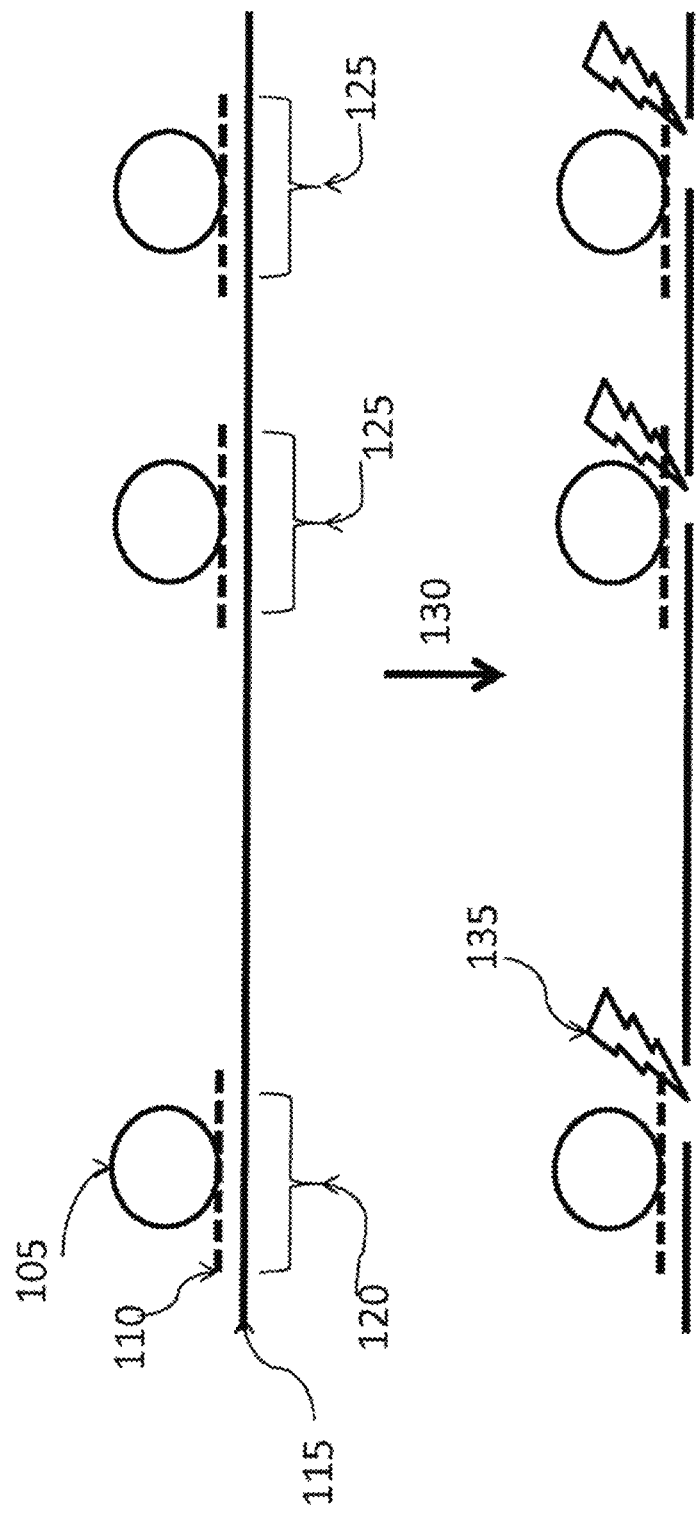

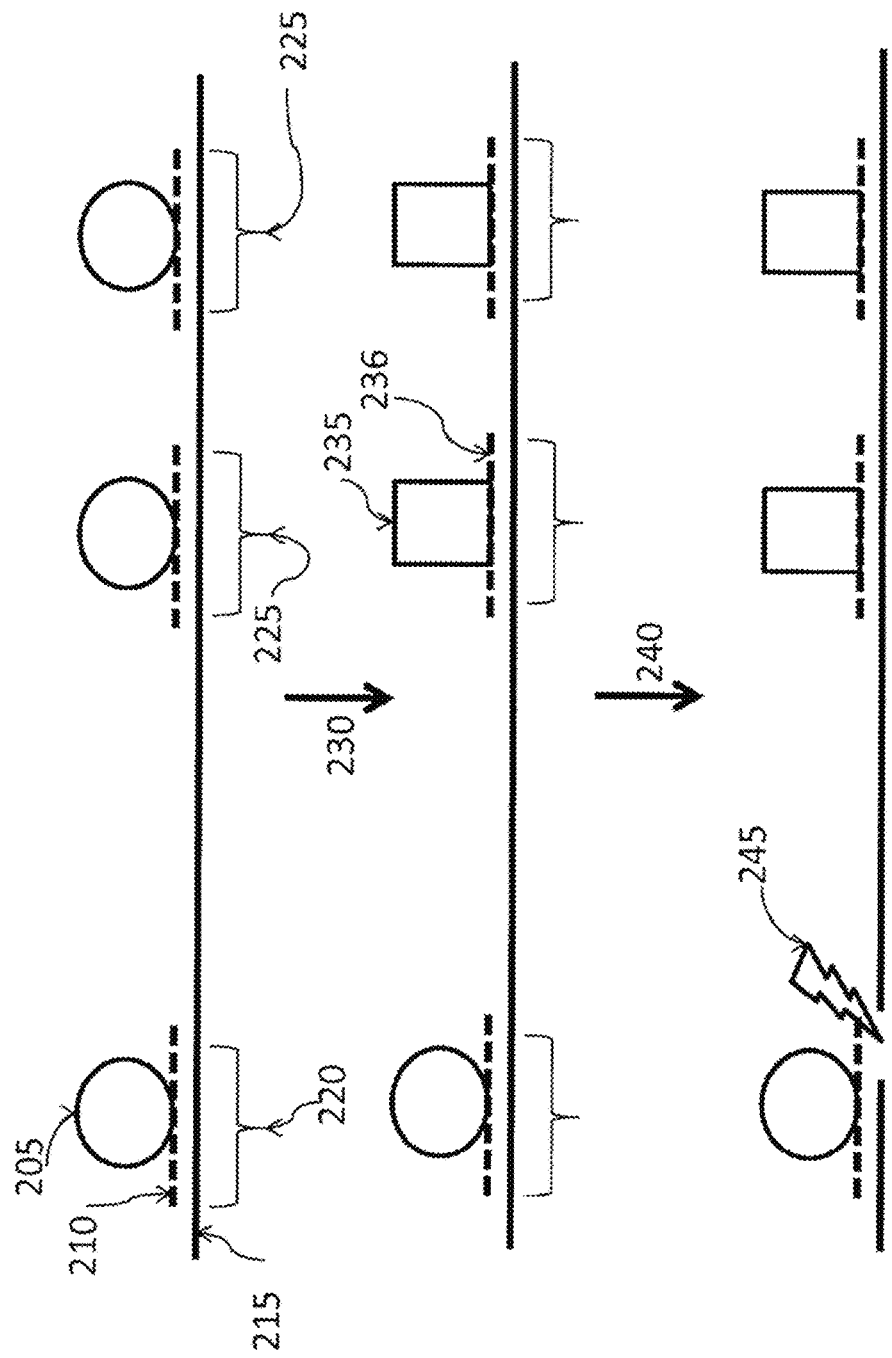

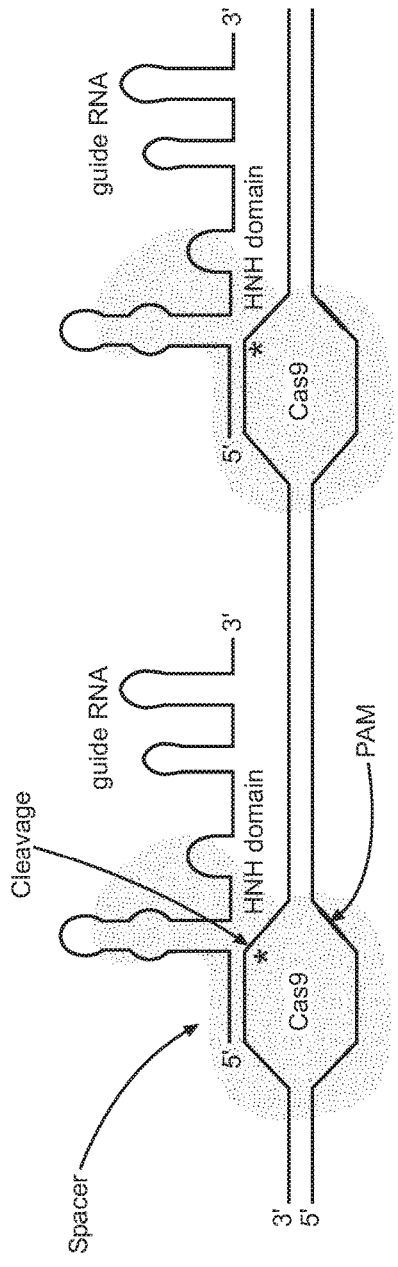
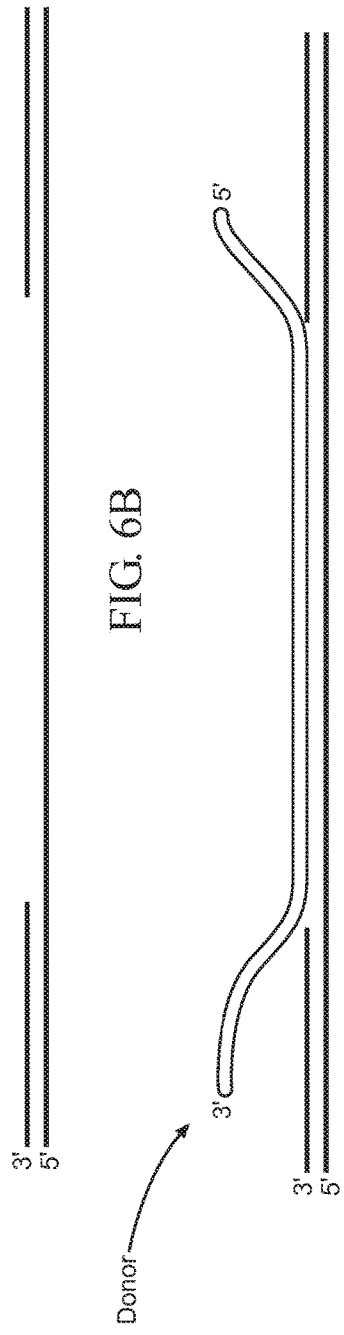
FIG. 6A
FIG. 6B
FIG. 6C

SEQUENCE LISTING

```
<160> NUMBER OF SEQ ID NOS: 84

<210> SEQ ID NO 1
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 1
aaaaaaagca ccgactcggt gcc                                            23

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 2
agtaataata cgactcacta tag                                            23

<210> SEQ ID NO 3
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 3
gttttagagc tagaaatagc aagttaaaat aaggctagtc cgttatcaac                50

<210> SEQ ID NO 4
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 4
aaaaaaagca ccgactcggt gccactttt caagttgata acggactagc                 50

<210> SEQ ID NO 5
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 5
taatacgact cactataggg tgggggagt tgctccgtt ttagagctag aaatagc          57

<210> SEQ ID NO 6
<211> LENGTH: 57
<212> TYPE: DNA
<213> ORGANISM: Artificial Sequence
```

```
<220> FEATURE:
<223> OTHER INFORMATION: Synthetic oligonucleotide

<400> SEQUENCE: 6
taatacgact cactataggg gccactaggg acaggatgtt ttagagctag aaatagc      57

<210> SEQ ID NO 7
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 7
taatacgact cactatagtg gagggagttt gctcctggtt ttagagctag aaatagc      57

<210> SEQ ID NO 8
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 8
taatacgact cactatagga cggatttgtg ggatggagtt ttagagctag aaatagc      57

<210> SEQ ID NO 9
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 9
taatacgact cactatagca ggacattctg acaccccgtt ttagagctag aaatagc      57

<210> SEQ ID NO 10
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 10
taatacgact cactatagga ggctcccatc acgggggtt ttagagctag aaatagc       57

<210> SEQ ID NO 11
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 11
taatacgact cactatagtg gggatcacag gttccccgtt ttagagctag aaatagc      57

<210> SEQ ID NO 12
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 12
taatacgact cactatagag agctcttctg actacaggtt ttagagctag aaatagc      57
```

<210> SEQ ID NO 13
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 13
taatacgact cactatagga ccaaatgaga ccagtccgtt ttagagctag aaatagc     57

<210> SEQ ID NO 14
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 14
taatacgact cactatagcc cattatgata gggaggggtt ttagagctag aaatagc     57

<210> SEQ ID NO 15
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 15
taatacgact cactatagct cctggggatg gaagggcgtt ttagagctag aaatagc     57

<210> SEQ ID NO 16
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 16
cactctttcc ctacacgacg ctcttccgat ctccagatgg cacattgtca ga          52

<210> SEQ ID NO 17
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 17
ggagttcaga cgtgtgctct tccgatctcc tagtgactgc cgtctgc                47

<210> SEQ ID NO 18
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 18
ggagttcaga cgtgtgctct tccgatctac ctggccatca tccttcta               48

<210> SEQ ID NO 19
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 19
cactctttcc ctacacgacg ctcttccgat ctcagcagac ccactgagtc aa    52

<210> SEQ ID NO 20
<211> LENGTH: 57
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (25)..(32)
<223> OTHER INFORMATION: n is a, c, g, or t

<400> SEQUENCE: 20
caagcagaag acggcatacg agatnnnnnn nngtgactgg agttcagacg tgtgctc    57

<210> SEQ ID NO 21
<211> LENGTH: 58
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (30)..(37)
<223> OTHER INFORMATION: n is a, c, g, or t

<400> SEQUENCE: 21
aatgatacgg cgaccaccga gatctacacn nnnnnnnaca ctctttccct acacgacg    58

<210> SEQ ID NO 22
<211> LENGTH: 103
<212> TYPE: RNA
<213> ORGANISM: Artificial Sequence
<220> FEATURE:
<223> OTHER INFORMATION: Synthetic oligonucleotide

<400> SEQUENCE: 22 ggguggggg aguuugcucc guuuuagagc uagaaauagc aaguuaaaau aaggcuaguc    60
cguuaucaac uugaaaaagu ggcaccgagu cggugcuuuu uuu    103

<210> SEQ ID NO 23
<211> LENGTH: 103
<212> TYPE: RNA
<213> ORGANISM: Artificial Sequence
<220> FEATURE:
<223> OTHER INFORMATION: Synthetic oligonucleotide

<400> SEQUENCE: 23
ggggccacua gggacaggau guuuuagagc uagaaauagc aaguuaaaau aaggcuaguc    60
cguuaucaac uugaaaaagu ggcaccgagu cggugcuuuu uuu    103

<210> SEQ ID NO 24
<211> LENGTH: 103
<212> TYPE: RNA
<213> ORGANISM: Artificial Sequence
<220> FEATURE:
<223> OTHER INFORMATION: Synthetic oligonucleotide

<400> SEQUENCE: 24
guggagggag uuugcuccug guuuuagagc uagaaauagc aaguuaaaau aaggcuaguc    60
cguuaucaac uugaaaaagu ggcaccgagu cggugcuuuu uuu    103

<210> SEQ ID NO 25
<211> LENGTH: 103
<212> TYPE: RNA
<213> ORGANISM: Artificial Sequence
<220> FEATURE:
<223> OTHER INFORMATION: Synthetic oligonucleotide

<400> SEQUENCE: 25
ggacggauuu gugggaugga guuuuagagc uagaaauagc aaguuaaaau aaggcuaguc    60
cguuaucaac uugaaaaagu ggcaccgagu cggugcuuuu uuu                     103

<210> SEQ ID NO 26
<211> LENGTH: 104
<212> TYPE: RNA
<213> ORGANISM: Artificial Sequence
<220> FEATURE:
<223> OTHER INFORMATION: Synthetic oligonucleotide

<400> SEQUENCE: 26
gcaggacauu cugacacccc guuuuagagc uagaaauagc aaguuaaaau aaggcuaguc    60
cguuaucaac uugaaaaagu ggcaccgagu cggugcuuuu uuuu                    104

<210> SEQ ID NO 27
<211> LENGTH: 103
<212> TYPE: RNA
<213> ORGANISM: Artificial Sequence
<220> FEATURE:
<223> OTHER INFORMATION: Synthetic oligonucleotide

<400> SEQUENCE: 27
ggaggcuccc aucacggggg guuuuagagc uagaaauagc aaguuaaaau aaggcuaguc    60
cguuaucaac uugaaaaagu ggcaccgagu cggugcuuuu uuu                     103

<210> SEQ ID NO 28
<211> LENGTH: 103
<212> TYPE: RNA
<213> ORGANISM: Artificial Sequence
<220> FEATURE:
<223> OTHER INFORMATION: Synthetic oligonucleotide

<400> SEQUENCE: 28
guggggauca cagguucccc guuuuagagc uagaaauagc aaguuaaaau aaggcuaguc    60
cguuaucaac uugaaaaagu ggcaccgagu cggugcuuuu uuu                     103

<210> SEQ ID NO 29
<211> LENGTH: 103
<212> TYPE: RNA
<213> ORGANISM: Artificial Sequence
<220> FEATURE:
<223> OTHER INFORMATION: Synthetic oligonucleotide

<400> SEQUENCE: 29
gagagcucuu cugacuacag guuuuagagc uagaaauagc aaguuaaaau aaggcuaguc    60
cguuaucaac uugaaaaagu ggcaccgagu cggugcuuuu uuu                     103

<210> SEQ ID NO 30
<211> LENGTH: 103
<212> TYPE: RNA
<213> ORGANISM: Artificial Sequence
<220> FEATURE:
<223> OTHER INFORMATION: Synthetic oligonucleotide

<400> SEQUENCE: 30
ggaccaaaug agaccagucc guuuuagagc uagaaauagc aaguuaaaau aaggcuaguc    60
cguuaucaac uugaaaaagu ggcaccgagu cggugcuuuu uuu                     103

<210> SEQ ID NO 31
<211> LENGTH: 103
<212> TYPE: RNA
<213> ORGANISM: Artificial Sequence
<220> FEATURE:
<223> OTHER INFORMATION: Synthetic oligonucleotide

<400> SEQUENCE: 31
gcccauuaug auagggaggg guuuuagagc uagaaauagc aaguuaaaau aaggcuaguc    60
cguuaucaac uugaaaaagu ggcaccgagu cggugcuuuu uuu                     103

<210> SEQ ID NO 32
<211> LENGTH: 104
<212> TYPE: RNA
<213> ORGANISM: Artificial Sequence
<220> FEATURE:
<223> OTHER INFORMATION: Synthetic oligonucleotide

<400> SEQUENCE: 32
gcuccugggg auuggaaggg cguuuuagag cuagaaauag caaguuaaaa uaaggcuagu    60
ccguuaucaa cuugaaaaag uggcaccgag ucggugcuuu uuuu                    104

<210> SEQ ID NO 33
<211> LENGTH: 8
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(8)
<223> OTHER INFORMATION: n is a, c, g, or t

<400> SEQUENCE: 33 nnnnnnnn                                                            8

<210> SEQ ID NO 34
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 34
taatacgact cactatagga acactgtgct gattacaggt tttagagcta gaaatagc     58

<210> SEQ ID NO 35
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 35
taatacgact cactataggt ttgtgtttcc ataaactggt tttagagcta gaaatagc     58

<210> SEQ ID NO 36
<211> LENGTH: 58
<212> TYPE: DNA
<213> ORGANISM: Artificial Sequence
<220> FEATURE:

<223> OTHER INFORMATION: Synthetic oligonucleotide

<400> SEQUENCE: 36
taatacgact cactataggc tactaacttg agctccccgt tttagagcta gaaatagc    58

<210> SEQ ID NO 37
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 37
taatacgact cactatagtc ccaaaggcgg agggcgttgt tttagagcta gaaatagc    58

<210> SEQ ID NO 38
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 38
taatacgact cactatagag gctgggttgc cgccgtcggt tttagagcta gaaatagc    58

<210> SEQ ID NO 39
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 39
tcagtttatg gaaacacaaa ctcttctgtc cagtcacaga gaattcctgt aatcagcaca    60
gtgttcacca ccccagccaa cgtttcaact    90

<210> SEQ ID NO 40
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 40
ccagaaacga cagtcaaatt cacatctacc tctgtgataa gaattccagt ttatggaaac    60
acaaactctt ctgtccagtc acagacctct    90

<210> SEQ ID NO 41
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 41
acccagcctc cctcctaacg ccctccgcct ttgggaccaa gaattcgggg agctcaagtt    60
agtagcagcc aaggagaggc gctgccttgc    90

<210> SEQ ID NO 42
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 42 ccacctttt tggcctcgac ggcggcaacc cagcctccct gaattcaacg ccctccgcct    60
ttgggaccaa ccaggggagc tcaagttagt                                    90

<210> SEQ ID NO 43
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 43
cgaggcatct ggagcccgaa caaacctcca ccttttttgg gaattccgac ggcggcaacc    60
cagcctccct cctaacgccc tccgcctttg                                    90

<210> SEQ ID NO 44
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 44
cacatctacc tctgtgataa gctcagttta tggaattcac aaactcttct gtccagtcac    60
agagctctgt aatcagcaca gtgttcacca                                    90

<210> SEQ ID NO 45
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 45
cctcgacggc ggcaacccag cctccctgct aacgccctcc gaattctggg accaagcagg    60
ggagctcaag ttagtagcag ccaaggagag                                    90

<210> SEQ ID NO 46
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 46
ccgaacaaac ctccaccttt tttggcgtcg acggcggcaa ccgaattcct ccctcgtaac    60
gccctccgcc tttgggacca accaggggag                                    90

<210> SEQ ID NO 47
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 47 ccacctttt tgggctcgac ggcggcaacc cagcctccct ccgaattcgc cctccgcctt    60
tgggaccaag caggggagct caagttagta                                    90

<210> SEQ ID NO 48

<210> SEQ ID NO 48
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 48
ggagttcaga cgtgtgctct tccgatcttg caaggctagt gctagtgg    48

<210> SEQ ID NO 49
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 49
cactctttcc ctacacgacg ctcttccgat ctacatgcac acccatgttt tg    52

<210> SEQ ID NO 50
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 50
ggagttcaga cgtgtgctct tccgatctaa catttccagg tgacaggc    48

<210> SEQ ID NO 51
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 51
cactctttcc ctacacgacg ctcttccgat ctacatgcac acccatgttt tg    52

<210> SEQ ID NO 52
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 52
ggagttcaga cgtgtgctct tccgatctgt gggggattct tgcttttt    48

<210> SEQ ID NO 53
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 53
cactctttcc ctacacgacg ctcttccgat ctctccagaa agctgaacga gg    52

<210> SEQ ID NO 54
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 54
ggagttcaga cgtgtgctct tccgatcttt tcctctcttc tcccctcc            48

<210> SEQ ID NO 55
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 55
cactctttcc ctacacgacg ctcttccgat ctctgccaca aaggggttaa aa          52

<210> SEQ ID NO 56
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 56
ggagttcaga cgtgtgctct tccgatcttt tcctctcttc tcccctcc            48

<210> SEQ ID NO 57
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 57
cactctttcc ctacacgacg ctcttccgat ctctgccaca aaggggttaa aa          52

<210> SEQ ID NO 58
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 58
ggagttcaga cgtgtgctct tccgatcttg caaggctagt gctagtgg            48

<210> SEQ ID NO 59
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 59
cactctttcc ctacacgacg ctcttccgat ctcacatgca cacccatgtt tt          52

<210> SEQ ID NO 60
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 60
ggagttcaga cgtgtgctct tccgatcttc tcttctcccc tccctttt            48

<210> SEQ ID NO 61
<211> LENGTH: 53
<212> TYPE: DNA

<213> ORGANISM: Artificial Sequence
<220> FEATURE:
<223> OTHER INFORMATION: Synthetic oligonucleotide

<400> SEQUENCE: 61
cactctttcc ctacacgacg ctcttccgat ctgccacaaa ggggttaaaa gtt       53

<210> SEQ ID NO 62
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 62
aatgatacgg cgaccaccga gatctacact gaaccttaca ctctttccct acacgacg    58

<210> SEQ ID NO 63
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 63
aatgatacgg cgaccaccga gatctacact gctaagtaca ctctttccct acacgacg    58

<210> SEQ ID NO 64
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 64
aatgatacgg cgaccaccga gatctacact aagttccaca ctctttccct acacgacg    58

<210> SEQ ID NO 65
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 65
aatgatacgg cgaccaccga gatctacaca tagaggcaca ctctttccct acacgacg    58

<210> SEQ ID NO 66
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 66
aatgatacgg cgaccaccga gatctacacg gctctgaaca ctctttccct acacgacg    58

<210> SEQ ID NO 67
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 67
aatgatacgg cgaccaccga gatctacaca ggcgaagaca ctctttccct acacgacg    58

<210> SEQ ID NO 68
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 68
aatgatacgg cgaccaccga gatctacact aatcttaaca ctctttccct acacgacg    58

<210> SEQ ID NO 69
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 69
aatgatacgg cgaccaccga gatctacacc aggacgtaca ctctttccct acacgacg    58

<210> SEQ ID NO 70
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 70
caagcagaag acggcatacg agatatacat cggtgactgg agttcagacg tgtgctc     57

<210> SEQ ID NO 71
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 71
caagcagaag acggcatacg agatatgcct aagtgactgg agttcagacg tgtgctc     57

<210> SEQ ID NO 72
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 72
caagcagaag acggcatacg agatattcaa gtgtgactgg agttcagacg tgtgctc     57

<210> SEQ ID NO 73
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 73
caagcagaag acggcatacg agatatctga tcgtgactgg agttcagacg tgtgctc     57

<210> SEQ ID NO 74
<211> LENGTH: 57
<212> TYPE: DNA
<213> ORGANISM: Artificial Sequence
<220> FEATURE:

<223> OTHER INFORMATION: Synthetic oligonucleotide

<400> SEQUENCE: 74
caagcagaag acggcatacg agatatgtag ccgtgactgg agttcagacg tgtgctc       57

<210> SEQ ID NO 75
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 75
caagcagaag acggcatacg agatatttga ctgtgactgg agttcagacg tgtgctc       57

<210> SEQ ID NO 76
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 76
caagcagaag acggcatacg agatatggaa ctgtgactgg agttcagacg tgtgctc       57

<210> SEQ ID NO 77
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 77
caagcagaag acggcatacg agatattgac atgtgactgg agttcagacg tgtgctc       57

<210> SEQ ID NO 78
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 78
caagcagaag acggcatacg agatatggac gggtgactgg agttcagacg tgtgctc       57

<210> SEQ ID NO 79
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 79
caagcagaag acggcatacg agatatccac tcgtgactgg agttcagacg tgtgctc       57

<210> SEQ ID NO 80
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 80
caagcagaag acggcatacg agatatcttt tggtgactgg agttcagacg tgtgctc       57

```
<210> SEQ ID NO 81
<211> LENGTH: 57
<212> TYPE: DNA
<213> ORGANISM: Artificial Sequence
<220> FEATURE:
<223> OTHER INFORMATION: Synthetic oligonucleotide

<400> SEQUENCE: 81
caagcagaag acggcatacg agatattgag tggtgactgg agttcagacg tgtgctc      57

<210> SEQ ID NO 82
<211> LENGTH: 23
<212> TYPE: DNA
<213> ORGANISM: Homo sapiens

<400> SEQUENCE: 82
gggtgggggg agtttgctcc tgg                                            23

<210> SEQ ID NO 83
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 83
ggatggaggg agtttgctcc tgg                                            23

<210> SEQ ID NO 84
<211> LENGTH: 23
<212> TYPE: DNA
<213> ORGANISM: Adeno-Associated Virus

<400> SEQUENCE: 84
ggggccacta gggacaggat tgg                                            23
```

METHODS FOR INCREASING CAS9-MEDIATED ENGINEERING EFFICIENCY

CROSS-REFERENCE TO RELATED APPLICATIONS

This application claims the benefit under 35 U.S.C. § 119(e)(1) of U.S. Provisional Application No. 62/042,358, filed Aug. 27, 2014 and 62/047,495, filed Sep. 8, 2014, each of which applications is incorporated herein by reference in its entirety.

TECHNICAL FIELD

The present invention relates to Type II CRISPR-Cas9 systems for use in increasing Cas9-mediated genome engineering efficiency by either decreasing the number of off-target nucleic acid double-stranded breaks, and/or enhancing homology-directed repair of a cleaved target nucleic acid.

BACKGROUND OF THE INVENTION

Clustered regularly interspaced short palindromic repeats (CRISPR) and associated Cas9 proteins constitute the CRISPR-Cas9 system. This system provides adaptive immunity against foreign DNA in bacteria (Barrangou, R., et al., "CRISPR provides acquired resistance against viruses in prokaryotes," Science (2007) 315:1709-1712; Makarova, K. S., et al., "Evolution and classification of the CRISPR-Cas systems," Nat Rev Microbiol (2011) 9:467-477; Garneau, J. E., et al., "The CRISPR/Cas bacterial immune system cleaves bacteriophage and plasmid DNA," Nature (2010) 468:67-71; Sapranauskas, R., et al., "The *Streptococcus thermophilus* CRISPR/Cas system provides immunity in *Escherichia coli*," Nucleic Acids Res (2011) 39: 9275-9282).

The RNA-guided Cas9 endonuclease specifically targets and cleaves DNA in a sequence-dependent manner (Gasiunas, G., et al., "Cas9-crRNA ribonucleoprotein complex mediates specific DNA cleavage for adaptive immunity in bacteria," Proc Natl Acad Sci USA (2012) 109: E2579-E2586; Jinek, M., et al., "A programmable dual-RNA-guided DNA endonuclease in adaptive bacterial immunity," Science (2012) 337:816-821; Sternberg, S. H., et al., "DNA interrogation by the CRISPR RNA-guided endonuclease Cas9," Nature (2014) 507:62; Deltcheva, E., et al., "CRISPR RNA maturation by trans-encoded small RNA and host factor RNase III," Nature (2011) 471:602-607), and has been widely used for programmable genome editing in a variety of organisms and model systems (Cong, L., et al., "Multiplex genome engineering using CRISPR/Cas systems," Science (2013) 339:819-823; Jiang, W., et al., "RNA-guided editing of bacterial genomes using CRISPR-Cas systems," Nat. Biotechnol. (2013) 31: 233-239; Sander, J. D. & Joung, J. K., "CRISPR-Cas systems for editing, regulating and targeting genomes," Nature Biotechnol. (2014) 32:347-355).

Jinek, M., et al., ("A programmable dual-RNA-guided DNA endonuclease in adaptive bacterial immunity," Science (2012) 337:816-21) showed that in a subset of CRISPR-associated (Cas) systems, the mature crRNA that is base-paired to trans-activating crRNA (tracrRNA) forms a two-part RNA structure, also called "dual-guide," that directs the CRISPR-associated protein Cas9 to introduce double-stranded breaks in target DNA. At sites complementary to the crRNA-guide (spacer) sequence, the Cas9 HNH nuclease domain cleaves the complementary strand and the Cas9 RuvC-like domain cleaves the non-complementary strand. Dual-crRNA/tracrRNA molecules were engineered into single-chain crRNA/tracrRNA molecules. These single-chain crRNA/tracrRNA directed target sequence-specific Cas9 double-strand DNA cleavage.

However, site-specific nucleases such as Cas9 can introduce double-stranded breaks in DNA in unintended and/or incorrect locations, termed "off-target effects." Accordingly, methods to reduce or eliminate off-target DNA breaks are highly desirable.

Additionally, DNA double-stranded breaks can be repaired by, for example, non-homologous end joining (NHEJ) or homology-directed repair (HDR). Faithful repair by HDR is inefficient at site-directed breaks of the target nucleic acid because other cellular mechanisms may result in the incorporation of nucleic acids at the site of a double-stranded break or a single-stranded nick. It is apparent there is a clear need to develop novel strategies that mitigate or eliminate off-target genome editing events and increase the efficiency of inserting new material into the sites cut by site-directed nucleases such as Cas9.

SUMMARY

In one aspect, the disclosure provides for a method for reducing off-targeting nuclease cleavage comprising: contacting a first complex comprising a catalytically active Cas9 and a guide RNA with a target nucleic acid; contacting a second complex comprising a catalytically inactive Cas9 (dCas9) and a guide RNA with an off-target nucleic acid; and cleaving the target nucleic acid with the first complex, wherein the second complex prevents the first complex from cleaving the off-target nucleic acid. In some embodiments, the active Cas9 comprises at least 25% amino acid identity to the HNH and RuvC active site motifs of a Cas9 from *Streptococcus pyogenes*, such as at least 50%, 75%, 95%, 99% and complete amino acid identity, or any percentage between 25% and 100%, to a Cas9 from *S. pyogenes*.

In some embodiments, the active Cas9 comprises at least 25% amino acid identity to the HNH and RuvC active site motifs of a Cas9 from *Streptococcus thermophilus*, such as at least 50%, 75%, 95%, 99% and complete amino acid identity, or any percentage between 25% and 100%, to a Cas9 from *S. thermophilus*. In some embodiments, the active Cas9 comprises at least 25% amino acid identity to the HNH and RuvC active site motifs of a Cas9 from *Staphylococcus aureus*, such as at least 50%, 75%, 95%, 99% and complete amino acid identity, or any percentage between 25% and 100%, to a Cas9 from *S. aureus*. In some embodiments, the active Cas9 comprises at least 25% amino acid identity to the HNH and RuvC active site motifs of a Cas9 from *Neisseria meningitidis*, such as at least 50%, 75%, 95%, 99% and complete amino acid identity, or any percentage between 25% and 100%, to a Cas9 from *N. meningitidis*.

In some embodiments, the catalytically inactive Cas9 comprises a mutation in one or both of its nuclease domains. In some embodiments, the dCas9 is at least 80% catalytically inactive compared to a wild-type Cas9.

In some embodiments, the first complex is capable of binding to the off-target nucleic acid. In some embodiments, the binding and/or cleavage of the first complex to the off-target nucleic acid is reduced by at least 30%. In some embodiments, the binding of the first complex to the off-target nucleic acid is reduced by at least 70%.

In some embodiments, the cleaving comprises introducing a double-stranded break. In some embodiments, the cleaving comprises introducing a single-stranded break. In some embodiments, the target nucleic acid is DNA. In some embodiments, the target nucleic acid is double-stranded DNA.

In another aspect, the disclosure provides for a composition comprising: two site-directed polypeptides to Cas9, wherein the two site-directed polypeptides comprise a mutation in one of their nuclease domains, wherein the two site-directed polypeptides are configured to bind and cleave the same strand of a double-stranded target nucleic acid.

In some embodiments, the two site-directed polypeptides comprise at least 10% amino acid identity to a nuclease domain of Cas9 from *S. pyogenes*.

In some embodiments, the mutation comprises a D10A mutation. In some embodiments, the mutation comprises an H840A mutation. In some embodiments, the target nucleic acid is DNA.

In some embodiments, the two site-directed polypeptides are bound to the sense strand of the double-stranded target nucleic acid. In some embodiments, the two site-directed polypeptides are bound to the anti-sense strand of the double-stranded target nucleic acid. In some embodiments, the composition further comprises a donor polynucleotide. In some embodiments, the donor polynucleotide is single-stranded. In some embodiments, the donor polynucleotide is double-stranded. In some embodiments, the donor polynucleotide is partially single-stranded and partially double-stranded.

In another embodiment, a method for reducing binding and/or cleavage of an off-target nucleic acid by a complex comprising a catalytically active Cas9 protein and a guide polynucleotide, is provided. The method comprises: (a) contacting a first complex with a selected target nucleic acid, wherein said first complex comprises: (i) a catalytically active Cas9 protein and (ii) a first guide polynucleotide, such as sgRNA, that comprises a spacer adapted to bind to said selected target nucleic acid; and (b) contacting a second complex with an off-target nucleic acid, wherein said second complex comprises (i) a catalytically inactive Cas9 protein (dCas9 protein) that does not cleave the off-target nucleic acid and (ii) a second guide polynucleotide, such as sgRNA, that comprises a spacer adapted to bind to said off-target nucleic acid, thereby reducing binding and/or cleavage by said first complex of said off-target nucleic acid.

In other embodiments, the catalytically active Cas9 protein comprises at least 75% amino acid identity to a Cas9 from *S. pyogenes*, with the proviso that the Cas9 protein retains catalytic activity. In certain embodiments, the catalytically active Cas9 protein comprises at least 95% amino acid identity to a Cas9 from *S. pyogenes*, with the proviso that the Cas9 protein retains catalytic activity. In additional embodiments of the method, the catalytically active Cas9 protein is a *S. pyogenes* Cas9 protein or an orthologous Cas9 protein.

In further embodiments, the dCas9 protein comprises at least one mutation in one or more endonuclease domains to render the dCas9 protein catalytically inactive. In some embodiments, the dCas9 protein comprises at least 75% amino acid identity to a Cas9 protein from *S. pyogenes*. In other embodiments, the dCas9 protein comprises at least 75% amino acid identity to a Cas9 protein from *S. pyogenes*. In additional embodiments, the dCas9 protein is a *S. pyogenes* Cas9 protein or an orthologous Cas9 protein with at least one mutation in one or more endonuclease domains to render the orthologous Cas9 protein catalytically inactive. In certain embodiments, the one or more mutations is in a RuvC-1 domain, such as a D10A mutation, numbered relative to *S. pyogenes* Cas9, or the corresponding mutation in an orthologous Cas9 protein. In other embodiments, the one or more mutations is in the HNH domain, such as a H840A mutation, numbered relative to *S. pyogenes* Cas9, or the corresponding mutation in an orthologous Cas9 protein. In additional embodiments, the one or more mutations comprises a D10A mutation and a H840A mutation, numbered relative to *S. pyogenes* Cas9, or the corresponding mutations in an orthologous Cas9 protein.

In additional embodiments, the selected target nucleic acid is DNA, such as double-stranded DNA.

In further embodiments, the selected target nucleic acid is cleaved to provide a cleavage site and the method further comprises modifying the target nucleic acid, such as by inserting at least a portion of the donor polynucleotide at the cleavage site. In other embodiments, the modifying comprises deleting one or more nucleotides at the cleavage cite.

In additional embodiments, the method is performed in a cell, such as a eukaryotic cell, or in vitro.

In another embodiment, a method for modifying a target nucleic acid is provided comprising: contacting two complexes to the same strand of the target nucleic acid, wherein each of the two complexes comprises a site-directed polypeptide and a nucleic acid-targeting nucleic acid, wherein the two site-directed polypeptides comprise a mutation in one of their nuclease domains; and modifying the target nucleic acid. In some embodiments, the nucleic acid-targeting nucleic acid from one of the two complexes targets a different location in the target nucleic acid than the nucleic acid-targeting nucleic acid from the other of the two complexes.

In some embodiments, the two site-directed polypeptides comprise at least 75% amino acid identity to Cas9 from *S. pyogenes*. In some embodiments, the two site-directed polypeptides comprise at least 10% amino acid identity to a nuclease domain of Cas9 from *S. pyogenes*. In some embodiments, the mutation comprises a D10A mutation. In some embodiments, the mutation comprises an H840A mutation. In some embodiments, the target nucleic acid is DNA.

In some embodiments, the two site-directed polypeptides are bound to the sense strand of the double-stranded target nucleic acid. In some embodiments, the two site-directed polypeptides are bound to the anti-sense strand of the double-stranded target nucleic acid. In some embodiments, the modifying comprises cleaving the same strand of the target nucleic acid. In some embodiments, the cleaving comprises a single-stranded break. In some embodiments, the method further comprises inserting a donor polynucleotide into the target nucleic acid. In some embodiments, the donor polynucleotide is single-stranded. In some embodiments, the donor polynucleotide is double-stranded. In some embodiments, the donor polynucleotide is partially single-stranded and partially double-stranded.

In another embodiment, the invention is directed to a method for cleaving a single strand of a target nucleic acid comprising contacting first and second complexes at spaced-apart locations on the same strand of a nucleic acid molecule. The first complex comprises (i) a first Cas9 protein with a mutation in an endonuclease domain thereof to render the Cas9 protein a nickase; and (ii) a first guide polynucleotide, such as sgRNA, that comprises a spacer adapted to bind to a first target nucleic acid. The second complex comprises (i) a second Cas9 protein with a mutation in an endonuclease domain thereof, to render the Cas9 protein a nickase; and (ii) a second guide polynucleotide, such as sgRNA, that comprises a spacer adapted to bind to a second target nucleic; wherein the first and second Cas9 proteins cleave a single strand of said nucleic acid molecule at the spaced-apart locations on the same strand, to render a single-stranded break.

In some embodiments, the first Cas9 protein and/or the second Cas9 protein comprises at least 75% amino acid identity to a Cas9 from *S. pyogenes*. In certain embodiments, the Cas9 protein comprises at least 95% amino acid identity to a Cas9 from *S. pyogenes*. In additional embodiments of the method, the first Cas9 protein and/or the second Cas9 protein is a *S. pyogenes* Cas9 protein or an orthologous Cas9 protein with a mutation in an endonuclease domain thereof, to render the orthologous Cas9 protein a nickase. In certain embodiments, the one or more mutations is in a RuvC-1 domain, such as a D10A mutation, numbered relative to *S. pyogenes* Cas9, or the corresponding mutation in an orthologous Cas9 protein. In other embodiments, the one or more mutations is in the HNH domain, such as a H840A mutation, numbered relative to *S. pyogenes* Cas9, or the corresponding mutation in an orthologous Cas9 protein.

In further embodiments, the target nucleic acid is double-stranded DNA and the complexes bind to and cleave the anti-sense strand of the double-stranded DNA. In other embodiments, the target nucleic acid is double-stranded DNA and the complexes bind to and cleave the sense strand of the double-stranded DNA.

In additional embodiments, the method further comprises modifying the target nucleic acid, such as by inserting at least a portion of the donor polynucleotide into the target nucleic acid at the single-stranded break. In certain embodiments, the donor polynucleotide is single-stranded. In further embodiments, the inserting is done using homology-directed repair of the donor polynucleotide with the target nucleic acid.

In additional embodiments, the method is performed in a cell, such as a eukaryotic cell, or in vitro.

In yet further embodiments, a method for directed homology-directed repair (HDR) in a target nucleic acid is provided. The method comprises: (a) contacting a first complex with a first target nucleic acid, wherein said first complex comprises: (i) a catalytically active Cas9 protein and (ii) a first guide polynucleotide, such as a sgRNA, that comprises a spacer adapted to bind to said first target nucleic acid, wherein said first complex cleaves the first target nucleic acid; and (b) contacting a second complex with a second target nucleic acid, wherein said second complex comprises: (i) a first catalytically inactive Cas9 protein (dCas9 protein) that comprises at least one mutation in one or more endonuclease domains to render the dCas9 protein catalytically inactive such that the dCas9 protein does not cleave the second target nucleic acid, and (ii) a second guide polynucleotide, such as sgRNA, that comprises a spacer adapted to bind to said second target nucleic acid, wherein the second complex comprises one end of a polynucleotide donor associated therewith and configured in proximity to the cleaved first target nucleic acid; wherein at least a portion of the polynucleotide donor is inserted into the first target nucleic acid via HDR.

In certain embodiments, the second target nucleic acid is upstream of the first target nucleic acid. In other embodiments, the second target nucleic acid is downstream of the first target nucleic acid.

In certain embodiments of the above method above, the 5' end of the polynucleotide donor is associated with the second, complex. In other embodiments, the 3' end of the polynucleotide donor is associated with the second complex.

In additional embodiments, the method further comprises: (c) contacting a third complex with a third target nucleic acid, wherein the third target nucleic acid is positioned downstream of the first target nucleic acid when the first target nucleic acid is downstream of the second target nucleic acid, or wherein the third target nucleic acid is positioned upstream of the first target nucleic acid when the first target nucleic acid is upstream of the second target nucleic acid, wherein said third complex comprises: (i) a second dCas9 protein that comprises at least one mutation in one or more endonuclease domains to render the second dCas9 protein catalytically inactive such that the second dCas9 protein does not cleave the third target nucleic acid, and (ii) a third guide polynucleotide, such as sgRNA, that comprises a spacer adapted to bind to said third target nucleic acid, and wherein the third complex comprises the other end of the polynucleotide donor associated with the second complex. In certain embodiments, the 5' end of the polynucleotide donor is associated with the second complex and the 3' end of the polynucleotide donor is associated with the third complex. In other embodiments, the 3' end of the polynucleotide donor is associated with the second complex and the 5' end of the polynucleotide donor is associated with the third complex.

In other embodiments, the Cas9 protein comprises at least 75% amino acid identity to a Cas9 from *S. pyogenes*, with the proviso that the Cas9 protein retains catalytic activity. In certain embodiments, the Cas9 protein comprises at least 95% amino acid identity to a Cas9 from *S. pyogenes*, with the proviso that the Cas9 protein retains catalytic activity. In additional embodiments of the method, the Cas9 protein is a *S. pyogenes* Cas9 protein or an orthologous Cas9 protein.

In further embodiments, the dCas9 protein comprises at least 75% amino acid identity to a Cas9 protein from *S. pyogenes*. In other embodiments, the dCas9 protein comprises at least 75% amino acid identity to a Cas9 protein from *S. pyogenes*. In additional embodiments, the dCas9 protein is a *S. pyogenes* Cas9 protein or an orthologous Cas9 protein with at least one mutation in one or more endonuclease domains to render the orthologous Cas9 protein catalytically inactive. In certain embodiments, the one or more mutations is in a RuvC-1 domain, such as a D10A mutation, numbered relative to *S. pyogenes* Cas9, or the corresponding mutation in an orthologous Cas9 protein. In other embodiments, the one or more mutations is in the HNH domain, such as a H840A mutation, numbered relative to *S. pyogenes* Cas9, or the corresponding mutation in an orthologous Cas9 protein. In additional embodiments, the one or more mutations comprises a D10A mutation and a H840A mutation, numbered relative to *S. pyogenes* Cas9, or the corresponding mutations in an orthologous Cas9 protein.

In additional embodiments, the selected target nucleic acid is DNA, such as double-stranded DNA.

In further embodiments, the method is performed in a cell, such as a eukaryotic cell, or in vitro.

These aspects and other embodiments of the methods for increasing Cas9-mediated engineering efficiency and/or HDR repair will readily occur to those of ordinary skill in the art in view of the disclosure herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 1A shows a two-RNA component Type II CRISPR-Cas9 comprising a crRNA (FIG. 1A, 101) and a tracrRNA (FIG. 1A, 102), otherwise known as a dual-guide RNA. FIG. 1B illustrates the formation of base-pair hydrogen bonds between the crRNA and the tracrRNA to form secondary structure (see U.S. Published Patent Application No. 2014-0068797, published 6 Mar. 2014; see also Jinek M., et al., "A programmable dual-RNA-guided DNA endonuclease in adaptive bacterial immunity," Science (2012) 337:816-821). The figures present an overview of and nomenclature for secondary structural elements of the crRNA and tracrRNA of the *S. pyogenes* Cas9 including the following: a spacer element (FIG. 1B, 103); a first stem element comprising a lower stem element (FIG. 1B, 104), a bulge element comprising unpaired nucleotides (FIG. 1B, 105), and an upper stem element (FIG. 1B, 106); a nexus element (FIG. 1B, 107); a second hairpin element comprising a second stem element (FIG. 1B, 108); and a third hairpin element comprising a third stem element (FIG. 1B, 109). The figures are not proportionally rendered nor are they to scale. The locations of indicators are approximate.

FIG. 3A provides a model based on the crystal structure of *S. pyogenes* Cas9 (SpyCas9) in an active complex with sgRNA (Anders C., et al., "Structural basis of PAM-dependent target DNA recognition by the Cas9 endonuclease," Nature (2014) 513:569-573). Structural studies of the SpyCas9 showed that the protein exhibits a bi-lobed architecture comprising the Catalytic nuclease lobe and the α-Helical lobe of the enzyme (See Jinek M., et al., "Structures of Cas9 endonucleases reveal RNA-mediated conformational activation," Science (2014) 343:1247997; Anders C., et al., "Structural basis of PAM-dependent target DNA recognition by the Cas9 endonuclease," Nature (2014) 513: 569-573). In FIG. 3A, the α-Helical lobe (FIG. 3A, Helical domain) is shown as the darker lobe; the Catalytic nuclease lobe (FIG. 3A, Catalytic nuclease lobe) is shown in a light grey and the sgRNA backbone is shown in black (FIG. 3A, sgRNA). The relative location of the 3' end of the sgRNA is indicated (FIG. 3A, 3' end sgRNA). The spacer RNA of the sgRNA is not visible because it is surrounded by the two protein lobes. The relative location of the 5' end of the sgRNA (FIG. 3A, 5' end sgRNA) is indicated and the spacer RNA of the sgRNA is located in the 5' end region of the sgRNA. A cysteine residue (FIG. 3A, WT SpyCas9 Cys) in wild type SpyCas9 is identified in the present disclosure as an available cross-linking site. In FIG. 3A, the Catalytic nuclease lobe is shown as the lighter lobe wherein the relative positions of the RuvC (FIG. 3A, RuvC; RNase H homologous domain) and HNH nuclease (FIG. 3A, HNH; HNH nuclease homologous domain) domains are indicated. The RuvC and HNH nuclease domains, when active, each cut a different DNA strand in target DNA. The C-terminal domain (FIG. 3A, CTD) is involved in recognition of protospacer adjacent motifs (PAM) in target DNA. FIG. 3B presents a model of the domain arrangement of SpyCas9 relative to its primary sequence structure. In FIG. 3B, three regions of the primary sequence correspond to the RuvC domain (FIG. 3B, RuvC-I (amino acids 1-78), RuvC-II (amino acids 719-765), and RuvC-III (amino acids 926-1102)). One region corresponds to the Helical domain (FIG. 3B, Helical Domain (amino acids 79-718). One region corresponds to the HNH domain (FIG. 3B, HNH (amino acids 766-925). One region corresponds to the CTD domain (FIG. 3B, CTD (amino acids 1103-1368). In FIG. 3B, the regions of the primary sequence corresponding to the α-Helical lobe (FIG. 3B, alpha-helical lobe) and the Nuclease domain lobe (FIG. 3B, Nuclease domain lobe) are indicated with brackets.

FIG. 4 depicts an exemplary embodiment of off-target binding and cleavage during genome engineering. In this embodiment, a target nucleic acid (FIG. 4. 115) is contacted with a complex comprising a site-directed polypeptide (e.g., Cas9) (FIG. 4, 105) and a nucleic acid-targeting nucleic acid (e.g., sgRNA or dual-guide RNA) (FIG. 4, 110). The complex comprising the Cas9 binds to a target nucleic acid (FIG. 4, 120). In some instances, the complex binds to an off-target nucleic acid (FIG. 4, 125). In a cleavage step (FIG. 4, 130), the Cas9 of the complex can cleave the target nucleic acid (FIG. 4, 120) and the off-target nucleic acid, thereby generating off-target effects.

FIG. 5 depicts an exemplary embodiment of a method of the disclosure for reducing off-target binding and cleavage events. A target nucleic acid (FIG. 5, 215) is contacted with a complex comprising a site-directed polypeptide (e.g., an active Cas9) (FIG. 5, 205) and a nucleic acid-targeting nucleic acid (e.g., sgRNA or dual-guide RNA) (FIG. 5, 210). The complex binds to a target nucleic acid (FIG. 5, 220). In some instances, the complex comprising the Cas9 and sgRNA binds to an off-target nucleic acid (FIG. 5, 225). Complexes comprising an engineered dCas9 protein (FIG. 5, 235) and an engineered sgRNA (FIG. 5, 236), can be introduced and contacted (FIG. 5, 230) with the target nucleic acid. The dCas9 complexes can either displace or prevent the binding of complexes comprising active Cas9. The active Cas9 can cleave (FIG. 5, 240/245) the target nucleic acid. The active Cas9 is prevented from cleaving the off-target nucleic acid because the dCas9 is preventing its binding and cleavage. In this way, off-target cleavage may be prevented.

FIG. 6 shows the use of tandem Cas9 D10A nickases to excise a single-stranded region of DNA on the same strand of a target nucleic acid and insert a donor polynucleotide.

FIG. 6A shows two D10A sgRNA/dCas9 complexes targeted to two spaced-apart positions on the sense strand of a target polynucleotide. FIG. 6B shows that a region on the sense strand between the targeted sites has been cleaved. FIG. 6C shows the insertion of the donor polynucleotide with overlapping flanking regions.

FIG. 7A shows a system using a single sgRNA/dCas9 complex tethered to a HDR polynucleotide donor adjacent to an active sgRNA/Cas9 complex to direct the donor to the site of the double-stranded break and to position the donor next to the cut site. FIG. 7B shows a system using two spaced-apart sgRNA/dCas9 complexes and a catalytically active sgRNA/Cas9 complex positioned between the two catalytically inactive complexes, wherein the donor is positioned across the double-stranded break.

DETAILED DESCRIPTION OF THE INVENTION

Figure 1A:
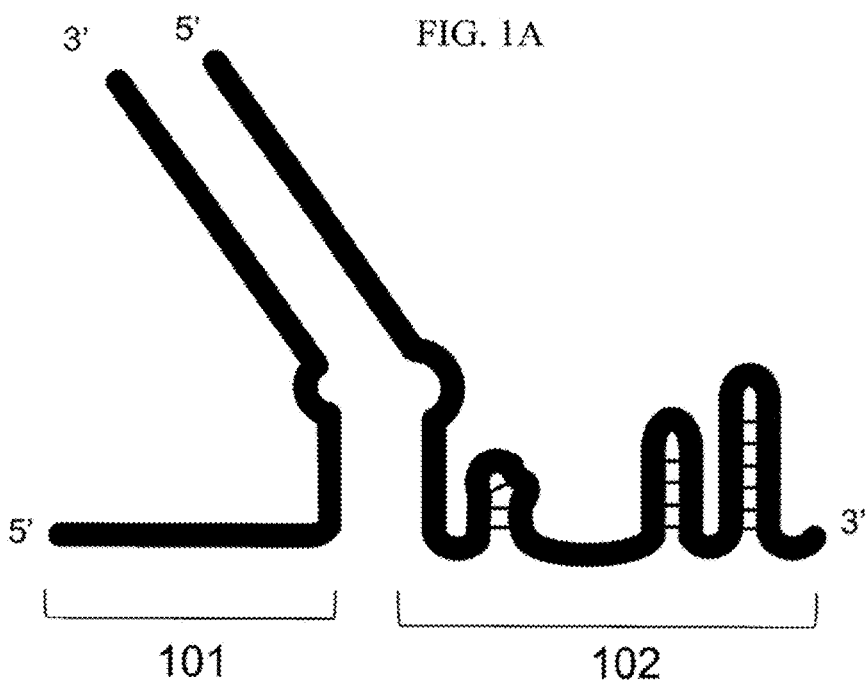
FIG. 1A and FIG. 1B present illustrative examples of Type II CRISPR-Cas9 associated RNAs.

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a sgRNA/dCas9 complex" includes one or more such complexes, reference to "a sgRNA/Cas9 complex" includes one or more such complexes, reference to "a mutation" includes one or more mutations, and the like. It is also to be understood that when reference is made to an embodiment using a sgRNA to target Cas9 or dCas9 to a target site, one skilled in the art can use an alternative embodiment of the invention based on the use of a dual-guide RNA (e.g. crRNA/tracrRNA) in place of the sgRNA.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, preferred materials and methods are described herein.

In view of the teachings of the present specification, one of ordinary skill in the art can apply conventional techniques of immunology, biochemistry, chemistry, molecular biology, microbiology, cell biology, genomics, and recombinant polynucleotides, as taught, for example, by the following standard texts: Antibodies: A Laboratory Manual, Second edition, E. A. Greenfield, 2014, Cold Spring Harbor Laboratory Press, ISBN 978-1-936113-81-1; Culture of Animal Cells: A Manual of Basic Technique and Specialized Applications, 6th Edition, R. I. Freshney, 2010, Wiley-Blackwell, ISBN 978-0-470-52812-9; Transgenic Animal Technology, Third Edition: A Laboratory Handbook, 2014, C. A. Pinkert, Elsevier, ISBN 978-0124104907; The Laboratory Mouse, Second Edition, 2012, H. Hedrich, Academic Press, ISBN 978-0123820082; Manipulating the Mouse Embryo: A Laboratory Manual, 2013, R. Behringer, et al., Cold Spring Harbor Laboratory Press, ISBN 978-1936113019; PCR 2: A Practical Approach, 1995, M. J. McPherson, et al., IRL Press, ISBN 978-0199634248; Methods in Molecular Biology (Series), J. M. Walker, ISSN 1064-3745, Humana Press; RNA: A Laboratory Manual, 2010, D. C. Rio, et al., Cold Spring Harbor Laboratory Press, ISBN 978-0879698911; Methods in Enzymology (Series), Academic Press; Molecular Cloning: A Laboratory Manual (Fourth Edition), 2012, M. R. Green, et al., Cold Spring Harbor Laboratory Press, ISBN 978-1605500560; Bioconjugate Techniques, Third Edition, 2013, G. T. Hermanson, Academic Press, ISBN 978-0123822390; Methods in Plant Biochemistry and Molecular Biology, 1997, W. V. Dashek, CRC Press, ISBN 978-0849394805; Plant Cell Culture Protocols (Methods in Molecular Biology), 2012, V. M. Loyola-Vargas, et al., Humana Press, ISBN 978-1617798177; Plant Transformation Technologies, 2011, C. N. Stewart, et al., Wiley-Blackwell, ISBN 978-0813821955; Recombinant Proteins from Plants (Methods in Biotechnology), 2010, C. Cunningham, et al., Humana Press, ISBN 978-1617370212; Plant Genomics: Methods and Protocols (Methods in Molecular Biology), 2009, D. J. Somers, et al., Humana Press, ISBN 978-1588299970; Plant Biotechnology: Methods in Tissue Culture and Gene Transfer, 2008, R. Keshavachandran, et al., Orient Blackswan, ISBN 978-8173716164.

The term "Cas9 protein" as used herein refers to Type II CRISPR-Cas9 proteins (as described, e.g., in Chylinski, K., (2013) "The tracrRNA and Cas9 families of type II CRISPR-Cas immunity systems," RNA Biol. 2013 10(5): 726-737), including, but not limited to Cas9, Cas9-like, proteins encoded by Cas9 orthologs, Cas9-like synthetic proteins, and variants and modifications thereof. The term "Cas9 protein" as used herein refers to Cas9 wild-type proteins derived from Type II CRISPR-Cas9 systems, modifications of Cas9 proteins, variants of Cas9 proteins, Cas9 orthologs, and combinations thereof. Cas9 proteins can be derived from any of various bacterial species which genomes encode such proteins. Cas proteins for use in the present methods are described further below.

The terms "wild-type," "naturally-occurring," and "unmodified" are used herein to mean the typical (or most common) form, appearance, phenotype, or strain existing in nature; for example, the typical form of cells, organisms, characteristics, polynucleotides, proteins, macromolecular complexes, genes, RNAs, DNAs, or genomes as they occur in and can be isolated from a source in nature. The wild-type form, appearance, phenotype, or strain serve as the original parent before an intentional modification. Thus, mutant, variant, engineered, recombinant, and modified forms are not wild-type forms.

As used herein, the terms "engineered," "genetically engineered," "recombinant," "modified," and "non-naturally occurring" are interchangeable and indicate intentional human manipulation.

As used herein, the terms "nucleic acid," "nucleotide sequence," "oligonucleotide," and "polynucleotide" are interchangeable. All refer to a polymeric form of nucleotides. The nucleotides may be deoxyribonucleotides (DNA) or ribonucleotides (RNA), or analogs thereof, and they may be of any length. Polynucleotides may perform any function and may have any secondary structure and three-dimensional structure. The terms encompass known analogs of natural nucleotides and nucleotides that are modified in the base, sugar and/or phosphate moieties. Analogs of a particular nucleotide have the same base-pairing specificity (e.g., an analog of A base pairs with T). A polynucleotide may comprise one modified nucleotide or multiple modified nucleotides. Examples of modified nucleotides include methylated nucleotides and nucleotide analogs. Nucleotide structure may be modified before or after a polymer is assembled. Following polymerization, polynucleotides may be additionally modified via, for example, conjugation with a labeling component or target-binding component. A nucleotide sequence may incorporate non-nucleotide components. The terms also encompass nucleic acids comprising modified backbone residues or linkages, that (i) are synthetic, naturally occurring, and non-naturally occurring, and (ii) have similar binding properties as a reference polynucleotide (e.g., DNA or RNA). Examples of such analogs include, but are not limited to, phosphorothioates, phosphoramidates, methyl phosphonates, chiral-methyl phosphonates, 2-O-methyl ribonucleotides, peptide-nucleic acids (PNAs), and morpholino structures.

Polynucleotide sequences are displayed herein in the conventional 5' to 3' orientation.

As used herein, the term "complementarity" refers to the ability of a nucleic acid sequence to form hydrogen bond(s) with another nucleic acid sequence (e.g., through traditional Watson-Crick base pairing). A percent complementarity indicates the percentage of residues in a nucleic acid molecule that can form hydrogen bonds with a second nucleic acid sequence. When two polynucleotide sequences have 100% complementarity, the two sequences are perfectly complementary, i.e., all of a first polynucleotide's contiguous residues hydrogen bond with the same number of contiguous residues in a second polynucleotide.

As used herein, the term "sequence identity" generally refers to the percent identity of bases or amino acids determined by comparing a first polynucleotide or polypeptide to a second polynucleotide or polypeptide using algorithms having various weighting parameters. Sequence identity between two polypeptides or two polynucleotides can be determined using sequence alignment by various methods and computer programs (e.g., BLAST, CS-BLAST, FASTA, HMMER, L-ALIGN, etc.), available through the worldwide web at sites including GENBANK (ncbi.nlm.nih.gov/genbank/) and EMBL-EBI (ebi.ac.uk.). Sequence identity between two polynucleotides or two polypeptide sequences is generally calculated using the standard default parameters of the various methods or computer programs.

As used herein a "stem-loop structure" or "stem-loop element" refers to a polynucleotide having a secondary structure that includes a region of nucleotides that are known or predicted to form a double-stranded region (the "stem element") that is linked on one side by a region of predominantly single-stranded nucleotides (the "loop element"). The term "hairpin" element is also used herein to refer to stem-loop structures. Such structures are well known in the art. The base pairing may be exact. However, as is known in the art, a stem element does not require exact base pairing. Thus, the stem element may include one or more base mismatches or non-paired bases.

As used herein, the term "recombination" refers to a process of exchange of genetic information between two polynucleotides.

As used herein, the term "homology-directed repair" or "HDR" refers to DNA repair that takes place in cells, for example, during repair of double-stranded and single-stranded breaks in DNA. HDR requires nucleotide sequence homology and uses a "donor template" (donor template DNA, polynucleotide donor, or oligonucleotide (used interchangeably herein) to repair the sequence where the double-stranded break occurred (e.g., DNA target sequence). This results in the transfer of genetic information from, for example, the donor template DNA to the DNA target sequence. HDR may result in alteration of the DNA target sequence (e.g., insertion, deletion, mutation) if the donor template DNA sequence or oligonucleotide sequence differs from the DNA target sequence and part or all of the donor template DNA polynucleotide or oligonucleotide is incorporated into the DNA target sequence. In some embodiments, an entire donor template DNA polynucleotide, a portion of the donor template DNA polynucleotide, or a copy of the donor polynucleotide is integrated at the site of the DNA target sequence.

As used herein the term "non-homologous end joining" or "NHEJ" refers to the repair of double-stranded breaks in DNA by direct ligation of one end of the break to the other end of the break without a requirement for a donor template DNA. NHEJ in the absence of a donor template DNA often results in a small number of nucleotides randomly inserted or deleted at the site of the double-stranded break.

Alternative mechanisms of DNA insertion that do not require sequence homology between the donor and the target sequence can also be used for nucleic acid insertion. These mechanisms involve various components of the cellular DNA repair machinery and it is to be understood that the scope of the invention is not bound by the use of any particular mechanism for insertion of nucleic acid after target nucleic acid is cut or nicked by a site-specific polynucleotide.

The terms "vector" and "plasmid" are used interchangeably and as used herein refer to a polynucleotide vehicle to introduce genetic material into a cell. Vectors can be linear or circular. Vectors can integrate into a target genome of a host cell or replicate independently in a host cell. Vectors can comprise, for example, an origin of replication, a multicloning site, and/or a selectable marker. An expression vector typically comprises an expression cassette. Vectors and plasmids include, but are not limited to, integrating vectors, prokaryotic plasmids, eukaryotic plasmids, plant synthetic chromosomes, episomes, viral vectors, cosmids, and artificial chromosomes. As used herein the term "expression cassette" is a polynucleotide construct, generated recombinantly or synthetically, comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in an expression vector.

As used herein the term "expression cassette" is a polynucleotide construct, generated recombinantly or synthetically, comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in an expression vector.

As used herein a "targeting vector" is a recombinant DNA construct typically comprising tailored DNA arms homologous to genomic DNA that flanks critical elements of a target gene or target sequence. When introduced into a cell, the targeting vector integrates into the cell genome via homologous recombination. Elements of the target gene can be modified in a number of ways including deletions and/or insertions. A defective target gene can be replaced by a functional target gene, or in the alternative a functional gene can be knocked out. Optionally a targeting vector comprises a selection cassette comprising a selectable marker that is introduced into the target gene. Targeting regions adjacent or sometimes within a target gene can be used to affect regulation of gene expression.

As used herein, the terms "regulatory sequences," "regulatory elements," and "control elements" are interchangeable and refer to polynucleotide sequences that are upstream (5' non-coding sequences), within, or downstream (3' non-translated sequences) of a polynucleotide target to be expressed. Regulatory sequences influence, for example, the timing of transcription, amount or level of transcription, RNA processing or stability, and/or translation of the related structural nucleotide sequence. Regulatory sequences may include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like.

As used herein the term "operably linked" refers to polynucleotide sequences or amino acid sequences placed into a functional relationship with one another. For instance, a promoter or enhancer is operably linked to a coding sequence if it regulates, or contributes to the modulation of, the transcription of the coding sequence. Operably linked DNA sequences encoding regulatory sequences are typically contiguous to the coding sequence. However, enhancers can function when separated from a promoter by up to several kilobases or more. Accordingly, some polynucleotide elements may be operably linked but not contiguous.

As used herein, the term "expression" refers to transcription of a polynucleotide from a DNA template, resulting in, for example, an mRNA or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene product." Expression may include splicing the mRNA in a eukaryotic cell, if the polynucleotide is derived from genomic DNA.

As used herein the term "modulate" refers to a change in the quantity, degree or amount of a function. For example, the methods disclosed herein may modulate Cas9-mediated targeting efficiency by decreasing or eliminating off-target cleavage, thereby enhancing cleavage at the target site, or may enhance HDR and decrease the likelihood of NHEJ events. Accordingly, the term "modulating targeting" may denote increasing desired targeting events and/or inhibiting off-target cleavage. Similarly, "modulating HDR" can denote increasing HDR and/or decreasing NHEJ.

Modulation can be assayed by determining any characteristic directly or indirectly affected by the expression of the target gene. Such characteristics include, e.g., changes in targeting efficiency, RNA or protein levels, protein activity, product levels, associated gene expression, or activity level of reporter genes. Thus, "modulation" of gene expression includes both gene activation and gene repression.

As used herein, the term "amino acid" refers to natural and synthetic (unnatural) amino acids, including amino acid analogs, modified amino acids, peptidomimetics, glycine, and D or L optical isomers.

As used herein, the terms "peptide," "polypeptide," and "protein" are interchangeable and refer to polymers of amino acids. A polypeptide may be of any length. It may be branched or linear, it may be interrupted by non-amino acids, and it may comprise modified amino acids. The terms may be used to refer to an amino acid polymer that has been modified through, for example, acetylation, disulfide bond formation, glycosylation, lipidation, phosphorylation, cross-linking, and/or conjugation (e.g., with a labeling component or ligand). Polypeptide sequences are displayed herein in the conventional N-terminal to C-terminal orientation.

Polypeptides and polynucleotides can be made using routine techniques in the field of molecular biology (see, e.g., standard texts discussed above). Further, essentially any polypeptide or polynucleotide can be custom ordered from commercial sources.

The term "binding" as used herein includes a non-covalent interaction between macromolecules (e.g., between a protein and a polynucleotide, between a polynucleotide and a polynucleotide, and between a protein and a protein). Such non-covalent interaction is also referred to as "associating" or "interacting" (e.g., when a first macromolecule interacts with a second macromolecule, the first macromolecule binds to second macromolecule in a non-covalent manner). Some portions of a binding interaction may be sequence-specific; however, all components of a binding interaction do not need to be sequence-specific, such as a protein's contacts with phosphate residues in a DNA backbone. Binding interactions can be characterized by a dissociation constant (Kd). "Affinity" refers to the strength of binding. An increased binding affinity is correlated with a lower Kd. An example of non-covalent binding is hydrogen bond formation between base pairs.

As used herein, the term "isolated" can refer to a nucleic acid or polypeptide that, by the hand of a human, exists apart from its native environment and is therefore not a product of nature. Isolated means substantially pure. An isolated nucleic acid or polypeptide can exist in a purified form and/or can exist in a non-native environment such as, for example, in a recombinant cell.

As used herein, a "host cell" generally refers to a biological cell. A cell can be the basic structural, functional and/or biological unit of a living organism. A cell can originate from any organism having one or more cells. Examples of host cells include, but are not limited to: a prokaryotic cell, eukaryotic cell, a bacterial cell, an archaeal cell, a cell of a single-cell eukaryotic organism, a protozoa cell, a cell from a plant (e.g. cells from plant crops, fruits, vegetables, grains, soy bean, corn, maize, wheat, seeds, tomatoes, rice, cassava, sugarcane, sunflower, sorghum, millet, alfalfa, oil-producing *Brassica* (for example, but not limited to, oilseed rape/canola), pumpkin, hay, potatoes, cotton, cannabis, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. Agardh*, and the like), seaweeds (e.g. kelp), a fungal cell (e.g., a yeast cell, a cell from a mushroom), an animal cell, a cell from an invertebrate animal (e.g. fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.). Further, a cell can be a stem cell or progenitor cell.

As used herein, the term "transgenic organism" refers to an organism comprising a recombinantly introduced polynucleotide.

As used herein, the terms "transgenic plant cell" and "transgenic plant" are interchangeable and refer to a plant cell or a plant containing a recombinantly introduced polynucleotide. Included in the term transgenic plant is the progeny (any generation) of a transgenic plant or a seed such that the progeny or seed comprises a DNA sequence encoding a recombinantly introduced polynucleotide or a fragment thereof.

As used herein, the phrase "generating a transgenic plant cell or a plant" refers to using recombinant DNA methods and techniques to construct a vector for plant transformation to transform the plant cell or the plant and to generate the transgenic plant cell or the transgenic plant.

A CRISPR (Clustered Regularly Interspaced Short Palindromic Repeats) is a genomic locus found in the genomes of many prokaryotes (e.g., bacteria and archaea). CRISPR loci provide resistance to foreign invaders (e.g., virus, phage) in prokaryotes. In this way, the CRISPR system can be thought to function as a type of immune system to help defend prokaryotes against foreign invaders. There are three stages of CRISPR locus function: integration of new sequences into the locus, biogenesis of CRISPR RNA (crRNA), and silencing of foreign invader nucleic acid.

A CRISPR locus includes a number of short repeating sequences referred to as "repeats." Repeats can form hairpin structures and/or repeats can be unstructured single-stranded sequences. The repeats occur in clusters. Repeats frequently diverge between species. Repeats are regularly interspaced with unique intervening sequences, referred to as "spacers," resulting in a repeat-spacer-repeat locus architecture. Spacers are identical to or have high homology with known foreign invader sequences. A spacer-repeat unit encodes a crisprRNA (crRNA). A crRNA refers to the mature form of the spacer-repeat unit. A crRNA comprises a "seed" sequence that is involved in targeting a target nucleic acid (e.g., possibly as a surveillance mechanism against foreign nucleic acid). A seed sequence is typically located towards the 5' end of a crRNA (e.g. in the Cascade complex; for a description of the Cascade complex see, e.g., Jore, M. M. et al., "Structural basis for CRISPR RNA-guided DNA recognition by Cascade," Nature Structural & Molecular Biology (2011) 18:529-536) or at the 3' end of the spacer of a crRNA (e.g., in a Type II CRISPR-Cas9 system), directly adjacent to the first stem.

A CRISPR locus comprises polynucleotide sequences encoding for CRISPR Associated Genes (Cas) genes. Cas genes are involved in the biogenesis and/or the interference stages of crRNA function. Cas genes display extreme sequence (e.g., primary sequence) divergence between species and homologues. For example, Cas1 homologues can comprise less than 10% primary sequence identity between homologues. Some Cas genes comprise homologous secondary and/or tertiary structures. For example, despite extreme sequence divergence, many members of the Cas6 family of CRISPR proteins comprise a N-terminal ferredoxin-like fold. Cas genes are named according to the organism from which they are derived. For example, Cas genes in *Staphylococcus epidermidis* can be referred to as Csm-type, Cas genes in *Streptococcus thermophilus* can be referred to as Csn-type, and Cas genes in *Pyrococcus furiosus* can be referred to as Cmr-type.

The integration stage of a CRISPR system refers to the ability of the CRISPR locus to integrate new spacers into the crRNA array upon being infected by a foreign invader. Acquisition of the foreign invader spacers can help confer immunity to subsequent attacks by the same foreign invader. Integration typically occurs at the leader end of the CRISPR locus. Cas proteins (e.g., Cas1 and Cas2) are involved in integration of new spacer sequences. Integration proceeds similarly for some types of CRISPR systems (e.g., Type I-III).

Mature crRNAs are processed from a longer polycistronic CRISPR locus transcript (i.e., pre-crRNA array). A pre-crRNA array comprises a plurality of crRNAs. The repeats in the pre-crRNA array are recognized by Cas genes. Cas genes bind to the repeats and cleave the repeats. This action can liberate the plurality of crRNAs. crRNAs can be subjected to further events to produce the mature crRNA form such as trimming (e.g., with an exonuclease). A crRNA may comprise all, some, or none of the CRISPR repeat sequence.

Interference refers to the stage in the CRISPR system that is functionally responsible for combating infection by a foreign invader. CRISPR interference follows a similar mechanism to RNA interference (RNAi: e.g., wherein a target RNA is targeted (e.g., hybridized) by a short interfering RNA (siRNA)), which results in target RNA degradation and/or destabilization. CRISPR systems perform interference of a target nucleic acid by coupling crRNAs and Cas genes, thereby forming CRISPR ribonucleoproteins (crRNPs). crRNA of the crRNP guides the crRNP to foreign invader nucleic acid, (e.g., by recognizing the foreign invader nucleic acid through hybridization). Hybridized target foreign invader nucleic acid-crRNA units are subjected to cleavage by Cas proteins. Target nucleic acid interference typically requires a protospacer adjacent motif (PAM) in a target nucleic acid.

There are at least four types of CRISPR systems: Type I, Type II, Type III, and Type U. More than one CRISPR type system can be found in an organism. CRISPR systems can be complementary to each other, and/or can lend functional units in trans to facilitate CRISPR locus processing. Type II systems can be further subdivided into II-A (contains Csn2 locus) and II-B (contains Cas4 locus) and Type II-C (neither Csn2 nor Cas4, e.g. *N. meningitides*). Modifications of the components of CRISPR-Type II systems are extensively discussed in the present specification.

crRNA biogenesis in a Type II CRISPR system comprises a trans-activating CRISPR RNA (tracrRNA). A tracrRNA is typically modified by endogenous RNaseIII. The tracrRNA hybridizes to a crRNA repeat in the pre-crRNA array. Endogenous RNaseIII is recruited to cleave the pre-crRNA. Cleaved crRNAs are subjected to exoribonuclease trimming to produce the mature crRNA form (e.g., 5' trimming). The tracrRNA typically remains hybridized to the crRNA. The tracrRNA and the crRNA associate with a site-directed polypeptide (e.g., Cas9). The crRNA of the crRNA-tracrRNA-Cas9 complex can guide the complex to a target nucleic acid to which the crRNA can hybridize. Hybridization of the crRNA to the target nucleic acid activates a wild-type, cognate Cas9 for target nucleic acid cleavage. Target nucleic acid in a Type II CRISPR system comprises a PAM. In some embodiments, a PAM is essential to facilitate binding of a site-directed polypeptide (e.g., Cas9) to a target nucleic acid.

Figure 3A:
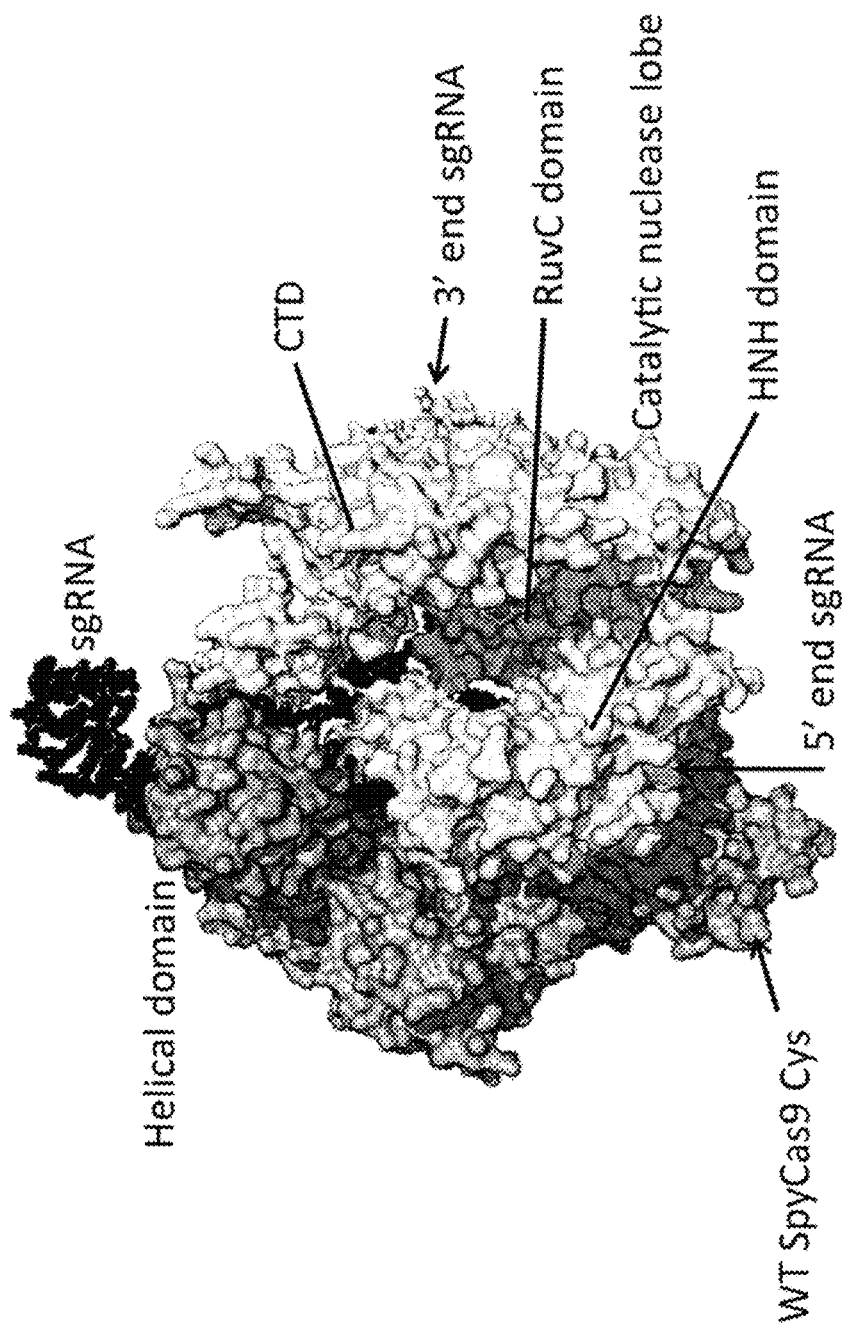
FIG. 3A and FIG. 3B relate to structural information for a sgRNA/Cas protein complex and a Cas protein, respectively.
Figure 3B:
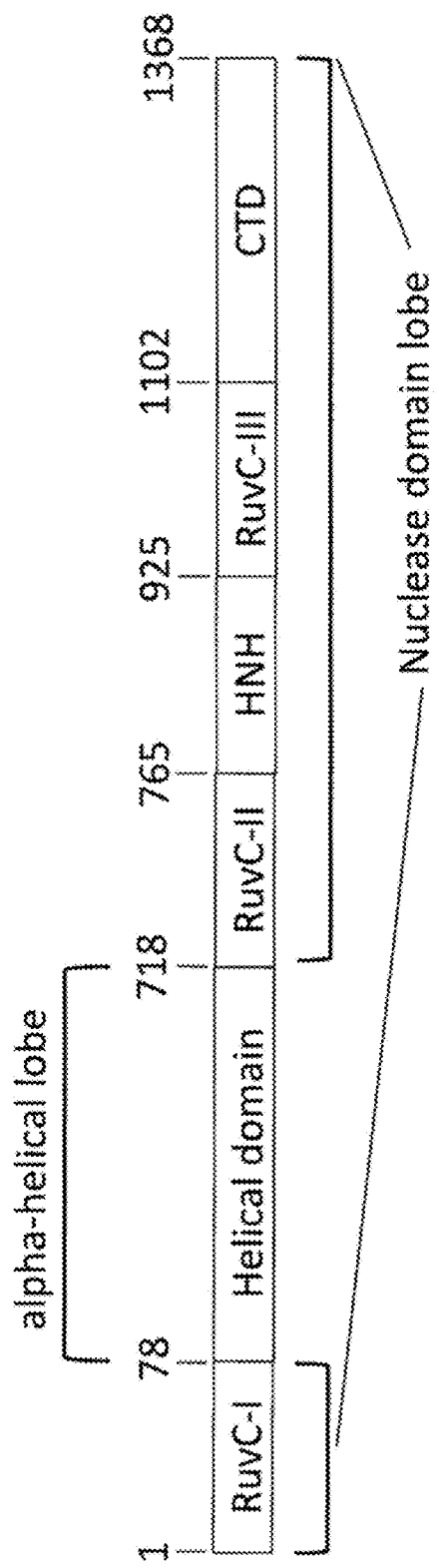

Cas9 is an exemplary Type II CRISPR Cas protein. Cas9 is an endonuclease that can be programmed by the tracrRNA/crRNA to cleave, site-specifically, target DNA using two distinct endonuclease domains (HNH and RuvC/RNase H-like domains) (see U.S. Published Patent Application No. 2014-0068797, published 6 Mar. 2014; see also Jinek M., et al., "A programmable dual-RNA-guided DNA endonuclease in adaptive bacterial immunity," Science (2012) 337:816-821), one for each strand of the DNA's double helix. RuvC and HNH together produce double-stranded breaks (DSBs), and separately can produce single-stranded breaks. FIG. 3A presents a model of the domain arrangement of SpyCas9 (*S. pyogenes* Cas9) relative to its primary sequence structure. Two RNA components of a Type II CRISPR-Cas9 system are illustrated in FIG. 1A. Typically each CRISPR-Cas9 system comprises a tracrRNA and a crRNA. However, this requirement can be bypassed by using an engineered sgRNA, described more fully below, containing a designed hairpin that mimics the tracrRNA-crRNA complex (Jinek et al., 2012). Base-pairing between the sgRNA and target DNA causes double-stranded breaks (DSBs) due to the endonuclease activity of Cas9. Binding specificity is determined by both sgRNA-DNA base pairing and a short DNA motif (protospacer adjacent motif [PAM] sequence: NGG) juxtaposed to the DNA complementary region (Marraffini L A, Sontheimer E J. "CRISPR interference: RNA-directed adaptive immunity in bacteria and archaea," Nat Rev Genet., 2010; 11:181-190). Thus, the CRISPR system only requires a minimal set of two molecules—the Cas9 protein and the sgRNA.

A large number of Cas9 orthologs are known in the art as well as their associated tracrRNA and crRNA components (see, e.g., "Supplementary Table S2. List of bacterial strains with identified Cas9 orthologs," Fonfara, Ines, et al., "Phylogeny of Cas9 Determines Functional Exchangeability of Dual-RNA and Cas9 among Orthologous Type II CRISPR/Cas Systems," Nucleic Acids Research (2014) 42:2577-2590, including all Supplemental Data; Chylinski K., et al., "Classification and evolution of type II CRISPR-Cas systems," Nucleic Acids Research (2014) 42:6091-6105, including all Supplemental Data); Esvelt, K. M., et al., "Orthogonal Cas9 proteins for RNA-guided gene regulation and editing," Nature Methods (2013) 10:1116-1121). A number of orthogonal Cas9 proteins have been identified including Cas9 proteins from *Neisseria meningitidis, Streptococcus thermophilus* and *Staphylococcus aureus*.

As used herein, "a Cas9 protein" refers to a Cas9 protein derived from any species, subspecies or strain of bacteria that encodes Cas9, as well as variants and orthologs of the particular Cas9 in question. The Cas9 proteins can either be directly isolated and purified from bacteria, or synthetically or recombinantly produced, or typically delivered using a construct encoding the protein, including without limitation, naked DNA, plasmid DNA, a viral vector and mRNA for Cas9 expression.

Variants and modifications of Cas9 proteins are known in the art. U.S. Published Patent Application 20140273226, published Sep. 18, 2014, incorporated herein by reference in its entirety, discusses the *S. pyogenes* Cas9 gene, Cas9 protein, and variants of the Cas9 protein including host-specific codon optimized Cas9 coding sequences (e.g., ¶¶0129-0137 therein) and Cas9 fusion proteins (e.g., ¶¶233-240 therein). U.S. Published Patent Application 20140315985, published Oct. 23, 2014, incorporated herein in its entirety, teaches a large number of exemplary wild-type Cas9 polypeptides (e.g., SEQ ID NO: 1-256, SEQ ID NOS: 795-1346, therein) including the sequence of Cas9 from *S. pyogenes* (SEQ ID NO: 8, therein). Modifications and variants of Cas9 proteins are also discussed (e.g., ¶¶504-608, therein). Non-limiting examples of Cas9 proteins include Cas9 proteins from *S. pyogenes* (GI: 15675041); *Listeria innocua* Clip 11262 (GI:16801805); *Streptococcus mutans* UA159 (GI:24379809); *Streptococcus thermophilus* LMD-9 (*S. thermophilus* A, GI:11662823; *S. thermophilus* B, GI:116627542); *Lactobacillus buchneri* NRRL B-30929 (GI:331702228); *Treponema denticola* ATCC 35405 (GI:42525843); *Francisella novicida* U112 (GI:118497352); *Campylobacter jejuni* subsp. *Jejuni* NCTC 11168 (GI:218563121); *Pasteurella multocida* subsp. *multocida* str. Pm70 (GI:218767588); *Neisseria meningitidis* Zs491 (GI:15602992) and *Actinomyces naeslundii* (GI:489880078).

Aspects of the present invention can be practiced by one of ordinary skill in the art following the guidance of the specification to use Type II CRISPR-Cas9 proteins and Cas-protein encoding polynucleotides, including, but not limited to Cas9, Cas9-like, proteins encoded by Cas9 orthologs, Cas9-like synthetic proteins, and variants and modifications thereof. The cognate RNA components of these Cas proteins can be manipulated and modified for use in the practice of the present invention by one of ordinary skill in the art following the guidance of the present specification.

By "dCas9" is meant a nuclease-deactivated Cas9, also termed "catalytically inactive", "catalytically dead Cas9" or "dead Cas9." Such molecules lack all or a portion of endonuclease activity and can therefore be used to regulate genes in an RNA-guided manner (Jinek M., et al., "A programmable dual-RNA-guided DNA endonuclease in adaptive bacterial immunity," Science (2012) 337:816-821). This is accomplished by introducing mutations that inactivate Cas9 nuclease function and is typically accomplished by mutating both of the two catalytic residues (D10A in the RuvC-1 domain, and H840A in the HNH domain, numbered relative to *S. pyogenes* Cas9) of the gene encoding Cas9. It is understood that mutation of other catalytic residues to reduce activity of either or both of the nuclease domains can also be carried out by one skilled in the art. In doing so, dCas9 is unable to cleave dsDNA but retains the ability to target DNA. The Cas9 double mutant with changes at amino acid positions D10A and H840A completely inactivates both the nuclease and nickase activities. Targeting specificity is determined by complementary base-pairing of an sgRNA to the genomic locus and the protospacer adjacent motif (PAM).

dCas9 can be used alone or in fusions to synthetically repress (CRISPRi) or activate (CRISPRa) gene expression. CRISPRi can work independently of host cellular machineries. In some embodiments, only a dCas9 protein and a customized sgRNA designed with a complementary region to any gene of interest direct dCas9 to a chosen genomic location. In other embodiments, dCas9 can be fused to a transcription factor, such as a repressor, and the fused Cas9-transcription factor can then work in concert with cellular machineries. The binding specificity is determined jointly by the complementary region on the sgRNA and a short DNA motif (protospacer adjacent motif or PAM) juxtaposed to the DNA complementary region, dependent on the species in question. (see, e.g., Anders C., et al., "Structural basis of PAM-dependent target DNA recognition by the Cas9 endonuclease," Nature (2014) 513:569-573). In the case of *S. pyogenes*, this sequence is NGG. To achieve transcriptional repression, dCas9 can be used by itself (whereby it represses transcription through steric hindrance). Taken together sgRNA and dCas9 provide a minimum system for gene-specific regulation in any organism. (Qi, L. S., et al., "Repurposing CRISPR as an RNA-Guided Platform for Sequence-Specific Control of Gene Expression" Cell (2013) 152:1173-1183). CRISPRa is carried out by dCas9-transcription factor (activator) fusions.

Figure 1B:
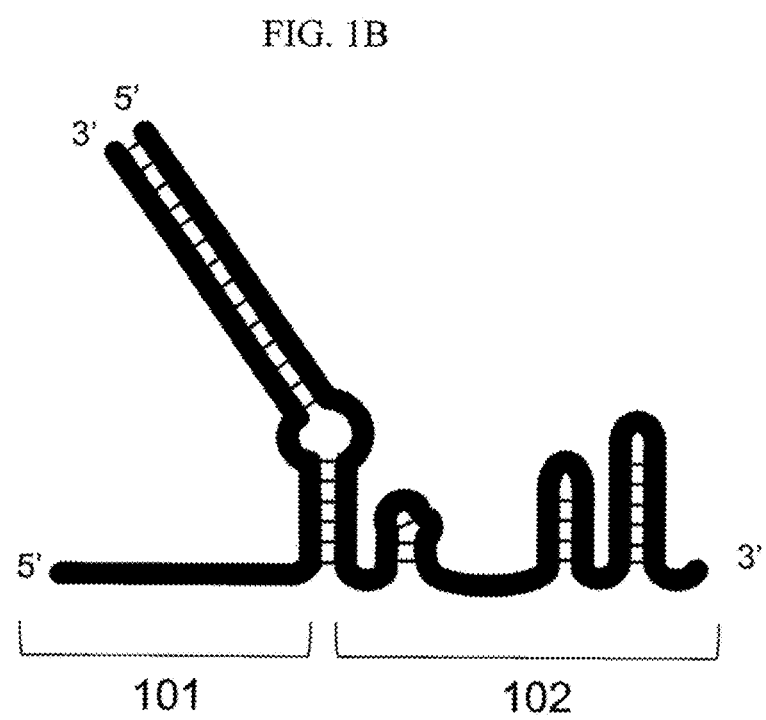

By a "Cas9 nickase" is meant a Cas9 mutant that does not retain the ability to make double-stranded breaks in a target nucleic acid sequence, but maintains the ability to bind to and make a single-stranded break at a target site. Such a mutant will typically include a mutation in one, but not both of the Cas9 endonuclease domains (HNH and RuvC). Thus, an amino acid mutation at position D10A or H840A in Cas9, numbered relative to *S. pyogenes*, can result in the inactivation of the nuclease catalytic activity and convert Cas9 to a nickase enzyme that makes single-stranded breaks at the target site. It is to be understood that other site-directed polypeptides such as meganucleases, TALE nucleases, Zinc-finger nucleases, MEGA-TALs and others known to one of skill in the art can be used in alternative embodiments.

crRNA has a region of complementarity to a potential DNA target sequence (FIG. 1A, the dark, 5' region of the crRNA) and a second region that forms base-pair hydrogen bonds with the tracrRNA to form a secondary structure, typically to form at least a stem structure (FIG. 1A, the light region extending to the 3' end of the crRNA). The region of complementarity to the DNA target is the spacer. The tracrRNA and a crRNA interact through a number of base-pair hydrogen bonds to form secondary RNA structures, for example, as illustrated in FIG. 1B. Complex formation between tracrRNA/crRNA and Cas protein results in conformational change of the Cas protein that facilitates binding to DNA, endonuclease activities of the Cas protein, and crRNA-guided site-specific DNA cleavage by the endonuclease. For a Cas protein/tracrRNA/crRNA complex to cleave a DNA target sequence, the DNA target sequence is adjacent to a cognate protospacer adjacent motif (PAM).

Figure 2:
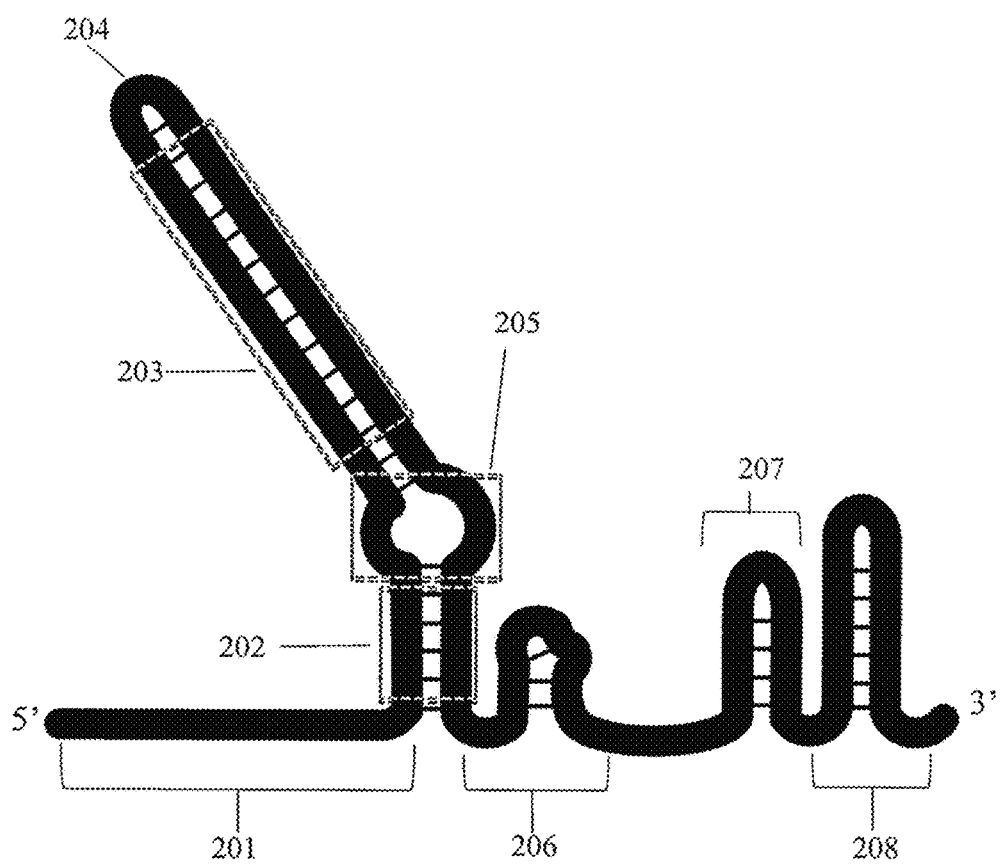
FIG. 2 shows another example of a Type II CRISPR-Cas9 associated RNA. The figure illustrates a single-guide RNA (sgRNA) wherein the crRNA is covalently joined to the tracrRNA and forms a RNA polynucleotide secondary structure through base-pair hydrogen bonding (see, e.g., U.S. Published Patent Application No. 2014-0068797, published 6 Mar. 2014). The figure presents an overview of and nomenclature for secondary structural elements of a sgRNA of the *S. pyogenes* Cas9 including the following: a spacer element (FIG. 2, 201); a first stem element comprising a lower stem element (FIG. 2, 202), a bulge element comprising unpaired nucleotides (FIG. 2, 205), and an upper stem element (FIG. 2, 203); a loop element (FIG. 2, 204) comprising unpaired nucleotides; (a first hairpin element comprises the first stem element and the loop element); a nexus element (FIG. 2, 206); a second hairpin element comprising a second stem element (FIG. 2, 207); and a third hairpin element comprising a third stem element (FIG. 2, 208). (See, e.g., FIGS. 1 and 3 of Briner, A. E., et al., "Guide RNA Functional Modules Direct Cas9 Activity and Orthogonality," Molecular Cell (2014) 56:333-339.) The figure is not proportionally rendered nor is it to scale. The locations of indicators are approximate.

The term "sgRNA" typically refers to a single-guide RNA (i.e., a single, contiguous polynucleotide sequence) that essentially comprises a crRNA connected at its 3' end to the 5' end of a tracrRNA through a "loop" sequence (see, e.g., U.S. Published Patent Application No. 20140068797, published 6 Mar. 2014, incorporated herein by reference in its entirety). sgRNA interacts with a cognate Cas protein essentially as described for tracrRNA/crRNA polynucleotides, as discussed above. Similar to crRNA, sgRNA has a spacer, a region of complementarity to a potential DNA target sequence (FIG. 2, 201), adjacent a second region that forms base-pair hydrogen bonds that form a secondary structure, typically a stem structure (FIG. 2, 202, 203, 204, 205). The term includes truncated single-guide RNAs (tru-sgRNAs) of approximately 17-18 nt. (See, e.g., Fu, Y. et. al., "Improving CRISPR-Cas nuclease specificity using truncated guide RNAs," Nat Biotechnol. (2014) 32:279-284). The term also encompasses functional miniature sgRNAs with expendable features removed, but that retain an essential and conserved module termed the "nexus" located in the portion of sgRNA that corresponds to tracrRNA (not crRNA). See, e.g, U.S. Published Patent Application No. 20140315985, published 23 Oct. 2014, incorporated herein by reference in its entirety; Briner et al., "Guide RNA Functional Modules Direct Cas9 Activity and Orthogonality," Molecular Cell (2014) 56:333-339. The nexus is located immediately downstream of (i.e., located in the 3' direction from) the lower stem in Type II CRISPR-Cas9 systems. An example of the relative location of the nexus is illustrated in the sgRNA shown in FIG. 2. The nexus confers the binding of a sgRNA or a tracrRNA to its cognate Cas9 protein and confers an apoenzyme to haloenzyme conformational transition.

With reference to a crRNA or sgRNA, a "spacer" or "spacer element" as used herein refers to the polynucleotide sequence that can specifically hybridize to a target nucleic acid sequence. The spacer element interacts with the target nucleic acid sequence through hydrogen bonding between complementary base pairs (i.e., paired bases). A spacer element binds to a selected DNA target sequence. Accordingly, the spacer element is a DNA target-binding sequence. The spacer element determines the location of Cas protein's site-specific binding and endonucleolytic cleavage. Spacer elements range from ~17- to ~84 nucleotides in length, depending on the Cas protein with which they are associated, and have an average length of 36 nucleotides (Marraffini, et al., "CRISPR interference: RNA-directed adaptive immunity in bacteria and archaea," Nature reviews Genetics (2010) 11:181-190). In a Type II CRISPR-Cas9 system the spacer element typically comprises a "seed" sequence that is involved in targeting a target nucleic acid. For example, for SpyCas9, the functional length for a spacer to direct specific cleavage is typically about 12-25 nucleotides. Variability of the functional length for a spacer element is known in the art (e.g., U.S. Published Patent Application No. 20140315985, published 23 Oct. 2014, incorporated herein by reference in its entirety).

FIG. 3A provides a three-dimensional model based on the crystal structure of *S. pyogenes* Cas9 (SpyCas9) in an active complex with sgRNA. The relationship of the sgRNA to the Helical domain and the Catalytic domain is illustrated. The 3' and 5' ends of the sgRNA are indicated, as well as exposed portions of the sgRNA. The spacer RNA of the sgRNA is not visible because it is surrounded by the α-Helical lobe (Helical domain) and the Catalytic nuclease lobe (Catalytic domain). The spacer RNA of the sgRNA is located in the 5' end region of the sgRNA. The RuvC and HNH nuclease domains, when active, each cut a different DNA strand in target DNA. The C-terminal domain (CTD) is involved in recognition of protospacer adjacent motifs (PAMs) in target DNA.

U.S. Published Patent Application No. 20140315985, published 23 Oct. 2014, incorporated herein by reference in its entirety; and Briner et al., "Guide RNA Functional Modules Direct Cas9 Activity and Orthogonality," Molecular Cell (2014) 56:333-339, disclose consensus sequences and secondary structures of predicted sgRNAs for several sgRNA/Cas9 families. The general arrangement of secondary structures in the predicted sgRNAs up to and including the nexus are presented in FIG. 2 herein which presents an overview of and nomenclature for elements of the sgRNA of the *S. pyogenes* Cas9. Relative to FIG. 2, there is variation in the number and arrangement of stem structures located 3' of the nexus in the sgRNAs of U.S. Published Patent Application No. 2014-0315985 and Briner, et al. Ran et al., "In vivo genome editing using *Staphylococcus aureus* Cas9," Nature (2015) 520:186-191, including all extended data) present the crRNA/tracrRNA sequences and secondary structures of eight Type II CRISPR-Cas9 systems (see Extended Data FIG. 1 of Ran, et al.). Further, Fonfara, et al., ("Phylogeny of Cas9 Determines Functional Exchangeability of Dual-RNA and Cas9 among Orthologous Type II CRISPR/Cas Systems," Nucleic Acids Research (2014) 42:2577-2590, including all Supplemental Data, in particular Supplemental Figure S11) present the crRNA/tracrRNA sequences and secondary structures of eight Type II CRISPR-Cas9 systems.

By "guide polynucleotide" is meant any polynucleotide that site-specifically guides Cas9 or dCas9 to a target, or off-target, nucleic acid. Many such guide polynucleotides are known, such as but not limited to sgRNA (including miniature and truncated sgRNAs), dual-guide RNA, including but not limited to, crRNA/tracrRNA molecules, as described above, and the like.

By "donor polynucleotide" is meant a polynucleotide that can be directed to, and inserted into a target site of interest to modify the target nucleic acid. All or a portion of the donor polynucleotide can be inserted into the target nucleic acid. The donor polynucleotide is used for repair of the break in the target DNA sequence resulting in the transfer of genetic information (i.e., polynucleotide sequences) from the donor at the site or in close proximity of the break in the DNA. Accordingly, new genetic information (i.e., polynucleotide sequences) may be inserted or copied at a target DNA site. The donor polynucleotide can be double- or single-stranded DNA, RNA, a vector, plasmid, or the like. Non-symmetrical polynucleotide donors can also be used that are composed of two DNA oligonucleotides. They are partially complementary, and each can include a flanking region of homology. The donor can be used to insert or replace polynucleotide sequences in a target sequence, for example, to introduce a polynucleotide that encodes a protein or functional RNA (e.g., siRNA), to introduce a protein tag, to modify a regulatory sequence of a gene, or to introduce a regulatory sequence to a gene (e.g. a promoter, an enhancer, an internal ribosome entry sequence, a start codon, a stop codon, a localization signal, or polyadenylation signal), to modify a nucleic acid sequence (e.g., introduce a mutation), and the like.

Targeted DNA modifications using donor polynucleotides for large changes (e.g., more than 100 bp insertions or deletions) traditionally use plasmid-based donor templates that contain homology arms flanking the site of alteration. Each arm can vary in length, but is typically longer than about 100 bp, such as 100-1500 bp, e.g., 100 . . . 200 . . . 300 . . . 400 . . . 500 . . . 600 . . . 700 . . . 800 . . . 900 . . . 1000 . . . 1500 bp or any integer between these values. However, these numbers can vary, depending on the size of the donor polynucleotide and the target polynucleotide. This method can be used to generate large modifications, including insertion of reporter genes such as fluorescent proteins or antibiotic resistance markers. For transfection in cells, such as HEK cells, approximately 100-1000 ng, e.g., 100 . . . 200 . . . 300 . . . 400 . . . 500 . . . 600 . . . 700 . . . 800 . . . 900 . . . 1000 ng or any integer between these values, of a typical size donor plasmid (e.g., approximately 5 kb) containing a sgRNA/Cas9 vector, can be used for one well in 24-well plate. (See, e.g., Yang et al., "One Step Generation of Mice Carrying Reporter and Conditional Alleles by CRISPR/Cas-Mediated Genome Engineering" Cell (2013) 154:1370-1379).

Single-stranded and partially double-stranded oligonucleotides, such as DNA oligonucleotides, have been used in place of targeting plasmids for short modifications (e.g., less than 50 bp) within a defined locus without cloning. To achieve high HDR efficiencies, single-stranded oligonucleotides containing flanking sequences on each side that are homologous to the target region can be used, and can be oriented in either the sense or antisense direction relative to the target locus. The length of each arm can vary in length, but the length of at least one arm is typically longer than about 10 bases, such as from 10-150 bases, e.g., 10 . . . 20 . . . 30 . . . 40 . . . 50 . . . 60 . . . 70 . . . 80 . . . 90 . . . 100 . . . 110 . . . 120 . . . 130 . . . 140 . . . 150, or any integer within these ranges. However, these numbers can vary, depending on the size of the donor polynucleotide and the target polynucleotide. In a preferred embodiment, the length of at least one arm is 10 bases or more. In other embodiments, the length of at least one arm is 20 bases or more. In yet other embodiments, the length of at least one arm is 30 bases or more. In some embodiments, the length of at least one arm is less than 100 bases. In further embodiments, the length of at least one arm is greater than 100 bases. In some embodiments, the length of at least one arm is zero bases. For single-stranded DNA oligonucleotide design, typically an oligonucleotide with around 100-150 bp total homology is used. The mutation is introduced in the middle, giving 50-75 bp homology arms for a donor designed to be symmetrical about the target site. In other cases, no homology arms are required, and the donor polynucleotide is inserted using non-homologous DNA repair mechanisms.

In one embodiment, the methods described herein are useful for increasing Cas9-mediated engineering efficiency by modulating off-target genome editing events, e.g., by decreasing the number of double-stranded breaks in DNA in unintended and/or incorrect locations. In particular, genome engineering systems, such as those using zinc-finger nucleases (ZFNs), TALE-nucleases, and bacterially, derived RNA-guided nucleases (e.g., the CRISPR-Cas9 system), have been used to target a protein to a specific genomic locus where it can induce a DNA double-stranded break. DNA double-stranded breaks can be repaired through either non homologous end joining (NHEJ) or homology-directed repair (HDR). NHEJ can result in imperfect repair and the addition or deletion of several bases, whereas HDR can be utilized to insert rationally designed exogenous DNA sequences. These methods can sometimes result in off-target nuclease activity as described above.

Methods for increasing specificity and/or reducing off-target genomic events have included the use of shorter guide sequences with enhanced specificity (Fu, Y. et. al., "Improving CRISPR-Cas nuclease specificity using truncated guide RNAs," Nat Biotechnol. (2014) 32:279-284) and/or engineering Cas9 mutants that can use two independent targeting events to induce a double-stranded break (Ran, F. A, et al., "Double nicking by RNA-guided CRISPR Cas9 for enhanced genome editing specificity," Cell (2013) 154: 1380-1389; Tsai, S. Q., et al., "Dimeric CRISPR RNA-guided FokI nucleases for highly specific genome editing," Nature Biotech. (2014) 32:569-576). However, these strategies may reduce the efficiency of on-target genome editing, constrain targeting capabilities, or still result in "off-target" nuclease activity.

Accordingly, an embodiment of the present invention provides methods to mitigate off-target genome editing events in a cell population or in an in vitro biochemical reaction. Mitigation of such events can be performed by an engineered CRISPR-Cas9 system as described herein. The methods include at least two basic components: (1) a complex of a catalytically active Cas9 protein and a sgRNA that targets the intended nucleic acid target (sgRNA/Cas9 complex); and (2) a complex of a catalytically inactive Cas9 protein, termed "dCas9" herein and a sgRNA that targets off-target loci (sgRNA/dCas9 complex). In some embodiments, rather than a sgRNA/Cas9 complex, the first component can be any site-directed catalytically active DNA endonuclease, such as but not limited to zinc-finger nucleases (ZFNs), TALE-nucleases, and the like.

An off-target nucleic acid can differ from a target nucleic acid by, e.g., at least 1-5, such as 1, 2, 3, 4, 5 nucleotides, or up to 10 or more nucleotides or any number of nucleotides within the stated ranges.

The percent complementarity between an off-target nucleic acid locus (or surrounding genomic region) and an "on-target" nucleic acid-targeting nucleic acid can be, for example about 5% to about 100%, or any percentage between this range, more preferably in the range of 90-100%.

A number of catalytically active Cas9 proteins are known in the art and, as explained above, a Cas9 protein for use herein can be derived from any bacterial species, subspecies or strain that encodes the same. Although the subject invention is exemplified using S. pyogenes Cas9, orthologs from other bacterial species will find use herein. The specificity of these Cas9 orthologs is well known. Also useful are proteins encoded by Cas9-like synthetic proteins, and variants and modifications thereof. As explained above, the sequences for hundreds of Cas9 proteins are known and any of these proteins will find use with the present methods. The appropriate Cas9 protein to use with a particular target nucleic acid can be readily determined by one of skill in the art.

dCas9 proteins are also known and, as described above, these proteins can be made catalytically inactive by mutating the RuvC1 and/or HNH domains to eliminate nuclease function. This is typically accomplished by introducing point mutations in both of the two catalytic residues (D10A and H840A, numbered relative to S. pyogenes Cas9) of the gene encoding Cas9. In doing so, dCas9 is rendered unable to cleave double-stranded DNA but retains the ability to target DNA. Moreover, as with the Cas9 proteins, the dCas9 proteins can be derived from any bacterial species, subspecies or strain that encodes the same. Also useful are proteins encoded by Cas9 orthologs, Cas9-like synthetic proteins, and variants and modifications thereof. In one embodiment, dCas9 orthologs are selected based on the particular protospacer adjacent motif (PAM) sequences present on the target nucleic acid. For example, S. pyogenes Cas9 targets NGG sequences. However, if other PAM sequences are present, dCas9 orthologs can be used to target these sequences to block Cas9 cleavage thereof and prevent off-target breaks.

In the following embodiments, sgRNA is used as an exemplary guide polynucleotide, however, it will be recognized by one of skill in the art that other guide polynucleotides that site-specifically guide Cas9 or dCas9 to a target, or off-target, nucleic acid can be used. The sgRNA component of the complexes is responsible for targeting a particular nucleic acid target. In particular, the spacer region of the sgRNA includes the region of complementarity to the targeted nucleic acid sequence. Thus, the spacer is the polynucleotide sequence that can specifically hybridize to a target nucleic acid sequence. The spacer element interacts with the target nucleic acid sequence through hydrogen bonding between complementary base pairs. A spacer element binds to a selected nucleic acid target sequence. Accordingly, the spacer element is the DNA target-binding sequence.

Thus, binding specificity is determined by both sgRNA-DNA base pairing and the PAM sequence juxtaposed to the DNA complementary region.

Thus, in an aspect of the present invention, a sgRNA/dCas9 complex is targeted to genomic loci similarly targeted by catalytically intact sgRNA/Cas9 complexes, and can stably bind DNA and subsequently block activity of proteins targeted to those loci. In this way, dCas9 can robustly impair binding and/or activity of endogenous transcription factors in eukaryotic cells.

In an exemplary embodiment, a sgRNA, complexed with Cas9 (sgRNA/Cas9 complex) is directed to a genomic locus of interest to induce double-stranded breaks. The binding specificity is determined by both sgRNA-DNA base pairing and the PAM sequence juxtaposed to the DNA complementary region. Computational and/or experimental methods (e.g., sequencing, in silico DNA alignment methods can be used to ascertain off-target nuclease activity (e.g., to determine the off-target loci). Such methods are described in detail below. Independently acting dCas9 proteins can be designed to target these off-target loci. These engineered dCas9 proteins can be deployed as site-specific nuclease "blockers" to obstruct catalytically intact sgRNA/Cas9 binding and nuclease activity.

sgRNA/Cas9 and sgRNA/dCas9 blockers may be introduced, for example into a cell or tissue, at differing concentrations. For example, sgRNA/Cas9 and sgRNA/dCas9 complexes can be introduced at a ratio of 1:2, 1:3, 1:4, 1:5, 1:6, 1:7, 1:8, 1:9, 1:10, 10:1, 9:1, 8:1, 7:1, 6:1, 5:1, 4:1, 3:1, or 2:1. Additionally, all of these components, i.e., sgRNA, Cas9, dCas9, etc. may be provided separately, e.g., as separately in vitro assembled complexes, using separate DNA or RNA constructs, or together, in a single construct, or in any combination. Typically, the sgRNA components will complex with Cas9 and dCas9 when provided to a cell. Additionally, cell lines such as but not limited to HEK293 cells, are commercially available that constitutively express S. pyogenes Cas9 as well as S. pyogenes. Cas9-GFP fusions. In this instance, cells can be transfected without catalytically active Cas9 as such is provided by the host cell.

sgRNA/Cas9 and sgRNA/dCas9 complexes may be introduced at differing time points. For example, sgRNA/Cas9 and sgRNA/dCas9 complexes can be introduced at least 1 minute apart, 5 minutes apart, 10 minutes apart, 30 minutes apart, 1 hour apart, 5 hours apart, or 15 hours apart or more. sgRNA/Cas9 and sgRNA/dCas9 complexes can be introduced at most 1 minute apart, 5 minutes apart, 10 minutes apart, 30 minutes apart, 1 hour apart, 5 hours apart, or 15 hours apart or more. sgRNA/Cas9 complexes can be introduced before the sgRNA/dCas9 complexes. sgRNA/Cas9 complexes can be introduced after the sgRNA/dCas9 complexes. sgRNA/Cas9 complexes and sgRNA/dCas9 complexes may be differentially regulated (i.e. differentially expressed or stabilized) via exogenously supplied agents (e.g. inducible DNA promoters or inducible Cas9 proteins).

sgRNA/Cas9 and sgRNA/dCas9 complexes can be introduced into a cell by a variety of means including transfection, transduction, electroporation, micelles and liposome delivery, lipid nanoparticles, viral delivery, protein injection, and the like, described more fully below.

sgRNA/dCas9 complexes may be directed to genomic loci that partially overlap. For example, these complexes can be directed to loci that overlap by at least 1, 2, 3, 4, 5, 10, 15, 20, 25, 30, or 35 or more nucleotides. These complexes can be directed to loci that overlap by at most 1, 2, 3, 4, 5, 10, 15, 20, 25, 30, or 35 or more nucleotides.

sgRNA/dCas9 complexes can be directed adjacent to sites of observed off-target nuclease activity and Cas9 binding. For example, these complexes can be directed to sites that are adjacent to a site of observed off-target activity by at least 1, 2, 3, 4, 5, 10, 15, 20, 25, 30, or 35 or more nucleotides. Complexes can be directed to sites that are adjacent to a site of observed off-target activity by at most 1, 2, 3, 4, 5, 10, 15, 20, 25, 30, or 35 or more nucleotides.

Multiple sgRNA/dCas9 complexes may be used to "tile" a given locus for maximum nuclease blocking activity. In some instances, at least 1, 2, 3, 4, 5, 6, 7, 8, 9, or 10 or more sgRNA/dCas9 complexes are used. In some instances, at most 1, 2, 3, 4, 5, 6, 7, 8, 9, or 10 or more complexes are used. The complexes can cover a locus. Complexes can cover at least 5, 10, 15, 20, 25, 30, 35, 40, 45, 50, 55, 60, 65, 70, 75, 80, 85, 90, 95, or 100% of a locus. The complexes can cover at most 5, 10, 15, 20, 25, 30, 35, 40, 45, 50, 55, 60, 65, 70, 75, 80, 85, 90, 95, or 100% of a locus.

The blockers can reduce off-targeting binding of the active complexes by at least 10, 20, 30, 40, 50, 60, 70, 80, 90, or 100%. The blockers can reduce off-targeting binding of the active complexes by at most 10, 20, 30, 40, 50, 60, 70, 80, 90, or 100%.

Without wishing to be bound by a particular theory, a sgRNA/dCas9 complex can reduce binding of a sgRNA/Cas9 complex to an off-target nucleic acid by any mechanism. For example, the sgRNA/dCas9 complex can compete with the catalytically active complex for binding the off-target nucleic acid. The sgRNA/dCas9 complex can bind to the off-target nucleic acid, thereby creating steric hindrance for the sgRNA/Cas9 complex that prevents binding of the sgRNA/Cas9 complex to the off-target nucleic acid. The sgRNA/dCas9 complex can displace the sgRNA/Cas9 complex from the off-target nucleic acid. The sgRNA/dCas9 complex can inhibit the sgRNA/Cas9 complex from binding the off-target nucleic acid. The sgRNA/dCas9 complex can block the sgRNA/Cas9 complex from binding the off-target nucleic acid.

A sgRNA/dCas9 complex can reduce off-target nucleic acid binding, cleavage and/or modification by a sgRNA/Cas9 complex by 10%, 20%, 30%, 40%, 50%, 60%, 70%, 80%, 90%, or 100%, or any value within this range. Conversely, a sgRNA/dCas9 complex can increase site-specific binding, and/or modification by 10%, 20%, 30%, 40%, 50%, 60%, 70%, 80%, 90%, or 100%, or any value within this range.

Computational methods for determining off-target nuclease activity with any of the methods described herein can comprise scanning the genomic sequence of a subject. The genomic sequence can be segmented in silico into a plurality of nucleic acid sequences. The segmented nucleic acid sequences can be aligned with the nucleic acid-targeting nucleic acid sequence. A sequence search algorithm can determine one or more off-target nucleic acid sequences by identifying segmented genomic sequences with alignments comprising a defined number of base-pair mismatches with the nucleic acid-targeting nucleic acid. The number of base-pair mismatches between a genomic sequence and a nucleic acid-targeting nucleic acid selected by an algorithm can be user-defined, for example, the algorithm can be programmed to identify off-target sequences with mismatches of up to five base pairs between the genomic sequence and the nucleic acid-targeting nucleic acid. In silico binding algorithms can be used to calculate binding and/or cleavage efficiency of each predicted off-target nucleic acid sequence by a site-directed polypeptide using a weighting scheme. These data can be used to calculate off-target activity for a given nucleic acid-targeting nucleic acid and/or site-directed polypeptide.

Off-target binding activity can be determined by experimental methods. In one non-limiting example, the experimental methods can comprise sequencing a nucleic acid sample contacted by a complex comprising a site-directed polypeptide and a nucleic acid-targeting nucleic acid. The contacted nucleic acid sample can be fixed or crosslinked to stabilize the protein-RNA-DNA complex. The complex comprising the site-directed polypeptide, the nucleic acid (e.g., target nucleic acid, off-target nucleic acid), and/or the nucleic acid-targeting nucleic acid can be captured from the nucleic acid sample with an affinity tag and/or capture agents. Nucleic acid purification techniques can be used to separate the target nucleic acid from the complex. Nucleic acid purification techniques can include spin column separation, precipitation, and electrophoresis. The nucleic acid can be prepared for sequencing analysis by shearing and ligation of adaptors. Preparation for sequencing analysis can include the generation of sequencing libraries of the eluted target nucleic acid.

Sequence determination methods can include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeg™ technology by Illumina, Inc., San Diego, Calif., HeliScope™ by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), capillary sequencing (e.g, such as commercialized in MegaBACE by Molecular Dynamics, Inc., Sunnyvale, Calif.), electronic sequencing, single molecule sequencing (e.g., such as commercialized in SMRT™ technology by Pacific Biosciences, Menlo Park, Calif.), droplet microfluidic sequencing, sequencing by hybridization (such as commercialized by Affymetrix, Santa Clara, Calif.), bisulfite sequencing, and other known highly parallelized sequencing methods.

In some aspects, sequencing is performed by microarray analysis, such as in SNP genotyping by binding. Sequencing analysis can determine the identity and frequency of an off-target binding site for a given nucleic acid-targeting nucleic acid, by counting the number of times a particular binding site is read. The library of sequenced nucleic acids can include target nucleic acids and off-target nucleic acids.

Off-target binding activity can be determined by additional experimental methods. The experimental methods can comprise inserting a donor oligonucleotide into a cleaved site (Tsai, S. Q. et al., "GUIDE-seq enables genome wide profiling of off-target cleavage by CRISPR-Cas nucleases" Nature Biotech. (2015) 33:187-197). The genomic DNA is then fragmented, adapters are appended, and PCR is performed with primers complementary to the donor oligonucleotide and adapter sequences. The amplified sequences are sequenced and then mapped back to a reference genome. Other experimental methods rely on exploiting double-stranded break induced translocations of genomic DNA to experimentally induce (via the creation of double-stranded breaks) genomic "bait" sites (Frock, R. L. et. al. "Genome-wide detection of DNA double-stranded breaks induced by engineered nucleases" Nature Biotech. (2015) 33:179-186). Genomic DNA is subsequently fragmented; adapters are appended, and PCR is performed with primers complementary to the known "bait" site and adapter sequence. The amplified sequences are sequenced and then mapped back to a reference genome In some embodiments, Cas9 and/or dCas9 proteins may be modified or fused to additional protein domains. The fused additional protein domains may enhance the ability to block, impair, or inactivate active Cas9 complexes. Examples of fusion proteins including a Cas9 or dCas9 protein include, but are not limited to a nuclease, a transposase, a methylase, a transcription factor repressor or activator domain (e.g., such as KRAB and VP16), co-repressor and co-activator domains, DNA methyl transferases, histone acetyltransferases, histone deacetylases, and DNA cleavage domains (e.g., a cleavage domain from the endonuclease FokI). In some embodiments, a non-native sequence can confer new functions to the fusion protein. Such functions include, but are not limited to the following: methyltransferase activity, demethylase activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, glycosylase activity, acetyltransferase activity, deacetylase activity, kinase activity, phosphatase activity, ubiquitin ligase activity, deubiquitinating activity, adenylation activity, deadenylation activity, sumoylating activity, desumoylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, demyristoylation activity, and any combinations thereof.

In some instances, a donor polynucleotide is inserted into the target nucleic acid, when the target nucleic acid is cleaved. The methods can, for example, therefore be used to modify genomic DNA in a eukaryotic cell isolated from an organism. Further, the methods can also comprise contacting the nucleic acid target sequence in the genomic DNA with a donor polynucleotide wherein the modification comprises that at least a portion of the donor polynucleotide is integrated at the nucleic acid target sequence.

Donor polynucleotide insertion can be performed by the homologous recombination machinery of the cell. The donor polynucleotide may comprise homology arms that are partially or fully complementary to the regions of the target nucleic acid outside of the break point. Donor polynucleotide insertion can also be performed by non-homologous DNA repair machinery of the cell, where no homology arms are required. A discussion of donor polynucleotides is presented more fully below.

In an embodiment, the donor polynucleotide can be tethered to the sgRNA/dCas9 complex to position it near the cleavage site targeted by the active sgRNA/Cas9 complex. See, FIG. 7A. In this way, homology directed repair, as described below, can be achieved at higher rates.

One particular embodiment of the methods described herein is illustrated in FIGS. 4 and 5. FIG. 4 depicts an example of undesirable off-target binding and cleavage of a nuclease during genome engineering. A target nucleic acid 115 can be contacted with a complex comprising a site-directed polypeptide (e.g., Cas9) 105 and a nucleic acid-targeting nucleic acid (e.g., a sgRNA) 110. The complex comprising the Cas9 105 and sgRNA 110 can bind to a target nucleic acid 120. In some instances, the complex comprising the Cas9 105 and sgRNA 110 can bind to an off-target nucleic acid 125. In a cleavage step 130, the Cas9 of the complex can cleave 135 the target nucleic acid 120 and the off-target nucleic acid 125, thereby generating off-target effects.

FIG. 5 depicts an exemplary embodiment of reducing off-target binding and cleavage events using dCas9 blockers. A target nucleic acid 215 can be contacted with a complex comprising a site-directed polypeptide (e.g., Cas9) 205 and a nucleic acid-targeting nucleic acid (e.g., single-guide RNA) 210. The complex comprising the Cas9 205 and sgRNA 210 can bind to a target nucleic acid 220. In some instances, the complex comprising the Cas9 205 and sgRNA 210 can bind to an off-target nucleic acid 225. Complexes comprising an engineered dCas9 protein 235 and an engineered sgRNA 236 can be introduced and contacted 230 with the target nucleic acid. The dCas9 complexes can either displace or prevent the binding of complexes comprising active Cas9 205. The active Cas9 205 can cleave 240/245 the target nucleic acid 220. The active Cas9 205 may not cleave the off-target nucleic acid 225 because the dCas9 235 is preventing its binding and cleavage. In this way, off-target binding and cleavage may be prevented.

In another embodiment, the invention is directed to a method for increasing the efficiency of nucleic acid insertion by HDR or non-homologous repair mechanisms. As explained above, multiple repair pathways can compete at site-directed DNA breaks. Such breaks can be repaired through, for example, non-homologous end-joining (NHEJ) or homology-directed repair (HDR). NHEJ can result in imperfect repair and the addition or deletion of one or more bases, whereas HDR can be utilized to insert rationally designed exogenous DNA sequences. Repair of a double-strand break (DSB) in the presence of a donor polynucleotide results in a portion of breaks faithfully repaired by HDR and a portion of breaks where another less reliable repair pathway, such as NHEJ, is engaged, resulting in mixed repair outcomes. Alternative repair pathways for insertion of DNA using non-homologous mechanisms can also result in the insertion of donor DNA at the break site.

HDR relies on the presence of a donor polynucleotide, a piece of DNA that shares homology with sequences at or near a DNA break, that can be used to repair DNA breaks. Without wishing to be bound by any particular theory or mechanism, in some embodiments, the present invention provides for methods for using site-directed polypeptides (e.g., Cas9 nucleases) to create a substrate that will engage an alternative HDR pathway, similar to the single-strand annealing (SSA) branch of HDR, and will prevent competing DNA repair pathways, such as NHEJ, from repairing the break.

Single-strand annealing (SSA) is a process that is initiated when a break is introduced between two repetitive sequences oriented in the same direction. Four steps are generally necessary for the repair of breaks by SSA: (1) an end resection step which extends the repeated sequences and forms long 3'-ssDNA; (2) an annealing step in which the two repetitive sequences are annealed together forming a flap structure; (3) a second resection step in which the flap structures formed by the regions between the repeats are resected and; (4) ligation of the ends. HDR at DNA nicks occurs via a mechanism sometimes termed "alternative-HDR" that shares many of the same genetic dependencies of SSA such as inhibition by RAD51 and BRCA2.

The inventors herein have developed an engineered CRISPR system by generating at least two single-stranded nicks on the same strand of a target double-stranded nucleic acid and providing a donor polynucleotide that can anneal to the non-nicked strand. This results in the accurate insertion of exogenous DNA with little background mutagenic end-joining.

This method employs tandem Cas9 molecules that comprise one or more mutations that convert the catalytically active Cas9 molecules into nickases. The nickases are targeted to specific sites using sgRNAs designed to target two sites on the same strand in a double-stranded target nucleic acid, to generate two nicks (i.e., single-stranded breaks) on the targeted strand.

Any Cas9 molecule can be used, as described in detail above, so long as the Cas9 functions as a nickase. In some embodiments, this can be accomplished by introducing a point mutation in either of the two catalytic residues (D10A and H840A, numbered relative to S. pyogenes Cas9) of the gene encoding Cas9. An amino acid mutation at either position in Cas9 results in the inactivation of the nuclease catalytic activity and converts Cas9 to a nickase enzyme that makes single-stranded breaks at the target sites. The Cas9 double mutant with changes at amino acid positions D10A and H840A, however, completely inactivates both the nuclease and nickase activities. Targeting specificity is determined by complementary base-pairing of a sgRNA to the genomic loci which include PAM sequences adjacent thereto.

The nickases can comprise any mutation that enables the Cas9 to cleave only one strand of a double-stranded target nucleic acid. For example, as explained above, the Cas9 (e.g., Cas9 from S. pyogenes) can comprise a D10A mutation in one of its nuclease domains, or in a corresponding residue in an orthologous Cas9 to render the molecule a nickase. The Cas9 (e.g., Cas9 from S. pyogenes) can comprise a H840A mutation in one of its nuclease domains, or a corresponding residue in an orthologous Cas9 to render the molecule a nickase.

Accordingly, any Cas9 molecule that has nickase activity and only makes single-stranded breaks can be used. As explained above, Cas9 proteins are known and the Cas9 proteins can be derived from any bacterial species, subspecies or strain that encodes the same. Also useful are proteins encoded by Cas9 orthologs, Cas9-like synthetic proteins, and variants and modifications thereof. In one embodiment, Cas9 orthologs are selected timed on the particular protospacer adjacent motif (PAM) sequences present on the target nucleic acid. For example, S. pyogenes Cas9 targets NGG sequences. One of skill in the art can readily determine the particular Cas9 to mutate based on the particular specificity desired.

Moreover, the nickases used in the present methods should be paired such that nicks occur on the same strand. For example, both nickases used can include a D10A mutation, or both can include a H840A mutation. One nickase can be a S. pyogenes Cas9 nickase and the other can be a nickase that targets a PAM with a different adjacent sequence than targeted by the S. pyogenes Cas9 nickase, such as a nickase designed from an orthologous Cas9 protein, so long as the same strand is nicked. The appropriate nickases for use in the present methods are therefore based on the nucleic acid target sequence and on a determination of PAM-adjacent sequences present at the desired cleavage sites. In this way, the method provides flexibility for single-stranded cleavage of the target nucleic acid.

The nickases can cleave the sense strand of the double-stranded target nucleic acid or the anti-sense strand of the double-stranded target nucleic acid (e.g., DNA). The nickases can both cleave the same strand of the double-stranded target nucleic acid.

The two nickases can be designed to cleave at a distance of at least 10, 20, 30, 40, 50, 60, 70, 80, 90, or 100, 500, 1000, or 5000 or more bases away from each other. The two nickases can be designed to cleave at a distance of at most 10, 20, 30, 40, 50, 60, 70, 80, 90, or 100, 500, 1000, or 5000 or more bases away from each other. The distance between the nicks will determine the length of the donor polynucleotide to be provided for insertion.

As explained above, once the target nucleic acid is nicked, a donor polynucleotide can be directed to, and inserted into a target site of interest to modify the target nucleic acid. Targeted DNA modifications using donor polynucleotides for large changes (e.g., more than 100 bp insertions or deletions) traditionally use plasmid-based donor templates that contain homology arms flanking the site of alteration. Each arm can vary in length, but is typically longer than about 200 bp for large insertion, the size of the arms depending on the size of the donor polynucleotide and the target polynucleotide, as explained in detail above.

For shorter modifications (e.g., less than 50 bp), single-stranded oligonucleotides such as DNA oligonucleotides, partially double-stranded olignucleotides, nicked double-stranded donors, and the like, can be used in place of targeting plasmids. In this embodiment, for example, single-stranded oligonucleotides containing flanking sequences with homology in proximity to each nick, can be used, and can be oriented in either the sense or antisense direction relative to the target locus. For single-stranded DNA oligonucleotide design, typically an oligonucleotide with around 100-150 bp total homology is used. The mutation is introduced in the middle, giving approximately 50-75 bp homology arms. However, these numbers can vary, depending on the size of the donor polynucleotide and the target polynucleotide. Non-symmetrical polynucleotide donors can also be used that are composed of two DNA oligonucleotides. They are partially complementary, and each includes a flanking region of homology. For some modifications, the donor polynucleotide can have at least one arm with approximately 10 bases of homology to the target sequence. For some modifications, the donor polynucleotide can have at least one arm with less than 100 bases of homology to the target sequence. For other modifications, the donor can have more than 100 bases of homology to the target sequence. In some cases, the donor can have homology arms of the same length. In other cases, the donor can have homology arms of different lengths. In some cases, at least one of the homology arms is of zero length.

Thus, a donor polynucleotide can be designed to anneal to the single-stranded gap that results from the nicks made by the two nickases. As explained above, the donor polynucleotide can additionally comprise regions of homology with the sequences outside the breaks. The size of the regions of homology will be determined by the size of the target polynucleotide and can be at least 5, 10, 15, 20, 25, 30, 35 or more nucleotides in length, the size depending on the size of the donor polynucleotide and the target nucleic acid. The regions of homology can be at most 5, 10, 15, 20, 25, 30, 35 or more nucleotides in length. The donor polynucleotide can be single-stranded. The single-stranded donor polynucleotide can be inserted into the break created by the two tandem nickases.

FIG. 6 depicts an exemplary embodiment of the present methods. Here, two Cas9 D10A nickases are used in tandem to excise a single-stranded region of DNA on the same strand of a target double-stranded nucleic acid. As shown in FIG. 6A, two Cas9 nickases (in this case S. pyogenes Cas9 nickases with D10A mutations in the HNH endonuclease domain) are targeted to two spaced-apart positions on the sense strand of a target polynucleotide using two sgRNA/Cas9 nickase complexes. Targeting is accomplished using a spacer sequence present in the sgRNA that has been designed to specifically target a complementary region of in the target nucleic acid sequence. Binding specificity is determined by both sgRNA-DNA base pairing and the PAM, in this case, NGG, juxtaposed to the DNA complementary region (see, e.g., Mojica F. J. et al., "Short motif sequences determine the targets of the prokaryotic CRISPR defence system" Microbiology (2009) 155:733-740; Shah S. A. et al., "Protospacer recognition motifs: mixed identities and functional diversity" RNA Biology (2013) 10:891-899; Jinek M. et al., "A programmable dual-RNA-guided DNA endonuclease in adaptive bacterial immunity" Science (2012) 337:816-821). The targeted single strand is then cleaved (FIG. 6B) and the donor, with overlapping flanking regions, inserted (FIG. 6C).

In another embodiment, the invention is directed to additional methods for increasing HDR. The current methodology for introducing a desired change into a gene includes transfecting, electroporating, or microinjecting a site-specific endonuclease and donor molecules into a cell or embryo and using passive diffusion to locate the donor molecules throughout the nucleus (Lin, S. et al. "Enhanced homology-directed human genome engineering by controlled timing of CRISPR/Cas9 delivery," eLife (2014) December; doi: 10.7554/eLife.04766). However, this method of HDR typically has low efficiency. Unlike passive diffusion, the methods described below position the donor molecule near the cut site to increase HDR efficiency.

In these methods, one or more sgRNA/dCas9 complexes are used, along with a catalytically active sgRNA/Cas9 complex. The one or more sgRNA/dCas9 complexes include a polynucleotide donor associated therewith to position the donor polynucleotide near a target site in order to increase HDR efficiency. Thus, the tethered dCas9 can position the donor molecule in an orientation that will increase the likelihood that the donor molecule will be incorporated into the target site through HDR, thereby introducing a desired change to the target sequence.

As explained above, the donor polynucleotide can be double- or single-stranded DNA, RNA, a vector, plasmid, or the like and can be used to transfer genetic information (i.e., polynucleotide sequences) from the donor at the site of the break in the target nucleic acid. The donor can be used to insert or replace polynucleotide sequences in a target sequence, for example, to introduce a polynucleotide that encodes a protein or functional RNA (e.g., siRNA), to introduce a protein tag, to modify a regulatory sequence of a gene, or to introduce a regulatory sequence to a gene (e.g. a promoter, an enhancer, an internal ribosome entry sequence, a start codon, a stop codon, a localization signal, or polyadenylation signal), to modify a nucleic acid sequence (e.g., introduce a mutation), and the like.

Figure 7A:
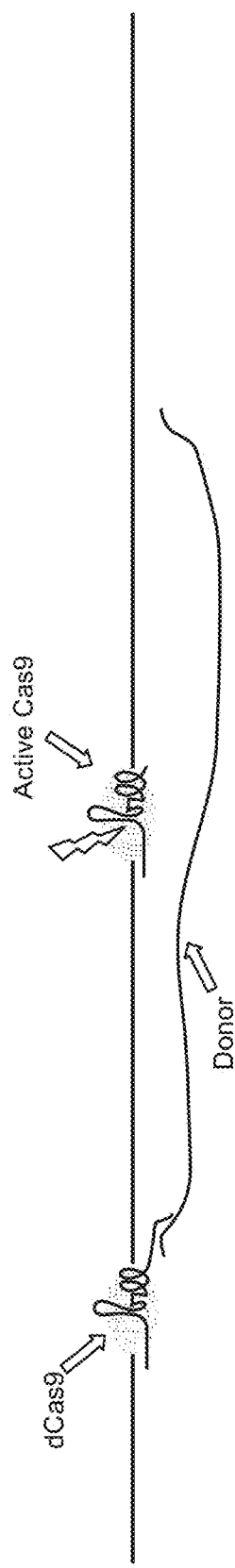
FIG. 7A and FIG. 7B depict methods of increasing HDR using sgRNA/dCas9 and catalytically active sgRNA/Cas9 complexes.
Figure 7B:
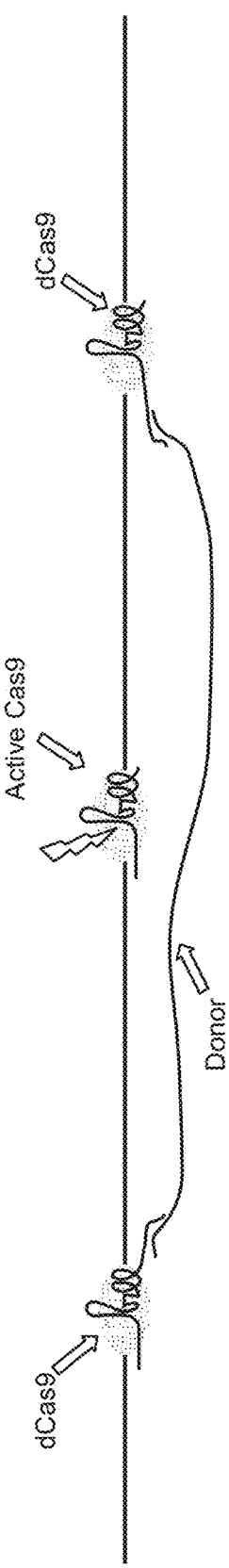

A single sgRNA/dCas9 complex can be used with the associated donor, as shown in FIG. 7A. Alternatively, two such complexes can be used to position the donor across the cut site as shown in FIG. 7B. The dCas9 and Cas9 molecules and guide polynucleotides used in the complexes can be any of those as described above.

When one sgRNA/dCas9 complex is used, the complex can target nucleic acid either upstream or downstream of the nucleic acid targeted by the catalytically active sgRNA/Cas9 complex. A donor polynucleotide is associated with the sgRNA/dCas9 complex. In this way, the donor polynucleotide is brought into proximity with the cleaved target nucleic acid and HDR will insert at least a portion of the donor polynucleotide at the cleaved site.

When two sgRNA/dCas9 complexes are used, the second sgRNA/dCas9 complex is designed to target nucleic acid downstream of the catalytically active sgRNA/Cas9 complex when the first sgRNA/dCas9 targets nucleic acid upstream of the catalytically active sgRNA/Cas9 complex. Alternatively, the second sgRNA/dCas9 complex is designed to target nucleic acid upstream of the catalytically active sgRNA/Cas9 complex when the first sgRNA/dCas9 targets nucleic acid downstream of the catalytically active sgRNA/Cas9 complex. Thus, the target for the active sgRNA/Cas9 complex is in a position between the two inactive complexes. Additionally, the 5' end of the polynucleotide donor will be associated with one of the inactive sgRNA/dCas9 complexes and the 3' end associated with the other of the inactive complexes such that the polynucleotide donor is positioned across the cleavage site for insertion using HDR. One of skill in the art can readily determine which end of the polynucleotide donor to associate with each complex based on the desired target.

The donor is tethered to the complexes using methods well known in the art. To do so, the backbone of the sgRNA can be extended to include a region complementary to the donor molecule. For example, the sgRNA in the sgRNA/dCas9 complex can include a number of extra nucleotides, e.g., 5-20, such as 5, 6, 7, 8, 9, 10, 11, 12, 13, 14, 15, 16, 17, 18, 19, 20 or even more, extra nucleotides at the 3' end of the sgRNA that will bind in a complementary fashion to the 5' or 3' end of a single-stranded DNA donor polynucleotide. In this manner, the donor polynucleotide will be positioned to interact with the sgRNA/Cas9-induced cut site and the cell's endogenous HDR machinery will incorporate the donor into the cleavage site. The sgRNA/dCas9 tethered donor polynucleotide is positioned upstream or downstream of the double-stranded break and is available at a higher local concentration for HDR.

In all of the embodiments of the above-described methods, the various components can be provided to a cell or in vitro, for example, using expression cassettes encoding a Cas9, a dCas9, sgRNA; a donor polynucleotide, etc. These components can be present on a single cassette or multiple cassettes, in the same or different constructs. Expression cassettes typically comprise regulatory sequences that are involved in one or more of the following: regulation of transcription, post-transcriptional regulation, and regulation of translation. Expression cassettes can be introduced into a wide variety of organisms including bacterial cells, yeast cells, plant cells, and mammalian cells. Expression cassettes typically comprise functional regulatory sequences corresponding to the organism(s) into which they are being introduced.

In one aspect, all or a portion of the various components of the methods are provided in vectors, including expression vectors, comprising polynucleotides coding for a Cas9, a dCas9, a sgRNA and/or a donor polynucleotide. Vectors useful for practicing the present invention include plasmids, viruses (including phage), and Integra table DNA fragments (i.e., fragments integratable into the host genome by homologous recombination). A vector replicates and functions independently of the host genome, or may, in some instances, integrate into the genome itself. Suitable replicating vectors will contain a replicon and control sequences derived from species compatible with the intended expression host cell. Transformed host cells are cells that have been transformed or transfected with the vectors constructed using recombinant DNA techniques General methods for construction of expression vectors are known in the art. Expression vectors for most host cells are commercially available. There are several commercial software products designed to facilitate selection of appropriate vectors and construction thereof, such as insect cell vectors for insect cell transformation and gene expression in insect cells, bacterial plasmids for bacterial transformation and gene expression in bacterial cells, yeast plasmids for cell transformation and gene expression in yeast and other fungi, mammalian vectors for mammalian cell transformation and gene expression in mammalian cells or mammals, viral vectors (including retroviral, lentiviral, and adenoviral vectors) for cell transformation and gene expression and methods to easily enable cloning of such polynucleotides. SnapGene™ (GSL Biotech LLC, Chicago, Ill.; snapgene.com/resources/plasmid_files/your_time_is_valuable/), for example, provides an extensive list of vectors, individual vector sequences, and vector maps, as well as commercial sources for many of the vectors.

Expression cassettes typically comprise regulatory sequences that are involved in one or more of the following: regulation of transcription, post-transcriptional regulation, and regulation of translation. Expression cassettes can be introduced into a wide variety of organisms including bacterial cells, yeast cells, mammalian cells, and plant cells. Expression cassettes typically comprise functional regulatory sequences corresponding to the host cells or organism(s) into which they are being introduced. Expression vectors can also include polynucleotides encoding protein tags (e.g., poly-His tags, hemagglutinin tags, fluorescent protein tags, bioluminescent tags, nuclear localization tags). The coding sequences for such protein tags can be fused to the coding sequences or can be included in an expression cassette, for example, in a targeting vector.

In some embodiments, polynucleotides encoding one or more of the various components are operably linked to an inducible promoter, a repressible promoter, or a constitutive promoter.

Several expression vectors have been designed for expressing guide polynucleotides. See, e.g., Shen, B. et al. "Efficient genome modification by CRISPR-Cas9 nickase with minimal off-target effects" (2014) Mar. 2. doi: 10.1038/nmeth.2857.10.1038/nmeth.2857. Additionally, vectors and expression systems are commercially available, such as from New England Biolabs (Ipswich, Mass.) and Clontech Laboratories (Mountain View, Calif.). Vectors can be designed to simultaneously express a target-specific sgRNA using a U2 or U6 promoter, a Cas9 and/or dCas9, and if desired, a marker protein, for monitoring transfection efficiency and/or for further enriching/isolating transfected cells by flow cytometry.

Vectors can be designed for expression of various components of the described methods in prokaryotic or eukaryotic cells. Alternatively, transcription can be in vitro, for example using T7 promoter regulatory sequences and T7 polymerase. Other RNA polymerase and promoter sequences can be used.

Vectors can be introduced into and propagated in a prokaryote. Prokaryotic vectors are well known in the art. Typically a prokaryotic vector comprises an origin of replication suitable for the target host cell (e.g., oriC derived from *E. coli*, pUC derived from pBR322, pSC101 derived from *Salmonella*), 15A origin (derived from p15A) and bacterial artificial chromosomes). Vectors can include a selectable marker (e.g., genes encoding resistance for ampicillin, chloramphenicol, gentamicin, and kanamycin). Zeocin™ (Life Technologies, Grand Island, N.Y.) can be used as a selection in bacteria, fungi (including yeast), plants and mammalian cell lines. Accordingly, vectors can be designed that carry only one drug resistance gene for Zeocin for selection work in a number of organisms. Useful promoters are known for expression of proteins in prokaryotes, for example, T5, T7, Rhamnose (inducible), Arabinose (inducible), and PhoA (inducible). Further, T7 promoters are widely used in vectors that also encode the T7 RNA polymerase. Prokaryotic vectors can also include ribosome binding sites of varying strength, and secretion signals (e.g., mal, sec, tat, ompC, and pelB). In addition, vectors can comprise RNA polymerase promoters for the expression of sgRNAs. Prokaryotic RNA polymerase transcription termination sequences are also well known (e.g., transcription termination sequences from *S. pyogenes*).

Integrating vectors for stable transformation of prokaryotes are also known in the art (see, e.g., Heap, J. T., et al., "Integration of DNA into bacterial chromosomes from plasmids without a counter-selection marker," Nucleic Acids Res. (2012) 40:e59).

Expression of proteins in prokaryotes is typically carried out in *Escherichia coli* with vectors containing constitutive or inducible promoters directing the expression of either fusion or non-fusion proteins.

A wide variety of RNA polymerase promoters suitable for expression of the various components are available in prokaryotes (see, e.g., Jiang, Y., et al., "Multigene editing in the *Escherichia coli* genome via the CRISPR-Cas9 system," Environ Microbiol. (2015) 81:2506-2514); Estrem, S. T., et al., (1999) "Bacterial promoter architecture: subsite structure of UP elements and interactions with the carboxy-terminal domain of the RNA polymerase alpha subunit," Genes Dev. 15; 13(16):2134-47).

In some embodiments, a vector is a yeast expression vector comprising one or more components of the above-described methods. Examples of vectors for expression in *Saccharomyces cerivisae* include, but are not limited to, the following: pYepSec1, pMFa, pJRY88, pYES2, and picZ. Methods for gene expression in yeast cells are known in the art (see, e.g., Methods in Enzymology, Volume 194, "Guide to Yeast Genetics and Molecular and Cell Biology, Part A," (2004) Christine Guthrie and Gerald R. Fink (eds.), Elsevier Academic Press, San Diego, Calif.). Typically, expression of protein-encoding genes in yeast requires a promoter operably linked to a coding region of interest plus a transcriptional terminator. Various yeast promoters can be used to construct expression cassettes for expression of genes in yeast. Examples of promoters include, but are not limited to, promoters of genes encoding the following yeast proteins: alcohol dehydrogenase 1 (ADH1) or alcohol dehydrogenase 2 (ADH2), phosphoglycerate kinase (PGK), triose phosphate isomerase (TPI), glyceraldehyde-3-phosphate dehydrogenase (GAPDH; also known as TDH3, or triose phosphate dehydrogenase), galactose-1-phosphate uridyltransferase (GALT), UDP-galactose epimerase (GAL10), cytochrome ci (CYC1), acid phosphatase (PHO5) and glycerol-3-phosphate dehydrogenase gene (GPD1). Hybrid promoters, such as the ADH2/GAPDH, CYC1/GAL10 and the ADH2/GAPDH promoter (which is induced at low cellular-glucose concentrations, e.g., about 0.1 percent to about 0.2 percent) also may be used. In *S. pombe*, suitable promoters include the thiamine-repressed nmtl promoter and the constitutive cytomegalovirus promoter in pTL2M.

Yeast RNA polymerase III promoters (e.g., promoters from 5S, U6 or RPR1 genes) as well as polymerase III termination sequences are known in the art (see, e.g., www.yeastgenome.org; Harismendy, O., et al., (2003) "Genome-wide location of yeast RNA polymerase III transcription machinery," The EMBO Journal. 22(18):4738-4747.)

In addition to a promoter, several upstream activation sequences (UASs), also called enhancers, may be used to enhance polypeptide expression. Exemplary upstream activation sequences for expression in yeast include the UASs of genes encoding these proteins: CYC1, ADH2, GAL1, GALT, GAL10, and ADH2. Exemplary transcription termination sequences for expression in yeast include the termination sequences of the α-factor, CYC1, GAPDH, and PGK genes. One or multiple termination sequences can be used.

Suitable promoters, terminators, and coding regions may be cloned into E. coli-yeast shuttle vectors and transformed into yeast cells. These vectors allow strain propagation in both yeast and E. coli strains. Typically, the vector contains a selectable marker and sequences enabling autonomous replication or chromosomal integration in each host. Examples of plasmids typically used in yeast are the shuttle vectors pRS423, pRS424, pRS425, and pRS426 (American Type Culture Collection, Manassas, Va.). These plasmids contain a yeast 2 micron origin of replication, an E. coli replication origin (e.g., pMB1), and a selectable marker.

The various components can also be expressed in insects or insect cells. Suitable expression control sequences for use in such cells are well known in the art. In some embodiments, it is desirable that the expression control sequence comprises a constitutive promoter. Examples of suitable strong promoters include, but are not limited to, the following: the baculovirus promoters for the piO, polyhedrin (polh), p 6.9, capsid, UAS (contains a Ga14 binding site), Ac5, cathepsin-like genes, the B. mori actin gene promoter; Drosophila melanogaster hsp70, actin, α-1-tubulin or ubiquitin gene promoters, RSV or MMTV promoters, copia promoter, gypsy promoter, and the cytomegalovirus IE gene promoter. Examples of weak promoters that can be used include, but are not limited to, the following: the baculovirus promoters for the ie1, ie2, ieO, et1, 39K (aka pp31), and gp64 genes. If it is desired to increase the amount of gene expression from a weak promoter, enhancer elements, such as the baculovirus enhancer element, hr5, may be used in conjunction with the promoter.

For the expression of some of the components of the present invention in insects, RNA polymerase III promoters are known in the art, for example, the U6 promoter. Conserved features of RNA polymerase III promoters in insects are also known (see, e.g., Hernandez, G., (2007) "Insect small nuclear RNA gene promoters evolve rapidly yet retain conserved features involved in determining promoter activity and RNA polymerase specificity," Nucleic Acids Res. 2007 January; 35(1):21-34).

In another aspect, the various components are incorporated into mammalian vectors for use in mammalian cells. A large number of mammalian vectors suitable for use with the systems of the present invention are commercially available (e.g., from Life Technologies, Grand Island, N.Y.; NeoBiolab, Cambridge, Mass.; Promega, Madison, Wis.; DNA2.0, Menlo Park, Calif.; Addgene, Cambridge, Mass.).

Vectors derived from mammalian viruses can also be used for expressing the various components of the present methods in mammalian cells. These include vectors derived from viruses such as adenovirus, papovirus, herpesvirus, polyomavirus, cytomegalovirus, lentivirus, retrovirus, vaccinia and Simian Virus 40 (SV40) (see, e.g., Kaufman, R. J., (2000) "Overview of vector design for mammalian gene expression," Molecular Biotechnology, Volume 16, Issue 2, pp 151-160; Cooray S., et al., (2012) "Retrovirus and lentivirus vector design and methods of cell conditioning," Methods Enzymol. 507:29-57). Regulatory sequences operably linked to the components can include activator binding sequences, enhancers, introns, polyadenylation recognition sequences, promoters, repressor binding sequences, stem-loop structures, translational initiation sequences, translation leader sequences, transcription termination sequences, translation termination sequences, primer binding sites, and the like. Commonly used promoters are constitutive mammalian promoters CMV, EF1a, SV40, PGK1 (mouse or human), Ubc, CAG, CaMKIIa, and beta-Act. and others known in the art (Khan, K. H. (2013) "Gene Expression in Mammalian Cells and its Applications," Advanced Pharmaceutical Bulletin 3(2), 257-263). Further, mammalian RNA polymerase III promoters, including H1 and U6, can be used.

In some embodiments, a recombinant mammalian expression vector is capable of preferentially directing expression of the nucleic acid in a particular cell type (e.g., using tissue-specific regulatory elements to express a polynucleotide). Tissue-specific regulatory elements are known in the art and include, but are not limited to, the albumin promoter, lymphoid-specific promoters, neuron-specific promoters (e.g., the neurofilament promoter), pancreas-specific promoters, mammary gland-specific promoters (e.g., milk whey promoter), and in particular promoters of T cell receptors and immunoglobulins. Developmentally-regulated promoters are also encompassed, e.g., the murine hox promoters and the alpha-fetoprotein promoter.

Numerous mammalian cell lines have been utilized for expression of gene products including HEK 293 (Human embryonic kidney) and CHO (Chinese hamster ovary). These cell lines can be transfected by standard methods (e.g., using calcium phosphate or polyethyleneimine (PEI), or electroporation). Other typical mammalian cell lines include, but are not limited to: HeLa, U2OS, 549, HT1080, CAD, P19, NIH 3T3, L929, N2a, Human embryonic kidney 293 cells, MCF-7, Y79, SO-Rb50, Hep G2, DUKX-X11, J558L, and Baby hamster kidney (BHK) cells.

Methods of introducing polynucleotides (e.g., an expression vector) into host cells are known in the art and are typically selected based on the kind of host cell. Such methods include, for example, viral or bacteriophage infection, transfection, conjugation, electroporation, calcium phosphate precipitation, polyethyleneimine-mediated transfection, DEAE-dextran mediated transfection, protoplast fusion, lipofection, liposome-mediated transfection, particle gun technology, direct microinjection, and nanoparticle-mediated delivery.

As explained above, one aspect of the present invention provides methods of increasing Cas9-mediated genome engineering efficiency by either decreasing the number of off-target nucleic acid double-stranded breaks, and/or enhancing HDR of a cleaved target nucleic acid, thus modifying genomes using HDR. The present invention also includes methods of modulating in vitro or in vivo transcription using the various components and complexes described herein. In one embodiment, a sgRNA/dCas protein complex can repress gene expression by interfering with transcription when the sgRNA directs DNA target binding of the complex to the promoter region of the gene. Use of the complexes to reduce transcription also includes complexes wherein the dCas protein is fused to a known down regulator of a target gene (e.g., a repressor polypeptide). For example, expression of a gene is under the control of regulatory sequences to which a repressor polypeptide can bind. A guide polynucleotide can direct DNA target binding of a repressor protein complex to the DNA sequences encoding the regulatory sequences or adjacent the regulatory sequences such that binding of the repressor protein complex brings the repressor protein into operable contact with the regulatory sequences. Similarly, dCas9 can be fused to an activator polypeptide to activate or increase expression of a gene under the control of regulatory sequences to which an activator polypeptide can bind.

Another method of the present invention is the use of sgRNA/dCas9 complexes in methods to isolate or purify regions of genomic DNA (gDNA). In an embodiment of the method, a dCas protein is fused to an epitope (e.g., a FLAG® epitope, Sigma Aldrich, St. Louis, Mo.) and a sgRNA directs DNA target binding of a sgRNA/dCas9 protein-epitope complex to DNA sequences within the region of genomic DNA to be isolated or purified. An affinity agent is used to bind the epitope and the associated gDNA bound to the sgRNA/dCas9 protein-epitope complex.

The present invention also encompasses gene-therapy methods for preventing or treating diseases, disorders, and conditions using the various methods described herein. In one embodiment, a gene-therapy method uses the introduction of nucleic acid sequences into an organism or cells of an organism (e.g., patient) to achieve expression of components of the present invention to provide modification of a target function. For example, cells from an organism may be engineered, ex vivo, by (i) introduction of vectors comprising expression cassettes expressing the various components, (ii) direct introduction of sgRNA and/or donor polynucleotides and Cas9 and/or dCas9 proteins, or (iii) introduction of combinations of these components. The engineered cells are provided to an organism (e.g., patient) to be treated.

Examples of gene-therapy and delivery techniques for therapy are known in the art (see, e.g., Kay, M. A., (2011) "State-of-the-art gene-based therapies: the road ahead," Nature Reviews Genetics 12, 316-328; Wang, D., et al., (2014) "State-of-the-art human gene therapy: part I. Gene delivery technologies," Discov Med. 18(97):67-77; Wang, D., et al., (2014) "State-of-the-art human gene therapy: part II. Gene therapy strategies and clinical applications," Discov Med. 18(98):151-61; "The Clinibook: Clinical Gene Transfer State of the Art," Odile Cohen-Haguenauer (Editor), EDP Sciences (Oct. 31, 2012), ISBN-10: 2842541715).

In some aspects, components of the present invention are delivered using nanoscale delivery systems, such as nanoparticles. Additionally, liposomes and other particulate delivery systems can be used. For example, vectors including the components of the present methods can be packaged in liposomes prior to delivery to the subject or to cells derived therefrom, such as described in U.S. Pat. Nos. 5,580,859; 5,549,127; 5,264,618; 5,703,055, all incorporated herein by reference in their entireties. Lipid encapsulation is generally accomplished using liposomes which are able to stably bind or entrap and retain nucleic acid.

The methods described herein can also be used to generate non-human genetically modified organisms. Generally, in these methods expression cassettes comprising polynucleotide sequences of the various components, as well as a targeting vector are introduced into zygote cells to site-specifically introduce a selected polynucleotide sequence at a DNA target sequence in the genome to generate a modification of the genomic DNA. The selected polynucleotide sequence is present in the targeting vector. Modifications of the genomic DNA typically include, insertion of a polynucleotide sequence, deletion of a polynucleotide sequence, or mutation of a polynucleotide sequence, for example, gene correction, gene replacement, gene tagging, transgene insertion, gene disruption, gene mutation, mutation of gene regulatory sequences, and so on. In one embodiment of methods to generate non-human genetically modified organisms, the organism is a mouse. Generating transgenic mice involves five basic steps (Cho A., et al., "Generation of Transgenic Mice," Current protocols in cell biology, (2009); CHAPTER. Unit-19.11): (1) purifying a transgenic construct (e.g., expression cassettes comprising the various components of the various methods described herein, as well as a targeting vector); (2) harvesting donor zygotes; (3) microinjecting the transgenic construct into the mouse zygote; (4) implanting the microinjected zygotes into pseudo-pregnant recipient mice; and (5) performing genotyping and analysis of the modification of the genomic DNA established in founder mice.

In another embodiment of methods to generate non-human genetically modified organisms, the organism is a plant. Thus, the components described herein are used to effect efficient, cost-effective gene editing and manipulation in plant cells. It is generally preferable to insert a functional recombinant DNA in a plant genome at a non-specific location. However, in certain instances, it may be useful to use site-specific integration to introduce a recombinant DNA construct into the genome. Recombinant vectors for use in plant are known in the art. The vectors can include, for example, scaffold attachment regions (SARs), origins of replication, and/or selectable markers.

Methods and compositions for transforming plants by introducing a recombinant DNA construct into a plant genome includes any of a number of methods known in the art. One method for constructing transformed plants is microprojectile bombardment. *Agrobacterium*-mediated transformation is another method for constructing transformed plants. Alternatively, other non-*Agrobacterium* species (e.g., *Rhizobium*) and other prokaryotic cells that are able to infect plant cells and introduce heterologous nucleotide sequences into the infected plant cell's genome can be used. Other transformation methods include electroporation, liposomes, transformation using pollen or viruses, chemicals that increase free DNA uptake, or free DNA delivery by means of microprojectile bombardment. DNA constructs of the present invention may be introduced into the genome of a plant host using conventional transformation techniques that are well known to those skilled in the art (see, e.g., "Methods to Transfer Foreign Genes to Plants," Y Narusaka, et al., cdn.intechopen.com/pdfs-wm/30876.pdf).

While preferred embodiments of the present invention have been shown and described herein, it will be obvious to those skilled in the art that such embodiments are provided by way of example only. From the above description and the following Examples, one skilled in the art can ascertain essential characteristics of this invention, and without departing from the spirit and scope thereof, can make changes, substitutions, variations, and modifications of the invention to adapt it to various usages and conditions. Such changes, substitutions, variations, and modifications are also intended to fall within the scope of the present disclosure.

EXPERIMENTAL

Aspects of the present invention are further illustrated in the following Examples. Efforts have been made to ensure accuracy with respect to numbers used (e.g., amounts, concentrations, percent changes, etc.) but some experimental errors and deviations should be accounted for. Unless indicated otherwise, temperature is in degrees Centigrade and pressure is at or near atmospheric. It should be understood that these Examples, while indicating some embodiments of the invention, are given by way of illustration only.

The following examples are not intended to limit the scope of what the inventors regard as various aspects of the present invention.

I. Use of Catalytically Inactive Cas9 Proteins as Site Specific Nuclease Blockers The following examples 1-4 illustrate the use of a catalytically inactive Cas9 (i.e. "dead" Cas9 or dCas9) to reduce off-target nuclease activity in eukaryotic cells. Additionally, this example shows how one can identify a specific spacer sequence (for incorporation into a sgRNA or crRNA) that is effective at blocking nuclease off-target activity in eukaryotic cells. Where the term sgRNA or single-guide RNA is used, it is understood by one skilled in the art that other guide polynucleotide systems, such as a crRNA/tracrRNA dual-guide system, present an alternative means of guiding dCas9 to the targeted site.

Example 1

Production of dCas9 Nuclease Blocker and Cas9 Nuclease Components sgRNA components of dCas9 nuclease-blocker (dCas9-NB, i.e. a Cas9 lacking catalytic activity) ribonucleoprotein (RNP) complexes (also termed "sgRNA/dCas9 complex" herein) and catalytically active Cas9 nuclease RNP complexes (also termed "sgRNA/Cas9 complex" herein) were produced by in vitro transcription (e.g., T7 Quick High Yield RNA Synthesis Kit, New England Biolabs, Ipswich, Mass.) from double-stranded DNA templates incorporating a T7 promoter at the 5' end of the DNA sequence. Polymerase Chain Reaction (PCR) using 5' overlapping primers was used to assemble the double-stranded DNA templates for transcription of sgRNA components. The sgRNA components, templates and primers used are identified in Table 1. The sequences of the oligonucleotide primers used in the assembly are presented in Table 2.

TABLE 1

Overlapping Primers for Generation of dCas9-NB and Cas9 Nuclease sgRNA Component Templates

| Component | Target for DNA binding | Primers |
|---|---|---|
| Cas9 sgRNA | VEGFA | A, B, C, D, E |
| dCas9 sgRNA | AAVS1 | A, B, C, D, F |
| dCas9 sgRNA | VEGFA off-target A2 | A, B, C, D, G |
| dCas9 sgRNA | VEGFA off-target A3 | A, B, C, D, H |
| dCas9 sgRNA | VEGFA off-target A4 | A, B, C, D, I |
| dCas9 sgRNA | VEGFA off-target B1 | A, B, C, D, J |
| dCas9 sgRNA | VEGFA off-target B2 | A, B, C, D, K |
| dCas9 sgRNA | VEGFA off-target C1 | A, B, C, D, L |
| dCas9 sgRNA | VEGFA off-target C3 | A, B, C, D, M |
| dCas9 sgRNA | VEGFA off-target D2 | A, B, C, D, N |
| dCas9 sgRNA | VEGFA off-target D3 | A, B, C, D, O |

*DNA primer sequences are shown in Table 2

TABLE 2

DNA Primer Sequences Used

| | | |
|---|---|---|
| A | AAAAAAAGCACCGACTCGGTGCC | SEQ ID NO: 1 |
| B | AGTAATAATACGACTCACTATAG | SEQ ID NO: 2 |
| C | GTTTTAGAGCTAGAAATAGCAAGTTAAAATAAGGCTAGTCCGTTATCAAC | SEQ ID NO: 3 |
| D | AAAAAAAGCACCGACTCGGTGCCACTTTTTCAAGTTGATAACGGACTAGC | SEQ ID NO: 4 |
| E | TAATACGACTCACTATAGGGTGGGGGAGTTTGCTCCGTTTTAGAGCTAGAAATAGC | SEQ ID NO: 5 |
| F | TAATACGACTCACTATAGGGGCCACTAGGGACAGGATGTTTTAGAGCTAGAAATAGC | SEQ ID NO: 6 |
| G | TAATACGACTCACTATAGTGGAGGGAGTTTGCTCCTGGITTTAGAGCTAGAAATAGC | SEQ ID NO: 7 |
| H | TAATACGACTCACTATAGGACGGATTTGTGGGATGGAGMTAGAGCTAGAAATAGC | SEQ ID NO: 8 |
| I | TAATACGACTCACTATAGCAGGACATTCTGACACCCCGTTTTAGAGCTAGAAATAGC | SEQ ID NO: 9 |
| J | TAATACGACTCACTATAGGAGGCTCCCATCACGGGGGTTTTAGAGCTAGAAATAGC | SEQ ID NO: 10 |
| K | TAATACGACTCACTATAGTGGGGATCACAGGTTCCCCGTTTTAGAGCTAGAAATAGC | SEQ ID NO: 11 |
| L | TAATACGACTCACTATAGAGAGCTCTTCTGACTACAGGMTAGAGCTAGAAATAGC | SEQ ID NO: 12 |
| M | TAATACGACTCACTATAGGACCAAATGAGACCAGTCCGMTAGAGCTAGAAATAGC | SEQ ID NO: 13 |
| N | TAATACGACTCACTATAGCCCATTATGATAGGGAGGGTTTTAGAGCTAGAAATAGC | SEQ ID NO: 14 |
| O | TAATACGACTCACTATAGCTCCTGGGGATGGAAGGGCGTTTTAGAGCTAGAAATAGC | SEQ ID NO: 15 |

TABLE 2-continued

DNA Primer Sequences Used

| | | |
|---|---|---|
| P | CACTCTTTCCCTACACGACGCTCTTCCGATCTCCAGATGGCACAT TGTCAGA | SEQ ID NO: 16 |
| Q | GGAGTTCAGACGTGTGCTCTTCCGATCTCCTAGTGACTGCCGTCT GC | SEQ ID NO: 17 |
| R | GGAGTTCAGACGTGTGCTCTTCCGATCTacctggccATCATCCTTCTA | SEQ ID NO: 18 |
| S | CACTCTTTCCCTACACGACGCTCTTCCGATCTCAGCAGACCCACT GAGTCAA | SEQ ID NO: 19 |
| T | CAAGCAGAAGACGGCATACGAGATNNNNNNNNGTGACTGGAGT TCAGACGTGTGCTC | SEQ ID NO: 20 |
| U | AATGATACGGCGACCACCGAGATCTACACNNNNNNNNACACTCT TTCCCTACACGACG | SEQ ID NO: 21 |

The PCR reaction to assemble the sgRNA DNA template proceeded as follows: Three "internal" DNA primers (C, D, E-O, Table 2) were present at a concentration of 2 nM each. Two "outer" DNA primers (A, B, Table 2) corresponding to the T7 promoter and the 3'end of the RNA sequence were present at 640 nM to drive the amplification reaction. PCR reactions were performed using Kapa HiFi Hotstart™ PCR kit (Kapa Biosystems, Inc., Wilmington, Mass.) as per manufacturer's recommendation. PCR assembly reactions were carried out using the following thermal cycling conditions: 98° C. for 2 minutes, 35 cycles of 15 seconds at 98° C., 15 seconds at 62° C., 15 seconds at 72° C., and a final extension at 72° C. for 2 minutes.

Between approximately 0.25-0.5 µg of the DNA template for the sgRNA components were transcribed using T7 High Yield RNA synthesis Kit (New England Biolabs, Ipswich, Mass.) for approximately 16 hours at 37° C. Transcription reactions were DNAse I-treated (New England Biolabs, Ipswich, Mass.). The quality of the transcribed RNA was checked by capillary electrophoresis on a Fragment Analyzer (Advanced Analytical Technologies, Inc., Ames, Iowa). The Cas9 and dCas9-NB sgRNA component sequences were as follows:

TABLE 3

Cas9 and dCas9-NB sgRNA Component Sequences

| DNA target | RNA Sequence (5' to 3') |
|---|---|
| VEGFA | GGGUGGGGGGAGUUUGCUCCGUUUUAGAGCUAGAAAUAGCAAGUUA AAAUAAGGCUAGUCCGUUAUCAACUUGAAAAAGUGGCACCGAGUCGG UGCUUUUUUU (SEQ ID NO: 22) |
| AAVS1 | GGGGCCACUAGGGACAGGAUGUUUUAGAGCUAGAAAUAGCAAGUUAA AAUAAGGCUAGUCCGUUAUCAACUUGAAAAAGUGGCACCGAGUCGGU GCUUUUUUU (SEQ ID NO: 23) |
| VEGFA off-target A2 | GUGGAGGGAGUUUGCUCCUGGUUUUAGAGCUAGAAAUAGCAAGUUA AAAUAAGGCUAGUCCGUUAUCAACUUGAAAAAGUGGCACCGAGUCGG UGCUUUUUUU (SEQ ID NO: 24) |
| VEGFA off-target A3 | GGACGGAUUUGUGGGAUGGAGUUUUAGAGCUAGAAAUAGCAAGUUA AAAUAAGGCUAGUCCGUUAUCAACUUGAAAAAGUGGCACCGAGUCGG UGCUUUUUUU (SEQ ID NO: 25) |
| VEGFA off-target A4 | GCAGGACAUUCUGACACCCCGUUUUAGAGCUAGAAAUAGCAAGUUAA AAUAAGGCUAGUCCGUUAUCAACUUGAAAAAGUGGCACCGAGUCGGU GCUUUUUUU (SEQ ID NO: 26) |
| VEGFA off-target B1 | GGAGGCUCCCAUCACGGGGGUUUUAGAGCUAGAAAUAGCAAGUUAA AAUAAGGCUAGUCCGUUAUCAACUUGAAAAAGUGGCACCGAGUCGGU GCUUUUUUU (SEQ ID NO: 27) |
| VEGFA off-target B2 | GUGGGAUCACAGGUUCCCCGUUUUAGAGCUAGAAAUAGCAAGUUAA AAUAAGGCUAGUCCGUUAUCAACUUGAAAAAGUGGCACCGAGUCGGU GCUUUUUUU (SEQ ID NO: 28) |
| VEGFA off-target C1 | GAGAGCUCUUCUGACUACAGGUUUUAGAGCUAGAAAUAGCAAGUUAA AAUAAGGCUAGUCCGUUAUCAACUUGAAAAAGUGGCACCGAGUCGGU GCUUUUUUU (SEQ ID NO: 29) |
| VEGFA off-target C3 | GGACCAAAUGAGACCAGUCCGUUUUAGAGCUAGAAAUAGCAAGUUAA AAUAAGGCUAGUCCGUUAUCAACUUGAAAAAGUGGCACCGAGUCGGU GCUUUUUUU (SEQ ID NO: 30) |

TABLE 3-continued

Cas9 and dCas9-NB sgRNA Component Sequences

| DNA target | RNA Sequence (5' to 3') |
|---|---|
| VEGFA off-target D2 | GCCCAUUAUGAUAGGGAGGGGIRJUUAGAGCUAGAAAUAGCAAGUUA AAAUAAGGCUAGUCCGUUAUCAACUUGAAAAAGUGGCACCGAGUCGG UGCUUUUUUU (SEQ ID NO: 31) |
| VEGFA off-target D3 | GCUCCUGGGGAUUGGAAGGGCGUUUUAGAGCUAGAAAUAGCAAGUUA AAAUAAGGCUAGUCCGUUAUCAACUUGAAAAAGUGGCACCGAGUCGG UGCUUUUUUU (SEQ ID NO: 32) |

Protein components of Cas9 and dCas9-NB RNPs were expressed from bacterial expression vectors in *E. coli* (BL21 (DE3)) and purified using affinity, ion exchange and size exclusion chromatography according to methods described in Jinek et al., 2012. The coding sequence for *S. pyogenes* Cas9 included the two nuclear localization sequences (NLS) at the C-terminus. The dCas9 variant of NLS-tagged Cas9, in which active site residues from both nuclease domains were mutated (Jinek, et al., 2012), was prepared by introducing mutations into the coding sequence of *S. pyogenes* Cas9 by site directed mutagenesis (Q5 Site-directed Mutagenesis Kit, New England Biolabs, Ipswich, Mass.). This method for production of Cas9 and/or dCas9-NB RNPs can be applied to the production of other Cas9 and/or dCas9-NB RNPs as described herein.

Example 2

Deep Sequencing Analysis for Detection of Target Modifications in Eukaryotic Cells This example illustrates the use of a MiSeq Sequencer (Illumina, San Diego, Calif.) for deep sequencing analysis to evaluate and compare the DNA cleavage (as inferred from non-homologous end joining, or NHEJ) of selected Cas9 nuclease off-target sequences in the presence and absence of dCas9-NBs. In this example, Cas9 was directed by a specific sgRNA to a sequence (GGGTGGGGGGAGTTTGCTCCTGG, SEQ ID NO:82) within the human gene Vascular Endothelial Growth Factor A (VEGFA). dCas9 was directed towards an off-target, sequence (GGATGGAGGGAGTTTGCTCCTGG, SEQ ID NO:83) known to be targeted by Cas9 RNP nuclease off-target to prevent off-target cleavage as well as a sequence (GGGGCCACTAGGGACAGGATTGG, SEQ ID NO:84) within the control locus, Adeno-Associated Virus Integration Site 1 (AAVS1).

A. Transfection of Cas9/dCas9-NB RNPs:

To assemble Cas9 and dCas9 RNPs, 1.3 µl of sgRNA (corresponding to approximately 1-9 µg or approximately 25-250 pmol) were incubated for 2 minutes at 95° C. then allowed to equilibrate to room temperature for about 5 minutes. Subsequently, Cas9 and dCas9 were mixed with a corresponding sgRNA to form RNPs in reaction buffer (20 mM HEPES, pH 7.5, 100 mM KCL, 5 mM MgCl$_2$, 5% glycerol). 20 pmols Cas9 were combined with the target sgRNA, and 0 or 20 pmols of dCas9 were combined with off-target directed sgRNAs, and functional RNPs were assembled by incubating at 37° C. for 10 min. Finally, 20 pmols Cas9 RNP was combined with 0 (i.e. just the dCas9-NB sgRNA component) or 20 pmols dCas9 RNP immediately prior to transfection into cells. Experiments were performed in triplicate.

Cas9/dCas9-NB RNP complexes were transfected into K562 cells (ATCC, Manassas, Va.), using the Nucleofector® 96-well Shuttle System (Lonza, Allendale, N.J.) and the following protocol: RNP complexes were dispensed in a 5 µL final volume into individual wells of a 96-well plate. K562 cells suspended in media were transferred from culture flask to a 50 mL conical, cells were then pelleted by centrifugation for 3 minutes at 200×g, the culture medium aspirated and washed once with calcium and magnesium-free PBS. K562 cells were then pelleted by centrifugation for 3 minutes at 200×g, the PBS aspirated and cell pellet was resuspended in 10 mL of calcium and magnesium-free PBS.

K562 cells were counted using the Countess® II Automated Cell Counter (Life Technologies, Grand Island, N.Y.). 4.2×10$^7$ cells were transferred to a 50 ml tube and pelleted. The PBS was aspirated and the cells were resuspended in Nucleofector™ SF (Lonza, Allendale, N.J.) solution to a density of 1×10$^7$ cells/mL. 20 µL of the cell suspension were then added to individual wells containing 5 µL of RNP complexes and the entire volume was transferred to the wells of a 96-well Nucleocuvette™ Plate (Lonza, Allendale, N.J.). The plate was loaded onto the Nucleofector™ 96-well Shuttle™ (Lonza, Allendale, N.J.) and cells were nucleofected using the 96-FF-120 Nucleofector™ program (Lonza, Allendale, N.J.). Post-nucleofection, 80 µL Iscove's Modified Dulbecco's Media (IMDM, Life Technologies, Grand Island, N.Y.), supplemented with 10% FBS (Fisher Scientific, Pittsburgh, Pa.) and supplemented with penicillin and streptomycin (Life Technologies, Grand Island, N.Y.), was added to each well and 50 µL of the cell suspension was transferred to a 96-well cell culture plate containing 150 µL pre-warmed IMDM complete culture medium. The plate was then transferred to a tissue culture incubator and maintained at 37° C. in 5% CO$_2$ for approximately 48 hours.

Genomic DNA (gDNA) was isolated from K562 cells 48 hours after Cas9/dCas9-NB transfection using 50 µL QuickExtract DNA Extraction solution (Epicentre, Madison, Wis.) per well followed by incubation at 37° C. for 10 minutes. 50 µL water was added to the samples, and next they were incubated at 75° C. for 10 minutes and 95° C. for 5 minutes to stop the reaction. sgDNA was stored at −20° C. until further processing.

B. Sequencing Library Preparation:

Using previously isolated sgDNA, a first PCR was performed using Q5 Hot Start High-Fidelity 2× Master Mix (New England Biolabs, Ipswich, Mass.) at 1× concentration, primers at 0.5 µM each, 3.75 µL of sgDNA in a final volume of 10 µL and amplified 98° C. for 1 minutes, 35 cycles of 10 s at 98° C., 20 s at 60° C., 30 s at 72° C., and a final extension at 72° C. for 2 min. PCR reaction was diluted 1:100 in water. Target-specific primers are shown in Table 4:

TABLE 4

Target-specific Primers Used for Sequencing

| Target | Primers |
| --- | --- |
| VEGFA on-target | P, Q |
| VEGFA off-target 1 | R, S |

*DNA primer sequences are shown in Table 2

A second 'barcoding' PCR was set up using unique primers for each sample facilitating multiplex sequencing (oligonucleotides T and U in Table 2, where a unique 8 bp index sequence, denoted by "(SEQ ID NO:33)" allowed demultiplexing of each amplicon during sequence analysis).

The second PCR was performed using Q5 Hot Start High-Fidelity 2× Master Mix (New England Biolabs, Ipswich, Mass.) at 1× concentration, primers at 0.5 µM each, 1 µL of 1:100 diluted first PCR, in a final volume of 10 µL and amplified 98° C. for 1 minute, 12 cycles of 10 s at 98° C., 20 s at 60° C., 30 s at 72° C., and a final extension at 72° C. for 2 min. PCR reactions were pooled into a single microfuge tube for SPRIselect bead (Beckman Coulter, Pasadena, Calif.) based clean up of amplicons for sequencing.

To pooled amplicons, 0.9× volumes of SPRIselect beads were added, mixed and incubated at room temperature (RT) for 10 minutes. The microfuge tube was placed on a magnetic tube stand (Beckman Coulter, Pasadena, Calif.) until solution had cleared. Supernatant was removed and discarded, and the residual beads were washed with 1 volume of 85% ethanol, and incubated at RT for 30 s. After incubation, ethanol was aspirated and beads were air dried at RT for 10 min. The microfuge tube was then removed from the magnetic stand and 0.25× volumes of water (Qiagen, Venlo, Limburg) was added to the beads, mixed vigorously, and incubated for 2 min. at RT. The microfuge tube was spun in a microcentrifuge to collect the contents of the tube, and was then returned to the magnet, incubated until solution had cleared, and the supernatant containing the purified amplicons were dispensed into a clean microfuge tube. The purified amplicon library was quantified using the Nanodrop™ 2000 system (Thermo Fisher Scientific, Wilmington, Del.).

The amplicon library was normalized to 4 nM concentration as calculated from optical absorbance at 260 nm (Nanodrop™, Thermo Fisher Scientific, Wilmington, Del.) and size of the amplicons. Library was analyzed on MiSeq Sequencer with MiSeq Reagent Kit v2, 300 Cycles (Illumina, San Diego, Calif.), with two 151-cycle paired-end run plus two eight-cycle index reads.

C. Deep Sequencing Data Analysis:

The identity of products in the sequencing data was analyzed based upon the index barcode sequences adapted onto the amplicons in the second round of PCR. A computational script was used to process the MiSeq data by executing the following tasks:

1. Reads were aligned to the human genome (build GRCh38/38) using Bowtie (bowtie-bio.sourceforge.net/index.shtml) software.
2. Aligned reads were compared to wild type loci; reads not aligning to any part of the loci were discarded.
3. Reads matching wild-type sequence were tallied. Reads with indels (surrounding 5 bp from the Cas9 cut site) were categorized by indel type and tallied.
4. Total indel reads were divided by the sum of wild-type reads and indel reads to give percent-mutated reads.

Figure 8:
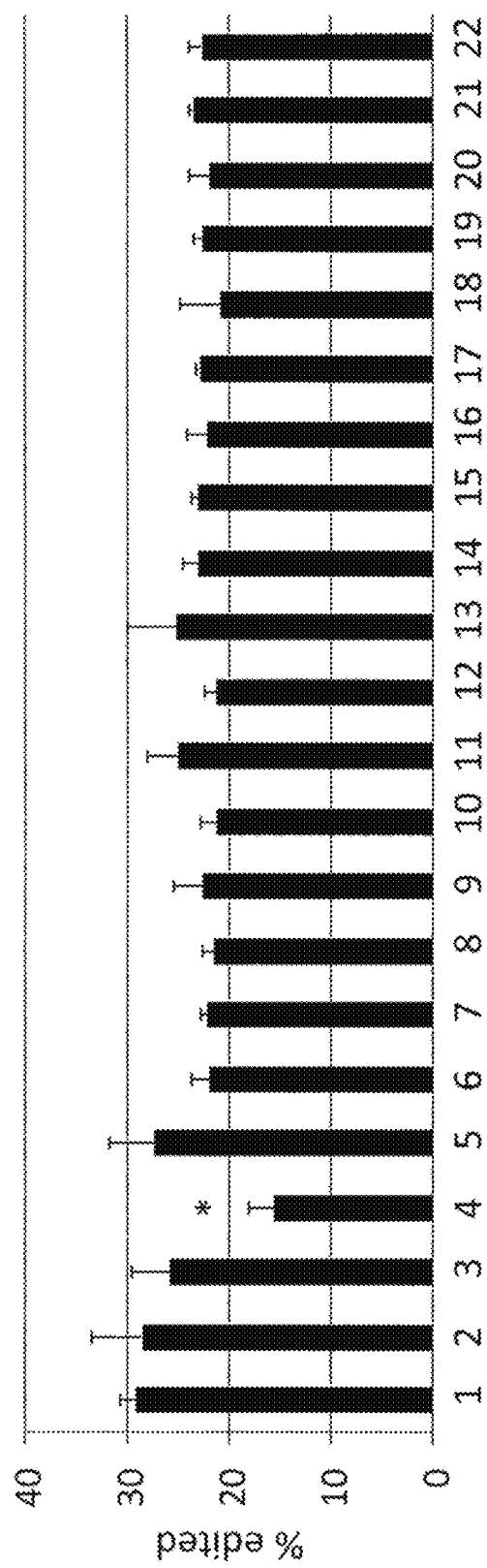
FIG. 8 shows the effects of dCas9 nuclease blockers (dCas9-NBs) on VEGFA sgRNA/Cas9 on-target editing at the VEGFA locus.

FIG. 8 shows the effects of dCas9-NBs on VEGFA sgRNA/Cas9 on-target editing at the VEGFA locus. As can be seen from the data in the figure, the addition of a dCas9-NB targeted to the VEGFA on-target locus inhibits on-target editing, while dCas9-NBs targeted to distinct regions do not have a significant effect (n=3, error bars show standard deviation, *p<0.05, student's t-test (two-tailed) comparing 3 vs. 4).

Figure 9:
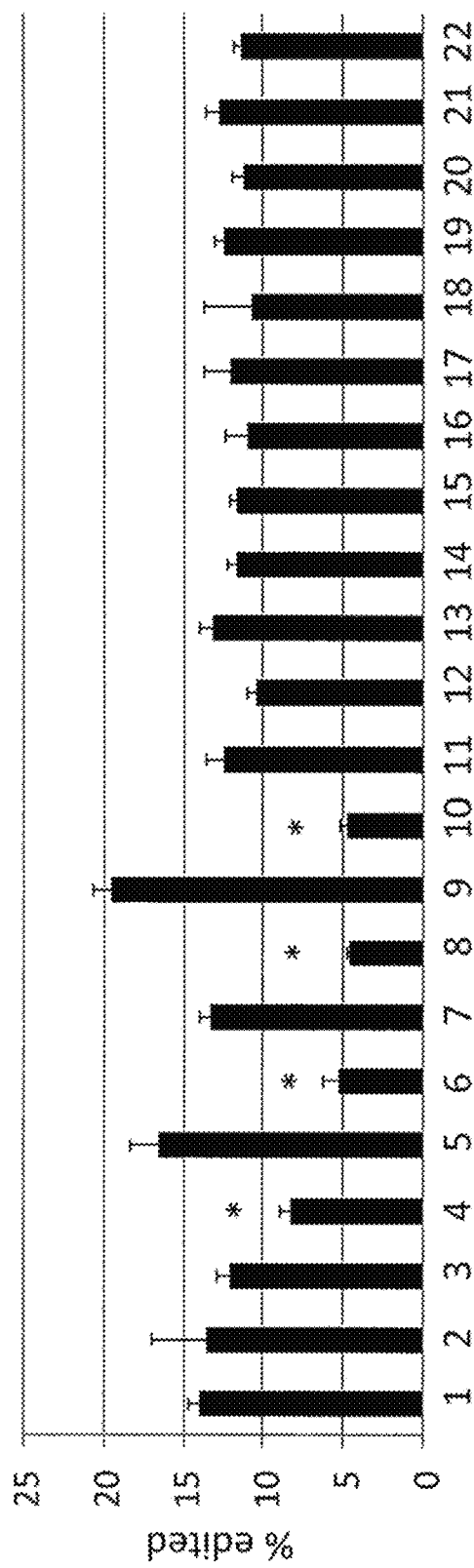
FIG. 9 shows the effects of dCas9-NBs on VEGFA sgRNA/Cas9 off-target editing at a known VEGFA off-target locus on human chromosome 15.

FIG. 9 shows the effects of dCas9-NBs on VEGFA sgRNA/Cas9 off-target editing at a known VEGFA off-target locus on human chromosome 15. As can be seen from the data in the figure, the addition of a dCas9-NB to the off-target locus either by the VEGFA on-target sgRNA or an sgRNA targeted specifically to the chromosome 15 off-target locus, impairs cleavage, while dCas9-NBs targeted to distinct regions do not have a significant effect (n=3, error bars show standard deviation, *p<0.05, student's t-test (two-tailed) comparing 3 vs. 4, 5 vs. 6, 7 vs. 8).

A description of the samples used in these experiments and FIGS. 8 and 9 are shown in Table 5:

TABLE 5

Sample Descriptions for FIGS. 8 and 9

| Sample | Description |
| --- | --- |
| 1 | AAVS1 sgRNA, 0 pmol dCas9 |
| 2 | AAVS1 sgRNA, 20 pmol dCas9 |
| 3 | VEGFA sgRNA, 0 pmol dCas9 |
| 4 | VEGFA sgRNA, 20 pmol dCas9 |
| 5 | VEGFA off-target sgRNA A2, 0 pmol dCas9 |
| 6 | VEGFA off-target sgRNA A2, 20 pmol dCas9 |
| 7 | VEGFA off-target sgRNA A3, 0 pmol dCas9 |
| 8 | VEGFA off-target sgRNA A3, 20 pmol dCas9 |
| 9 | VEGFA off-target sgRNA A4, 0 pmol dCas9 |
| 10 | VEGFA off-target sgRNA A4, 20 pmol dCas9 |
| 11 | VEGFA off-target sgRNA B1, 0 pmol dCas9 |
| 12 | VEGFA off-target sgRNA B1, 20 pmol dCas9 |
| 13 | VEGFA off-target sgRNA B2, 0 pmol dCas9 |
| 14 | VEGFA off-target sgRNA B2, 20 pmol dCas9 |
| 15 | VEGFA off-target sgRNA C1, 0 pmol dCas9 |
| 16 | VEGFA off-target sgRNA C1, 20 pmol dCas9 |
| 17 | VEGFA off-target sgRNA C3, 0 pmol dCas9 |
| 18 | VEGFA off-target sgRNA C3, 20 pmol dCas9 |
| 19 | VEGFA off-target sgRNA D2, 0 pmol dCas9 |
| 20 | VEGFA off-target sgRNA D2, 20 pmol dCas9 |
| 21 | VEGFA off-target sgRNA D3, 0 pmol dCas9 |
| 22 | VEGFA off-target sgRNA D3, 20 pmol dCas9 |

Following the guidance of the present specification and examples, the deep sequencing analysis described in this example can be practiced by one of ordinary skill in the art with other Cas9/dCas9 RNP complexes (i.e. assembled with distinct sgRNAs and/or distinct ratios of Cas9, dCas9, and sgRNA).

Example 3

Identification of Cas9 RNP Off-Target Loci

This example illustrates the method through which off-target Cas9 nuclease sites may be identified. The method presented here is adapted from Tsai et. al., "GUIDE-seq enables genome-wide profiling of off-target cleavage by CRISPR-Cas nucleases.," Nat Biotechnol., 2015 February; 33(2):187-97.

A. Identify a Target-Site of Interest:

A given locus in a genome of interest (i.e. a human genome) is screened using bioinformatics approaches known to those skilled in the art to identify Cas9 target-sites.

A 20 base pair target-site, followed by an NGG protospacer adjacent motif (PAM), is selected for nuclease targeting.

B. Assemble GUIDE-Seq Components:

Oligos are obtained (Integrated DNA Technologies, Coralville, Iowa) for generating a blunt, double-stranded oligodeoxynucleotide (dsODN) that will be utilized for the GUIDE-Seq method. The dsODN contains phosphothiorate linkages at the 5' ends of both DNA strands. The dsODN is assembled by incubating the two oligos in annealing buffer (i.e. 10 mM Tris, pH 7.5-8.0, 50 mM NaCl, 1 mM EDTA) for 3 min at 95° C. and allowing the oligos to cool to RT.

C. Transfection of GUIDE-Seq Components:

Cells from a species of interest (i.e., human cells) are procured from a commercial repository (i.e. ATCC, DSMZ). Cells are grown to an appropriate density for transfection. Cells are transfected with an sgRNAs/Cas9 protein complex and the DNA donor oligo via methods known to those skilled in the art (i.e. nucleofection or lipid transfection of DNA plasmid encoding RNP components as well as dsODN).

D. Sequencing Library Preparation and Analysis:

gDNA is harvested 48 hrs after cell transfection and purified using Agencourt DNAdvance (Beckman Coulter, Pasadena, Calif.). Purified gDNA is fragmented with methods known to those skilled in the art (i.e. mechanical shearing via sonication or enzymatic shearing with NEB-fragmentase, (New England Biolabs, Ipswich, Mass.)) to an average length of 500 base pairs, then end-repaired, A-tailed and ligated to adapters. PCR with primers complementary to the dsODN tag and illumina sequencing adapter sequences (Illumina, San Diego, Calif.), respectively, are used for target-enrichment. Target-enriched library is sequenced using MiSeq Sequencer (Illumina, San Diego, Calif.). Reads are mapped back to the respective species' genome and read coverage is calculated using BedTools (bedtools.readthedocs.org/en/latest/). Integrative Genomics Viewer (IGV, broadinstitute.org/igv/) is used to map the starting (5') and ending (3') position of reads, and peaks are called using MACS2 (pypi.python.org/pypi/MACS2). The Sequencing data is used to confirm that a putative genomic locus is a candidate off-target sequence. Following the guidance of the present examples, the identification of novel off-target loci can be practiced by one of ordinary skill in the art.

Example 4 dCas9 Off-Target Blocking with Truncated Single-Guide RNAs (Tru-gRNAs)

This example illustrates methods where dCas9-NBs may be assembled with truncated guides. The method presented here is adapted from Fu Y et. al., "Improving CRISPR-Cas nuclease specificity using truncated guide RNAs," Nat Biotechnol. 2014 March; 32(3):279-84. Truncated single-guide RNAs (tru-sgRNAs) of 17-18 nt have been shown to possess increased specificity relative to 20 nt sgRNAs. Thus, a dCas9-NB assembled with a tru-sgRNA may be targeted directly to a genomic motif and PAM of an off-target locus to reduce off-target editing while having minimal inhibition of on-target editing.

A. Design of tru-sgRNA to Enable dCas9 Mediated Off-Target Nuclease Blocking:

Using methods described in Example 3 herein, a given off-target genomic locus (i.e. spacer sequence) is identified. Next, a tru-sgRNA is designed to target said off-target location in the genome. The tru-sgRNA/dCas9 RNP may target a sequence contained entirely within the off-target motif, or it may target a sequence partially overlapping with the off-target motif.

B. Production of dCas9 Nuclease Blocker Components:

dCas9 is assembled with a short (i.e. 17 nt) tru-sgRNA and Cas9 is assembled with a sgRNA (i.e. 20 nt) to produce functional RNPs. RNA components are transcribed from DNA templates incorporating a T7 promoter at the 5' end as described in the Experimental section herein. dCas9 (D10A, H840A) and Cas9 proteins are recombinantly expressed in E. coli. RNPs are assembled by incubating protein and RNA components together at 37° C. for 10 minutes.

C. Transfection of Tru-sgRNA Containing dCas9-NB and sgRNA Containing Cas9 RNP:

Cells from species of interest are procured from a commercial repository (i.e. ATCC, DSMZ). Cells are grown to a level of confluency that enables transfection. tru-sgRNAs complexed with dCas9 are mixed with sgRNAs assembled with Cas9. Next, the mixture is transfected into a cell line of interest using methods known to those skilled in the art (i.e. nucleofection or lipid transfection) as described in Example 1 herein.

D. Sequencing Library Preparation:

gDNA is then harvested 48 hours later using Quick Extract (Epicentre, Madison, Wis.) per the manufacturer's instructions. Two rounds of PCR, as described in Example 1 herein, are used to amplify and barcode the genomic region targeted by the tru-sgRNA/dCas9-NB. Adapter oligos and dimers are removed by performing SPRIselect bead (Beckman Coulter, Pasadena, Calif.)-based clean up of the sequencing library. Sequencing library concentration is determined by the Nanodrop™ 2000 system (Thermo Scientific, Wilmington Del.).

E. Deep Sequencing Analysis:

The library is analyzed on MiSeq Sequencer as follows:
1. Reads are aligned to the human genome (build GRCh38/38) using Bowtie (bowtie-bio.sourceforge.net/index.shtml) software.
2. Aligned reads are compared to wild type loci; reads not aligning to any part of the loci are discarded.
3. Reads matching wild-type sequence are tallied. Reads with indels are categorized by indel type and tallied.
4. Total indel reads are divided by the sum of wild-type reads and indel reads are percent-mutated reads.

II. dCas9 Directed Positioning of Homology Directed Repair Donors

Example 5

Use of dCas9 to Position Homology Donor Nucleotides Near a Targeted Site for Increasing Homology Directed Repair (HDR) Efficiency This system consists of a site-specific endonuclease (e.g, Cas9 complexed with a sgRNA) that targets a DNA target sequence of interest), and one or more catalytically inactive dCas9 molecules complexed with a sgRNA that targets DNA sequences adjacent to the cut site (See FIGS. 7A and 7B). These dCas9 molecules are also tethered to a HDR molecule (i.e. dsDNA, ssDNA, RNA, a plasmid, or the like). The tethered dCas9 is used to position the donor molecule in an orientation that will increase the likelihood that the donor molecule will be incorporated into the target site through HDR, thereby introducing a desired change to the target sequence.

A. DNA and RNA Constructs:

Oligonucleotides are ordered from manufacturers (e.g., Integrated DNA Technologies, Coralville, Iowa; or Eurofins, Luxembourg). sgRNA transcription constructs are assembled by polymerase chain reaction (PCR).

The primers for sgRNA transcription constructs consist of a primer containing a 5' T7 promoter sequence, a primer containing a unique spacer sequence, primers containing the sgRNA TRCR backbone, and a reverse primer that may contain a complementary sequence to the homology donor for tethering the donor to the 3' end of the sgRNA.

T7 sgRNA transcription constructs are PCR-amplified. Two outer primers (forward oligo contains T7 promoter oligo; reverse oligos contain 3' end of sgRNA backbone or homology donor complementary sequence for tethering) are present in PCR reaction at 640 nM. Unique spacer and sgRNA backbone oligos are present at 2 nM. PCR reactions are performed using Q5 Hot Start High-Fidelity 2× Master Mix (New England Biolabs, Ipswich, Mass.) following manufacturer's recommendations. PCR T7 sgRNA transcription construct assembly PCR is carried out using the following thermal cycling conditions: 98° C. for 2 minutes, 29 cycles of 98° C. for 20 seconds, 62° C. for 20 seconds, and 72° C. for 15 seconds, followed by a final extension of 72° C. for 2 minutes. DNA constructs are evaluated by capillary electrophoresis (Fragment Analyzer, Advanced Analytical Technologies, Ames, Iowa).

RNA components are produced through in vitro transcription (T7 Quick High Yield RNA Synthesis Kit, New England Biolabs, Ipswich, Mass.) from a double-stranded DNA template. The RNA is then treated with DNase I (New England Biolabs, Ipswich, Mass.) to remove any double-stranded DNA and incubated at 37° C. for 10 minutes. 0.5 M EDTA is then added to the transcription reactions and incubated at 75° C. for 10 minutes to inactivate the DNase I.

Homology donors are ordered as single-stranded DNA oligos of approximately 90 nucleotides in length. The homology donors are complementary to the coding sequence and are designed to be centered on the cut site with the PAM replaced with a EcoR1 restriction enzyme site and homology arms of approximately 42 nucleotides in length matching the target sequence.

B. sgRNA/Cas9 and sgRNA/dCas9 Complex Generation:

*S. pyogenes* catalytically active Cas9 and catalytically inactive dCas9 are C-terminally tagged with two nuclear localization sequences (NLS) and recombinantly expressed in *E. coli*. All sgRNA and tethered sgRNA are incubated for 2 minutes at 95° C., removed from the thermal cycler and allowed to equilibrate to room temperature. Cas9 Ribonucleoprotein (RNP) complexes (also termed "sgRNA/Cas9 complex" and "sgRNA/dCas9 complex" herein) are set up in triplicate with 2 µM Cas9 or 2 µM dCas9, 6 µM sgRNA or 6 µM tethered sgRNA and 2 µM donor oligo in binding buffer (20 mM HEPES, 100 mM KCl, 5 mM $MgCl_2$, 1 mM DTT, and 5% glycerol at pH 7.4) in a volume of 6 µl. The RNPs are then allowed to bind at 37° C. for 10 minutes. After annealing, the Cas9 RNP and dCas9 RNP-donor tethers can be combined to a final volume of 12 µl.

Figure 10:
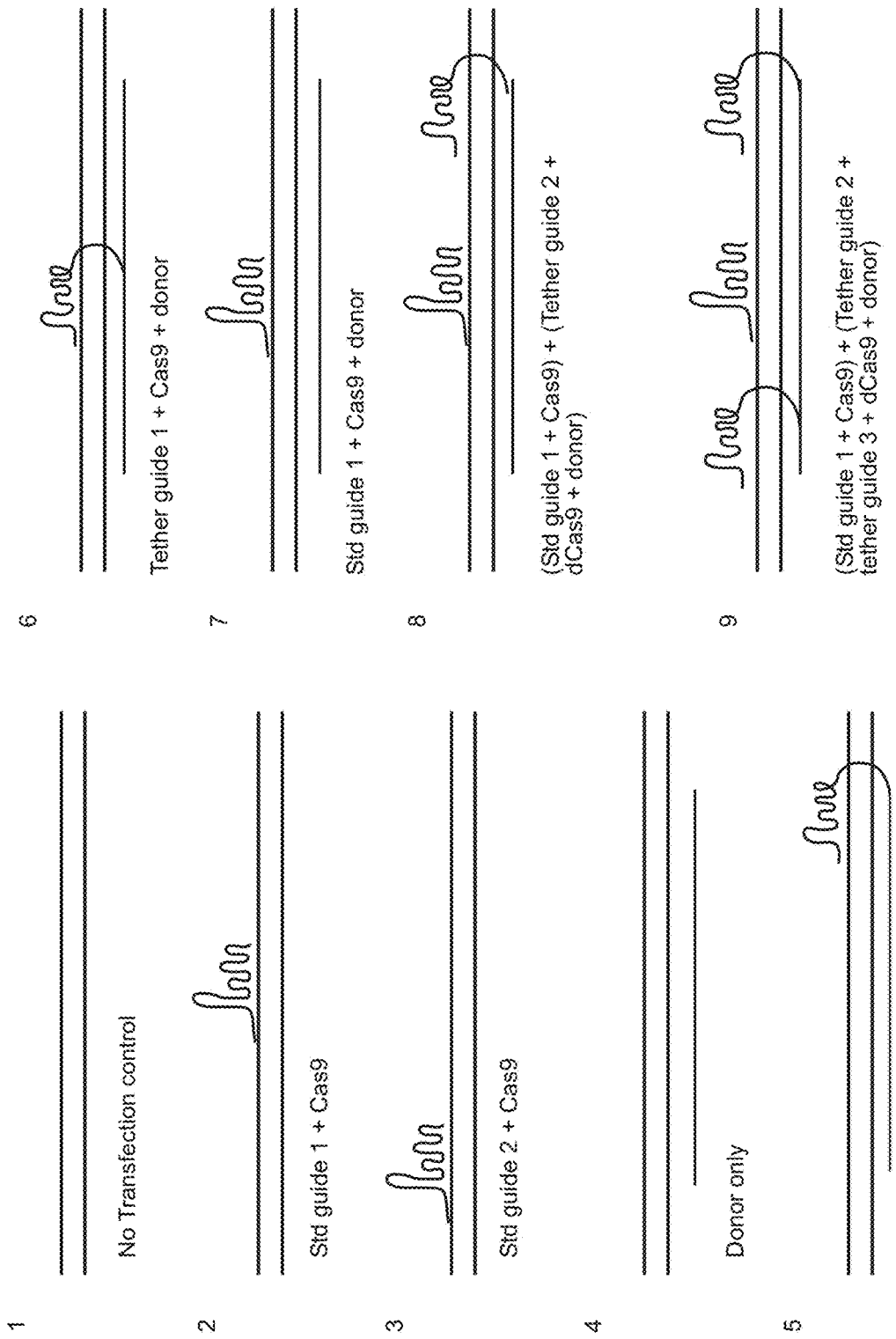
FIG. 10 shows the various embodiments of the experimental conditions used to position homology donor nucleotides near a targeted site for increasing HDR efficiency, as described in Example 5C.

C. Experimental Conditions:

Experimental conditions for the use of various embodiments of the invention are described below and illustrated in FIG. 10.

1) No transfection control—cells are not electroporated.
2) Cas9+ standard sgRNA—cells are transfected with sgRNA and catalytically active Cas9 targeting the locus of interest.
3) Cas9+ standard sgRNA for target locus adjacent site—cells are transfected with sgRNA and catalytically active Cas9 targeting the locus adjacent site to determine if spacer and PAM at that site provide good cleavage activity at that site
4) Donor only control—cells are transfected with the donor polynucleotide to determine if there is incorporation through HDR at the site
5) Tethered sgRNA/dCas9 and donor transfection—cells are transfected with donor polynucleotide and with tethered sgRNA/dCas9 complexes for the site adjacent to the target locus.
6) Tethered sgRNA/Cas9 at the target locus—cells are transfected with catalytically active tethered sgRNA/Cas9 complex with donor polynucleotide to the target locus.
7) Standard sgRNA/Cas9 and donor transfection—cells are transfected with catalytically active sgRNA/Cas9 complex and donor polynucleotide. This will determine the HDR incorporation rates for a standard HDR experiment.
8) Standard sgRNA/Cas9 and tethered sgRNA/dCas9 (one site) and donor transfection—cells are transfected with catalytically active sgRNA/Cas9 complex targeting the target locus and with tethered sgRNA/dCas9 targeting the target adjacent locus and donor polynucleotide.
9) Standard sgRNA/Cas9 and tethered sgRNA/dCas9 (two sites) and donor transfection—cells are transfected with catalytically active sgRNA/Cas9 complex targeting the target locus and with tethered sgRNA/dCas9 targeting upstream and downstream of the target adjacent locus and donor polynucleotide. The two tethers on the two sgRNA/dCas9 complexes stretch the donor polynucleotide across the double-stranded break and make that region available for HDR.

D. Cell Culture and Transfections:

K562 cells (ATCC, Manassas, Va.) are cultured in suspension in IMDM medium supplemented with 10% FBS and 1% penicillin and streptomycin at 37° C. with 100% humidity. K562 cells are transfected using the Nucleofector® 96-well Shuttle System (Lonza, Allendale, N.J.). RNPs and dCas9 RNPs are arranged in a 96-well plate with 2 µl of Cas9 RNP or 4 µl of Cas9 and dCas9 RNP combined. K562 cells are transferred to a 50 ml conical centrifuge tube and centrifuged at 200×G for 3 minutes. The media is aspirated and the cell pellet washed in calcium and magnesium-free PBS. The cells are centrifuged once more and then resuspended in Nucleofector SF buffer (Lonza, Allendale, N.J.) at a concentration of $1\times10^7$ cells/ml. 20 µl of this cell suspension is added to the RNP in the 96 well plate, mixed, and then the entire volume is transferred to a 96-well Nucleocuvette™ Plate (Lonza, Allendale, N.J.). The plate is then loaded into the Nucleofector™ 96-well Shuttle™ (Lonza, Allendale, N.J.) and cells are nucleofected using the 96-FF-120 Nucleofector™ program (Lonza, Allendale, N.J.). Immediately following nucleofection, 80 µl of complete IMDM medium is added to each well of the 96-well Nucleocuvette™ Plate. The entire contents of the well are then transferred to a 96-well tissue culture plate containing 100 µl of complete IMDM medium. The cells are cultured at 37° C. with 100% humidity conditions for 48 hours.

After 48 hours the K562 cells are centrifuged at 500×G for 5 minutes and the medium is removed. The cells are washed 1 time in calcium and magnesium-free PBS. The cell pellets are then resuspended in 50 µl of QuickExtract DNA Extraction solutions (Epicentre, Madison, Wis.). The gDNA samples obtained are then incubated at 37° C. for 10 minutes, 65° C. for 6 minutes and 95° C. for 3 minutes to stop the reaction. gDNA samples are then diluted with 50 µl of water and stored at −20° C.

This gDNA is PCR-amplified using Q5 Hot Start High-Fidelity 2× Master Mix (New England Biolabs, Ipswich, Mass.) at 1× concentration, primers at 0.5 µM each, 3.75 µL of gDNA in a final volume of 10 L and amplified 98° C. for 1 minutes, 35 cycles of 10 s at 98° C., 20 s at 60° C., 30 s at 72° C., and a final extension at 72° C. for 2 min. PCR reaction was diluted 1:100 in water.

A second "barcoding" PCR is set up using unique primers for each sample, facilitating multiplex sequencing. The second PCR is performed using Q5 Hot Start High-Fidelity 2× Master Mix (New England Biolabs, Ipswich, Mass.) at 1× concentration, primers at 0.5 µM each, 1 µL of 1:100 diluted first PCR, in a final volume of 10 µL and amplified 98° C. for 1 minutes, 12 cycles of 10 s at 98° C., 20 s at 60° C., 30 s at 72° C., and a final extension at 72° C. for 2 minutes.

E. SPRIselectclean-Up:

PCR reactions are pooled into a single microfuge tube for SPRIselect™ bead (Beckman Coulter, Pasadena, Calif.) based clean up of amplicons for sequencing.

To pooled amplicons, 0.9× volumes of SPRIselect™ beads are added, and mixed and incubated at room temperature (RT) for 10 minutes. The microfuge tube is placed on a magnetic tube stand (Beckman Coulter, Pasadena, Calif.) until the solution has cleared. Supernatant is removed and discarded, and the residual beads are washed with 1 volume of 85% ethanol, and incubated at RT for 30 s. After incubation, ethanol is aspirated and beads are air dried at RT for 10 min. The microfuge tube is then removed from the magnetic stand and 0.25× volumes of Qiagen EB buffer (Qiagen, Venlo, Netherlands) was added to bead, mixed vigorously, and incubated for 2 minutes at RT. The microfuge tube is returned to the magnet, incubated until solution has cleared and supernatant containing the purified amplicons is dispensed into a clean microfuge tube. The purified amplicon library is quantified using the Nanodrop™ 2000 system (Thermo Fisher Scientific, Wilmington Del.) and library quality analyzed using the Fragment Analyzer™ system (Advanced Analytical Technologies, Inc., Ames, Iowa) and the DNF-910 dsDNA Reagent Kit™ (Advanced Analytical Technologies, Inc. Ames, Iowa).

F. Deep Sequencing Set-Up:

The amplicon library is normalized to 4 nmolar concentration as calculated from Nanodrop values and size of the amplicons. The library is analyzed on MiSeq Sequencer with MiSeq Reagent Kit v2™, 300 Cycles (Illumina, San Diego, Calif.), with two 151-cycle paired-end run plus two eight-cycle index reads.

G. Deep Sequencing Data Analysis:

The identity of products in the sequencing data is analyzed based upon the index barcode sequences adapted onto the amplicons in the second round of PCR. A computational script is used to process the MiSeq data by executing the following tasks:

1. Reads are aligned to the human genome (build GRCh38/38) using Bowtie (bowtie-bio.sourceforge.net/index.shtml) software.
2. Aligned reads are compared to expected wild type target locus sequence. Reads not aligning to any part of the target locus are discarded.
3. Reads matching wild-type target sequence are tallied. Reads with indels are categorized by indel type and tallied.
4. Total indel reads are divided by the sum of wild-type reads and indel reads give percent-mutated reads.

This data is then analyzed to determine if sgRNA/dCas9 tethered donor polynucleotides increase HDR efficiency compared to passively diffused donor polynucleotides.

III. Use of Cas9 Nickase Mutants to Increase the Efficiency of Homology Directed Repair as a Fraction of Total Repair Events Example 6

Use of Tandom Cas9 Nickases to Direct Homology-Directed Repair at Cleavage Sites in Eukaryotic Cells This example illustrates the use of a Cas9 nickase mutant where one nuclease domain is inactivated (Cas9D10A) to engage preferentially homology-directed repair (HDR) pathways and block mutagenic repair pathways at break sites in eukaryotic cells. In this example Cas9D10A is used with two specific, single-guide RNAs (sgRNAs) that deliver the nickase to two sites on the same strand 30-60 nucleotides apart. Spacer sequences were chosen from available sequences in human genomic DNA so that each of the two sgRNAs would target Cas9 to a location on either side of the desired region for modification.

Production of Cas9D10A Nickase and Cas9 Nuclease Components:

sgRNA components of Cas9D10A Ribonucleoprotein (RNP) complexes (also termed "sgRNA/Cas9 nickase complexes" herein) and catalytically active Cas9 nuclease RNP complexes (also termed "sgRNA/Cas9 complexes" herein) were produced by in vitro transcription (e.g., T7 Quick High Yield RNA Synthesis Kit, New England Biolabs, Ipswich, Mass.) from double-stranded DNA templates incorporating a T7 promoter at the 5' end of the DNA sequence. Polymerase Chain Reaction (PCR) using 5 overlapping primers assembled the double-stranded DNA templates for the sgRNA components. The oligonucleotides used in the assembly are presented in Table 6.

TABLE 6

Overlapping Primers for Generating Cas9D10A and Cas9 Nuclease sgRNA Component Templates

| Component | Target for DNA binding | Primers |
|---|---|---|
| Cas9 and Cas9D10A sgRNA | CD34 Target 1 | A, B, C, D, E |
| Cas9 and Cas9D10A sgRNA | CD34 Target 2 | A, B, C, D, F |
| Cas9 and Cas9D10A sgRNA | CD34 Target 3 | A, B, C, D, G |

TABLE 6-continued

Overlapping Primers for Generating Cas9D10A and Cas9 Nuclease sgRNA Component Templates

| Component | Target for DNA binding | Primers |
|---|---|---|
| Cas9 and Cas9D10A sgRNA | CD34 Target 4 | A,B,C,D,H, |
| Cas9 and Cas9D10A sgRNA | CD34 Target 5 | A,B,C,D,I |

A  GTTTTAGAGCTAGAAATAGCAAGTTAAAATAAGGCTAGTCCGTTATCAAC (SEQ ID NO: 3)

B  AAAAAAAGCACCGACTCGGTGCCACTTTTTCAAGTTGATAACGGACTAGC (SEQ ID NO: 4)

C  AAAAAAAGCACCGACTCGGTGCC (SEQ ID NO: 1)

D  AGTAATAATACGACTCACTATAG (SEQ ID NO: 2)

E  TAATACGACTCACTATAGGAACACTGTGCTGATTACAGGTTTTAGAGCTAGAAATAGC
   (SEQ ID NO: 34)

F  TAATACGACTCACTATAGGTTTGTGTTTCCATAAACTGGTTTTAGAGCTAGAAATAGC
   (SEQ ID NO: 35)

G  TAATACGACTCACTATAGGCTACTAACTTGAGCTCCCCGTTTTAGAGCTAGAAATAGC
   (SEQ ID NO: 36)

H  TAATACGACTCACTATAGTCCCAAAGGCGGAGGGCGTTGTTTTAGAGCTAGAAATAGC
   (SEQ ID NO: 37)

I  TAATACGACTCACTATAGAGGCTGGGTTGCCGCCGTCGGTTTTAGAGCTAGAAATAGC
   (SEQ ID NO: 38)

The DNA primers were present at a concentration of 2 nM each. Two outer DNA primers corresponding to the T7 promoter (forward primer: Oligonucleotide A, Table 1), and the 3'end of the RNA sequence (reverse primers: Oligonucleotides C, Table 1) were used at 640 nM to drive the amplification reaction. PCR reactions were performed using Kapa HiFiHotstart PCR™ kit (Kapa Biosystems, Inc., Wilmington, Mass.) as per manufacturer's recommendation. PCR assembly reactions were carried out using the following thermal cycling conditions: 98° C. for 2 minutes, 35 cycles of 15 seconds at 98° C., 15 seconds at 62° C., 15 seconds at 72° C., and a final extension at 72° C. for 2 min. Following the PCR reaction, the quantity of PCR product was determined using capillary electrophoresis on a Fragment Analyzer (Advanced Analytical Technologies, Inc., Ames, Iowa).

Between 0.25-0.5 µg of the DNA template for the sgRNA components were transcribed using T7 High Yield RNA synthesis Kit (New England Biolabs, Ipswich, Mass.) for approximately 16 hours at 37° C. Transcription reactions were DNAse I treated (New England Biolabs, Ipswich, Mass.). The quality of the transcribed RNA was checked by capillary electrophoresis on a Fragment Analyzer (Advanced Analytical Technologies, Inc., Ames, Iowa).

Protein components of RNPs were expressed from bacterial expression vectors in *E. coli*(BL21 (DE3)) and purified using affinity, ion exchange and size exclusion chromatography according to methods described in Jinek, M., et al., "A programmable dual-RNA-guided DNA endonuclease in adaptive bacterial immunity," Science 337 (2012) 816-821. This method for production of Cas9 and/or Cas9D10A/Cas9H840A RNPs can be applied to the production of other Cas9 and/or Cas9D10A/Cas9H840A RNPs as described herein. The coding sequence for *S. pyogenes* Cas9 included the two nuclear localization sequences (NLS) at the C-terminus. Cas9D10A or Cas9H840A nickase variants of NLS-tagged Cas9, where an active site residue of either nuclease domain is mutated (Jinek, et al., 2012) were prepared by introducing mutations into the coding sequence of *S. pyogenes* Cas9 by site directed mutagenesis (e.g. Q5 Site-directed Mutagenesis Kit, New England Biolabs, Ipswich, Mass.).

Example 7

Deep Sequencing Analysis for Detection of Target Modifications in Eukaryotic Cells This example illustrates the use of a MiSeq Sequencer (Illumina, San Diego, Calif.) for deep sequencing analysis to quantify total editing events initiated by DNA cleavage by Cas9 or Cas9D10A and compare DNA repair types. Example DNA repair types can include mutagenic end-joining pathways such as non-homologous end joining (NHEJ) or insertion of material from a donor sequence by homology directed repair (HDR). In this example, Cas9 and Cas9D10A were directed to the human gene CD34 at five independent sites by specific sgRNAs.

A. Transfection of Cas9/Cas9D10A RNPs:

To assemble Cas9 and Cas9D10A RNPs, 1.36 µl of sgRNA (corresponding to approximately 1-5 µg) were incubated for 2 minutes at 95° C. then allowed to equilibrate to room temperature for approximately 5 minutes. Subsequently, Cas9 and Cas9D10A were mixed with a corresponding sgRNA to form RNPs in reaction buffer (20 mM HEPES, pH 7.5, 100 mM KCL, 5 mM MgCl$_2$, 5% glycerol). 20 pmols of Cas9 or Cas9D10A were combined with the target sgRNA and functional RNPs were assembled by incubating at 37° C. for 10 minutes. Finally, 20 pmols of Cas9 or Cas9D10A RNP was combined with 100 pmols of DNA donor oligonucleotide template for HDR prior to transfection into cells. Experiments were performed in triplicate.

TABLE 7

DNA Oligonucleotide Donor Templates

| | |
|---|---|
| CD34 Target 1 | TCAGTTTATGGAAACACAAACTCTTCTGTCCAGTCACAGAgaattcCTGTAATC AGCACAGTGTTCACCACCCCAGCCAACGTTTCAACT (SEQ ID NO: 39) |
| CD34 Target 2 | CCAGAAACGACAGTCAAATTCACATCTACCTCTGTGATAAgaattcCAGTTTAT GGAAACACAAACTCTTCTGTCCAGTCACAGACCTCT (SEQ ID NO: 40) |
| CD34 Target 3 | ACCCAGCCTCCCTCCTAACGCCCTCCGCCTTTGGGACCAAgaattcGGGGAGCT CAAGTTAGTAGCAGCCAAGGAGAGGCGCTGCCTTGC (SEQ ID NO: 41) |
| CD34 Target 4 | CCACCTTTTTTGGCCTCGACGGCGGCAACCCAGCCTCCCTgaattcAACGCCCTC CGCCTTTGGGACCAACCAGGGGAGCTCAAGTTAGT (SEQ ID NO: 42) |
| CD34 Target 5 | CGAGGCATCTGGAGCCCGAACAAACCTCCACCTTTTTTGGgaattcCGACGGCG GCAACCCAGCCTCCCTCCTAACGCCCTCCGCCTTTG (SEQ ID NO: 43) |
| CD34 Targets 1 + 2 Cas9D10A | CACATCTACCTCTGTGATAAgCTCAGTTTATGGAAttCACAAACTCTTCTGTCC AGTCACAGAgCTCTGTAATCAGCACAGTGTTCACCA (SEQ ID NO: 44) |
| CD34 Targets 3 + 4 Cas9D10A | CCTCGACGGCGGCAACCCAGCCTCCCTgCTAACGCCCTCCGaaTTcTGGGACC AAgCAGGGGAGCTCAAGTTAGTAGCAGCCAAGGAGAG (SEQ ID NO: 45) |
| CD34 Targets 4 + 5 Cas9D10A | CCGAACAAACCTCCACCTTTTTTGGCgTCGACGGCGGCAACCgAattCCTCCCT CgTAACGCCCTCCGCCTTTGGGACCAACCAGGGGAG (SEQ ID NO: 46) |
| CD34 Targets 3 + 5 Cas9D10A | CCACCTITTTTGGgCTCGACGGCGGCAACCCAGCCTCCCTCCgAAttCGCCCTC CGCCTTTGGGACCAAgCAGGGGAGCTCAAGTTAGTA (SEQ ID NO: 47) |

Cas9/Cas9D10ARNP complexes were transfected into K562 cells (ATCC, Manassas, Va.), using the Nucleofector® 96-well Shuttle System (Lonza, Allendale, N.J.) and the following protocol: RNP and RNP plus donor complexes were dispensed in a 2-3 µL final volume into individual wells of a 96-well plate. K562 cells suspended in media were transferred from culture. flask to a 50 mL conical, cells were then pelleted by centrifugation for 3 minutes at 200×g, the culture medium aspirated and washed once with calcium and magnesium-free PBS. K562 cells were then pelleted by centrifugation for 3 minutes at 200×g, the PBS aspirated and cell pellet was resuspended in 10 mL of calcium and magnesium-free PBS.

K562 cells were counted using the Countess® II Automated Cell Counter™ (Life Technologies, Grand Island, N.Y.). 2.2×10⁷ cells were transferred to a 50 ml tube and pelleted. The PBS was aspirated and the cells were resuspended in Nucleofector™ SF (Lonza, Allendale, N.J.) solution to a density of 1×10⁷ cells/mL. 20 µL of the cell suspension are then added to individual wells containing 2-3 µL of RNP and RNP plus Donor complexes and the entire volume was transferred to the wells of a 96-well Nucleocuvette™ Plate (Lonza, Allendale, N.J.). The plate was loaded onto the Nucleofector™ 96-well Shuttle™ (Lonza, Allendale, N.J.) and cells were nucleofected using the 96-FF-120 Nucleofector™ program (Lonza, Allendale, N.J.). Post-nucleofection, 80 µL Iscove's Modified Dulbecco's Media (IMDM, Life Technologies, Grand Island, N.Y.), supplemented with 10% FBS (Fisher Scientific, Pittsburgh, Pa.) and supplemented with penicillin and streptomycin (Life Technologies, Grand Island, N.Y.), was added to each well and 50 µL of the cell suspension was transferred to a 96-well cell culture plate containing 150 µL pre-warmed IMDM complete culture medium. The plate was then transferred to a tissue culture incubator and maintained at 37° C. in 5% $CO_2$ for approximately 48 hours.

Genomic DNA (gDNA) was isolated from K562 cells 48 hours after Cas9/Cas9D10A transfection using 50 µL QuickExtract DNA Extraction solution (Epicentre, Madison, Wis.) per well followed by incubation at 37° C. for 10 minutes. 50 µL water was added to the samples, and next they were incubated at 75° C. for 10 minutes and 95° C. for 5 minutes to stop the reaction. gDNA was stored at −80° C. until further processing.

B. Sequencing Library Preparation:

Using previously isolated gDNA, a first PCR was performed using Q5 Hot Start High-Fidelity 2× Master. Mix™ (New England Biolabs, Ipswich, Mass.) at 1× concentration, primers at 0.5 µM each, 3.75 µL of gDNA in a final volume of 10 L and amplified 98° C. for 1 minute, 35 cycles of 10 s at 98° C., 20 s at 60° C., 30 s at 72° C., and a final extension at 72° C. for 2 minutes. PCR reaction was diluted 1:100 in water. Target-specific primers are shown in Table 8.

TABLE 8

Target-specific Primers Used

| | |
|---|---|
| CD34 Target 1_F | GGAGTTCAGACGTGTGCTCTTCCGATCTTGCAAGGCTAGTGCTAGTGG (SEQ ID NO: 48) |

TABLE 8-continued

Target-specific Primers Used

| | |
|---|---|
| CD34 Target 1_R | CACTCTTTCCCTACACGACGCTCTTCCGATCTACATGCACACCCATGTTTTG (SEQ ID NO: 49) |
| CD34 Target 2_F | GGAGTTCAGACGTGTGCTCTTCCGATCTAACATTTCCAGGTGACAGGC (SEQ ID NO: 50) |
| CD34 Target 2_R | CACTCTTTCCCTACACGACGCTCTTCCGATCTACATGCACACCCATGTTTTG (SEQ ID NO: 51) |
| CD34 Target 3_F | GGAGTTCAGACGTGTGCTCTTCCGATCTGTGGGGATTCTTGCTTTTT (SEQ ID NO: 52) |
| CD34 Target 3_R | CACTCTTTCCCTACACGACGCTCTTCCGATCTCTCCAGAAAGCTGAACGAGG (SEQ ID NO: 53) |
| CD34 Target 4_F | GGAGTTCAGACGTGTGCTCTTCCGATCTTTTCCTCTCTTCTCCCCTCC (SEQ ID NO: 54) |
| CD34 Target 4_R | CACTCTTTCCCTACACGACGCTCTTCCGATCTCTGCCACAAAGGGGTTAAAA (SEQ ID NO: 55) |
| CD34 Target 5_F | GGAGTTCAGACGTGTGCTCTTCCGATCTTTTCCTCTCTTCTCCCCTCC (SEQ ID NO: 56) |
| CD34 Target 5_R | CACTCTTTCCCTACACGACGCTCTTCCGATCTCTGCCACAAAGGGGTTAAAA (SEQ ID NO: 57) |
| CD34 Targets 1+2 Cas9D10A_F | GGAGTTCAGACGTGTGCTCTTCCGATCTTGCAAGGCTAGTGCTAGTGG (SEQ ID NO: 58) |
| CD34 Targets 1+2 Cas9D10A_R | CACTCTTTCCCTACACGACGCTCTTCCGATCTCACATGCACACCCATGTTTT (SEQ ID NO: 59) |
| CD34 Targets 3-5 Cas9D10A_F | GGAGTTCAGACGTGTGCTCTTCCGATCTTCTCTTCTCCCCTCCCTTTT (SEQ ID NO: 60) |
| CD34 Targets 3-5 Cas9D10A_R | CACTCTTTCCCTACACGACGCTCTTCCGATCTGCCACAAAGGGGTTAAAAGTT (SEQ ID NO: 61) |

A second 'barcoding' PCR was set up using unique primers for each sample facilitating multiplex sequencing. Primer pairs are shown in Table 9.

TABLE 9

Barcoding Primers

| | |
|---|---|
| ILMN_AMP_FORi5_BC9 | AATGATACGGCGACCACCGAGATCTACACTGAACCTTACACTCTTTCCCTACACGACG (SEQ ID NO: 62) |
| ILMN_AMP_FORi5_BC10 | AATGATACGGCGACCACCGAGATCTACACTGCTAAGTACACTCTTTCCCTACACGAGCG (SEQ ID NO: 63) |
| ILMN_AMP_FORi5_BC11 | AATGATACGGCGACCACCGAGATCTACACTAAGTTCCACACTCTTTCCCTACACGACG (SEQ ID NO: 64) |
| ILMN_AMP_FORi5_BC12 | AATGATACGGCGACCACCGAGATCTACACATAGAGGCACACTCTTTCCCTACACGACG (SEQ ID NO: 65) |
| ILMN_AMP_FORi5_BC13 | AATGATACGGCGACCACCGAGATCTACACGGCTCTGAACACTCTTTCCCTACACGACG (SEQ ID NO: 66) |
| ILMN_AMP_FORi5_BC14 | AATGATACGGCGACCACCGAGATCTACACAGGCGAAGACACTCTTTCCCTACACGACG (SEQ ID NO: 67) |
| ILMN_AMP_FORi5_BC15 | AATGATACGGCGACCACCGAGATCTACACTAATCTTAACACTCTTTCCCTACACGACG (SEQ ID NO: 68) |
| ILMN_AMP_FORi5_BC16 | AATGATACGGCGACCACCGAGATCTACACCAGGACGTACACTCTTTCCCTACACGACG (SEQ ID NO: 69) |
| ILMN_AMP_REVi7_BC49 | CAAGCAGAAGACGGCATACGAGATATACATCGGTGACTGGAGTTCAGACGTGTGCTC (SEQ ID NO: 70) |
| ILMN_AMP_REVi7_BC50 | CAAGCAGAAGACGGCATACGAGATATGCCTTAAGTGACTGGAGTTCAGACGTGTGCTC (SEQ ID NO: 71) |
| ILMN_AMP_REVi7_BC51 | CAAGCAGAAGACGGCATACGAGATATTCAAGTGTGACTGGAGTTCAGACGTGTGCTC (SEQ ID NO: 72) |
| ILMN_AMP_REVi7_BC52 | CAAGCAGAAGACGGCATACGAGATATCTGATCGTGACTGGAGTTCAGACGTGTGCTC (SEQ ID NO: 73) |
| ILMN_AMP_REVi7_BC53 | CAAGCAGAAGACGGCATACGAGATATGTAGCCGTGACTGGAGTTCAGACGTGTGCTC (SEQ ID NO: 74) |

TABLE 9-continued

Barcoding Primers

| | |
|---|---|
| ILMN_AMP_REVi7_BC54 | CAAGCAGAAGACGGCATACGAGATATTTGACTGTGACTGGAGTTCAGACGTGTGCTC (SEQ ID NO: 75) |
| ILMN_AMP_REVi7_BC55 | CAAGCAGAAGACGGCATACGAGATATGGAACTGTGACTGGAGTTCAGACGTGTGCTC (SEQ ID NO: 76) |
| ILMN_AMP_REVi7_BC56 | CAAGCAGAAGACGGCATACGAGATATTGACATGTGACTGGAGTTCAGACGTGTGCTC (SEQ ID NO: 77) |
| ILMN_AMP_REVi7_BC57 | CAAGCAGAAGACGGCATACGAGATATGGACGGGTGACTGGAGTTCAGACGTGTGCTC (SEQ ID NO: 78) |
| ILMN_AMP_REVi7_BC58 | CAAGCAGAAGACGGCATACGAGATATCCACTCGTGACTGGAGTTCAGACGTGTGCTC (SEQ ID NO: 79) |
| ILMN_AMP_REVi7_BC59 | CAAGCAGAAGACGGCATACGAGATATCTTTTGGTGACTGGAGTTCAGACGTGTGCTC (SEQ ID NO: 80) |
| ILMN_AMP_REVi7_BC60 | CAAGCAGAAGACGGCATACGAGATATTGAGTGGTGACTGGAGTTCAGACGTGTGCTC (SEQ ID NO: 81) |

The second PCR was performed using Q5 Hot Start High-Fidelity 2× Master Mix™ (New England Biolabs, Ipswich, Mass.) at 1× concentration, primers at 0.5 µM each, 1 µL of 1:100 diluted first PCR, in a final volume of 10 µL and amplified 98° C. for 1 minute, 12 cycles of 10 s at 98° C., 20 s at 60° C., 30 s at 72° C., and a final extension at 72° C. for 2 minutes. PCR reactions were pooled into a single microfuge tube for SPRIselect™ bead (Beckman Coulter, Pasadena, Calif.) based clean up of amplicons for sequencing.

To pooled amplicons, 0.9× volumes of SPRIselect™ beads were added, mixed and incubated at room temperature (RT) for 10 minutes. The microfuge tube was placed on a magnetic tube stand (Beckman Coulter, Pasadena, Calif.) until the solution had cleared. Supernatant was removed and discarded, and the residual beads were washed with 1 volume of 85% ethanol, and incubated at RT for 30 s. After incubation, ethanol was aspirated and beads were air dried at RT for 10 min. The microfuge tube was then removed from the magnetic stand and 0.25× volumes of water (Qiagen, Venlo, Limburg) was added to the bead, mixed vigorously, and incubated for 2 minutes at RT. The microfuge tube was spun in a microcentrifuge to collect the contents of the tube, and was then returned to the magnet, incubated until the solution had cleared, and the supernatant containing the purified amplicons were dispensed into a clean microfuge tube. The purified amplicon library was quantified using the Nanodrop™ 2000 system (Thermo Scientific, Wilmington Del.).

The amplicon library was normalized to 4 nmolar concentration as calculated from Nanodrop values and size of the amplicons. The library was analyzed on MiSeq Sequencer with MiSeq Reagent Kit v2™, 300 Cycles (Illumina, San Diego), with two 151-cycle paired-end run plus two eight-cycle index reads.

C. Deep Sequencing Data Analysis:

The identity of products in the sequencing data was analyzed based upon the index barcode sequences adapted onto the amplicons in the second round of PCR. A computational script was used to process the MiSeq data by executing the following tasks:

1. Reads were aligned to the human genome (build GRCh38/38) using Bowtie (bowtie-bio.sourceforge.net/index.shtml) software.
2. Aligned reads were compared to wild type loci. Reads not aligning to any part of the loci were discarded.
3. Reads matching wild-type sequence were tallied. Reads with indels (surrounding the Cas9 cut site) were categorized by indel type and tallied.
4. Total indel reads were divided by the sum of wild-type reads and indel reads gave percent-mutated reads.

Indel structures were compared between sequence data that was generated from cells transfected with wild-type Cas9 RNP or Cas9 RNP+Donor, for each of the individual targets, and for Cas9D10A RNP and Cas9D10A RNP+Donor for each of the pairs of targets. The experimental data demonstrated that cells transfected with Cas9 RNP exhibited a number of classes of mutant edits. Cas9 RNP+Donor showed a similar spectrum of mutant edits and donor-dependent edits, whereas cells transfected with Cas9D10A RNP only, showed no evidence of editing but Cas9D10A RNP+Donor demonstrated similar levels of donor insertion to the Cas9 RNP+Donor, but with no measurable mutant edits that could not be attributed to incorporation of the donor sequence.

Figure 12:
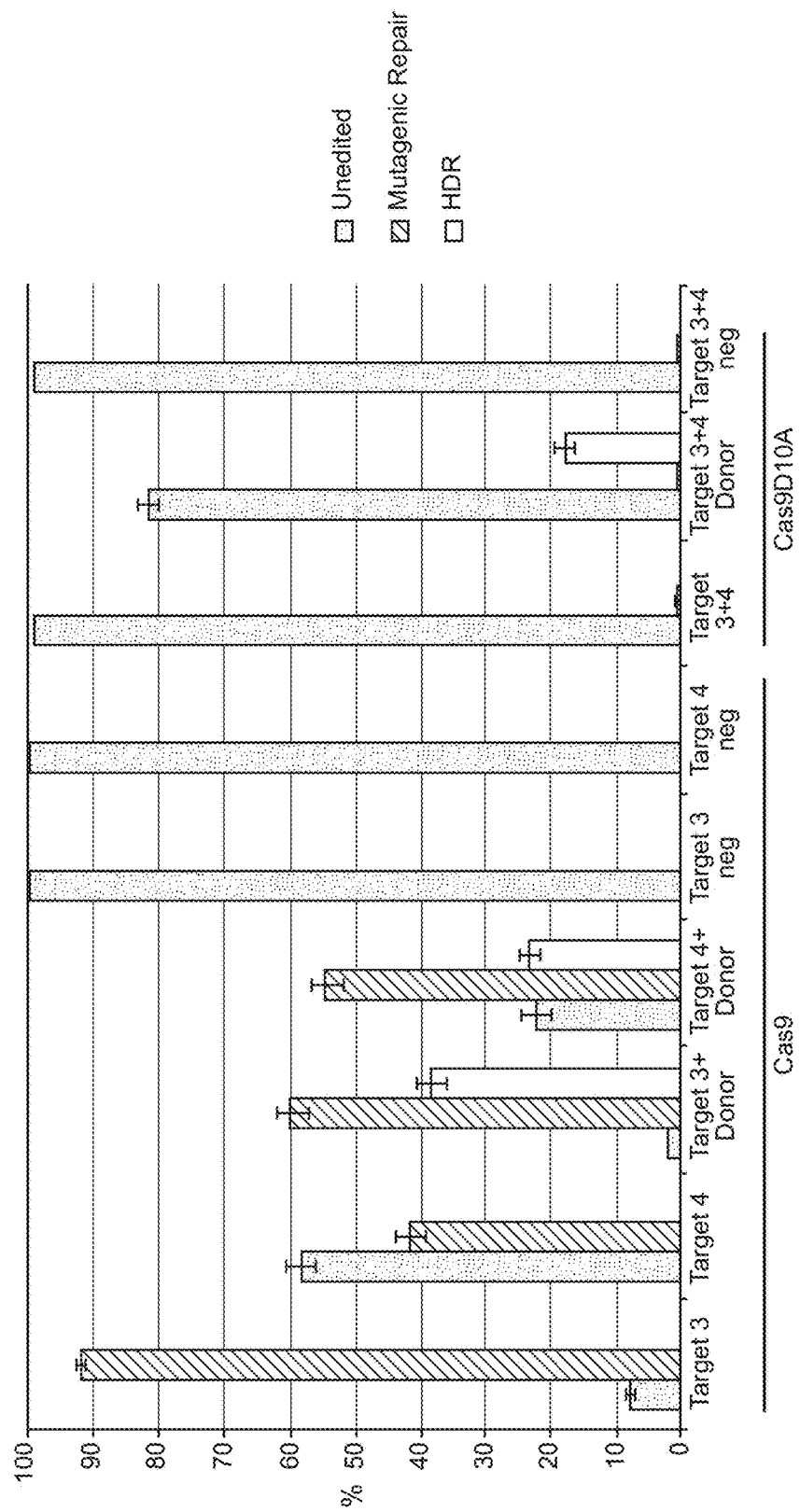
FIG. 12 shows a comparison of repair types using either Cas9 or Cas9D10A at Targets 3 and 4 (human CD34 locus) as described in the examples. Neg denotes a negative control which is either Cas9 or Cas9D10A only, without sgRNA. The distribution of repair is denoted by the bars in the figure. Solid bars=unedited; hatched bars=mutagenic repair; stippled bars=HDR.

FIG. 12 shows a comparison of repair types using either Cas9 or Cas9D10A at Targets 3 and 4 (human CD34 locus). Cas9 RNP complexed with sgRNA was used to target either CD34 Target 3 or CD34 Target 4. Cas9D10A RNPs complexed with sgRNA were used to target CD34 Target 3 and Target 4. Negative controls were Cas9 or Cas9D10A only, without sgRNA. The distribution of repair is shown by the bars. As can be seen, Cas9 RNP displayed only mutagenic repair. Cas9 RNP+Donor demonstrated mutagenic repair and HDR, whereas Cas9D10A RNP showed barely detectable mutagenic repair. Cas9D10A RNP+Donor demonstrated HDR edits with barely detectable mutagenic repair.

Table 10 contains an average of three replicates (excluding negative controls n=2) and standard deviation (STD) of each class.

TABLE 10

Data Used in FIG. 12

| Sample | Nuclease | % Unedited | % Mutagenic Repair | % HDR | Unedited STD | MUT STD | HDR STD |
|---|---|---|---|---|---|---|---|
| Target 3 | Cas9 | 7.7 | 92.3 | 0 | 0.57 | 0.57 | 0 |
| Target 4 | Cas9 | 58.3 | 41.7 | 0 | 2.39 | 2.3 | 0 |
| Target 3 + Donor | Cas9 | 2 | 59.7 | 38.3 | 0 | 2.31 | 2.31 |
| Target 4 + Donor | Cas9 | 22.3 | 54.3 | 23.3 | 2.08 | 2.51 | 1.52 |

TABLE 10-continued

Data Used in FIG. 12

| Sample | Nuclease | % Unedited | % Mutagenic Repair | % HDR | Unedited STD | MUT STD | HDR STD |
|---|---|---|---|---|---|---|---|
| Target 3 neg | Cas9 | 100 | 0 | 0 | ND | ND | ND |
| Target 4 neg | Cas9 | 100 | 0 | 0 | ND | ND | ND |
| Target 3 + 4 | Cas9D10A | 99.3 | 0.7 | 0 | 0.05 | 0.05 | 0 |
| Target 3 + 4 Donor | Cas9D10A | 81.8 | 0.5 | 17.6 | 1.52 | 0 | 1.52 |
| Target 3 + 4 neg | Cas9D10A | 99.4 | 0.6 | 0 | ND | ND | ND |

Following the guidance of the present specification and examples, the deep sequencing analysis described in this example can be practiced by one of ordinary skill in the art with other Cas9/Cas9D10A RNP complexes (i.e. assembled with distinct sgRNAs and distinct ratios of Cas9/Cas9D10A and donor oligonucleotide templates).

Example 8

Use of Paired Cas9D10A or Paired Cas9H840A Tandem Nickases to Enhance the Proportion of HDR-Specific Edits at a Break Site This example illustrates the use of a Cas9 nickase mutant where one nuclease domain will be inactivated (either Cas9D10A or Cas9H840A) to engage preferentially HDR pathways and block mutagenic repair pathways at break sites in eukaryotic cells. In this example, spacer sequences for the two sgRNA sequences are chosen to vary the length of the deletion around the desired target site. Sequences are chosen such that the paired nickases are targeted to two sites on the same strand varying the distance between two sites in a range from 20 to 2000 nucleotides apart. Donor polynucleotides are designed with different lengths and positions relative to the locations of the spacer sequences and tested in combination with each pair of Cas9 nickase sgRNPs. Using the methods described in Examples 6 and 7, experiments are conducted to measure the frequency and type of DNA repair that takes place with each combination of paired nickases. Data are analyzed to identify the combination of nickase sgRNPs and donor polynucleotide that leads to the highest frequency of HDR with the lowest frequency of mutant editing.

Example 9

Figure 11:
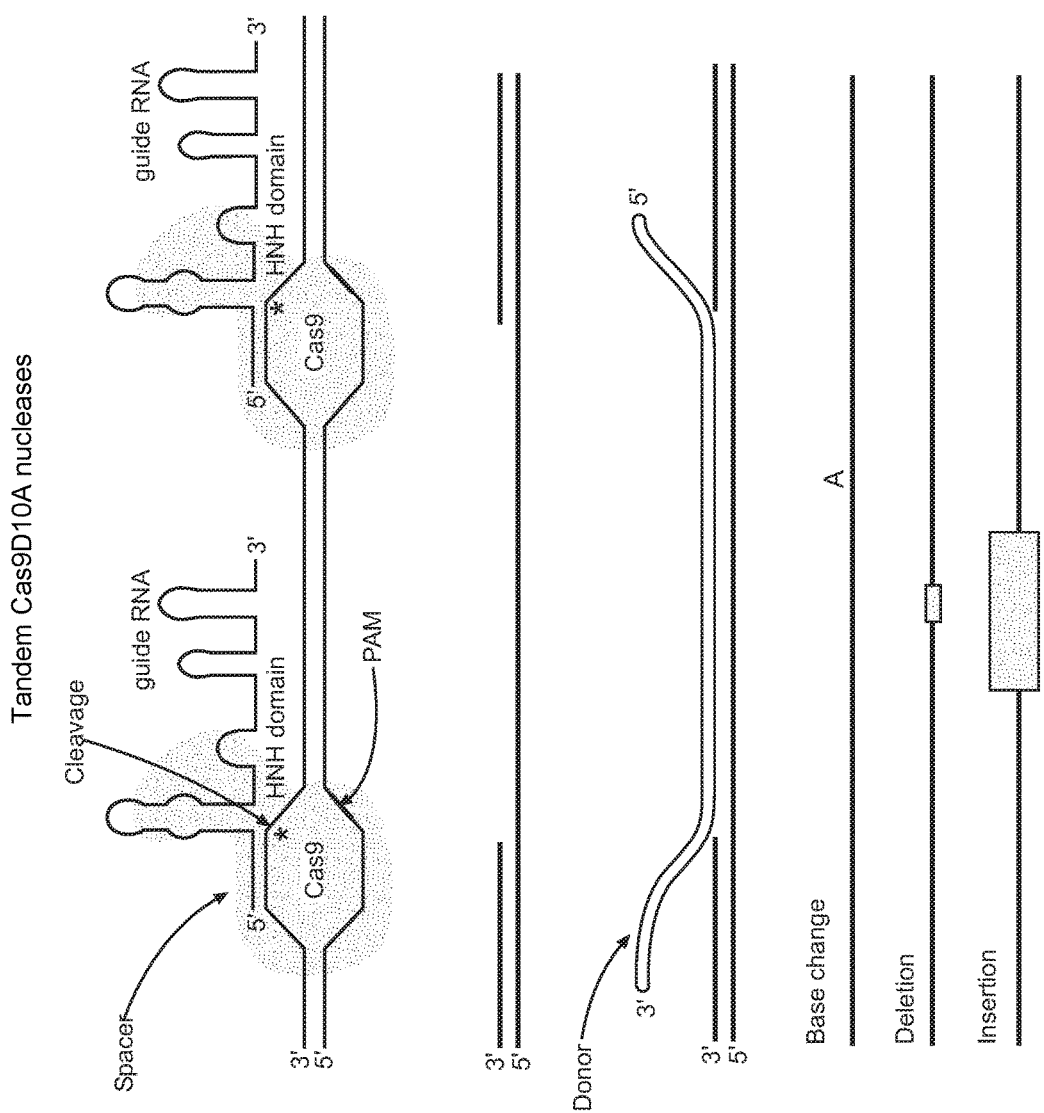
FIG. 11 shows potential donor configurations using tandem Cas9D10A as described in the examples.

Use of Paired Cas9D10A or Paired Cas9H840A Tandem Nickases to Enhance the Proportion of HDR-Specific Edits at a Break Site and Introduce Different, Specific Nucleotide Insertions or Deletions This example illustrates the use of a Cas9 nickase mutant where one nuclease domain will be inactivated (either Cas9D10A or Cas9H840A) to engage preferentially HDR pathways and block mutagenic repair pathways at break sites in eukaryotic cells. In this example, either. paired Cas9D10A or paired Cas9H840A are used with two specific, sgRNAs that deliver the paired nickases to two sites on the same strand 20-2000 nucleotides apart. Donor oligonucleotides are designed to deliver specific nucleotide insertions or deletions at the desired site (FIG. 11). Experiments are carried out varying spacing between nickases and varying donor sequence and length as described in Example 8 to identify the combination of reagents leading to the highest frequency of HDR and lowest frequency of mutagenic repair to introduce the intended modification at the desired site.

Example 10

Use of Paired Cas9D10A or Paired Cas9H840A Tandem Nickases to Enhance the Proportion of HDR-Specific Edits at a Break Site in Human Primary Cells with Various Donor Configurations This example illustrates the use of a Cas9 nickase mutant where one nuclease domain will be inactivated (either Cas9D10A or Cas9H840A) to engage exclusively HDR pathways and block mutagenic repair pathways at break sites in eukaryotic cells. In this example, either paired Cas9D10A or paired Cas9H840A can be used in tandem complexed with two specific sgRNAs that deliver the paired nickases to two sites on the same strand 20-2000 nucleotides apart. The donor oligonucleotides are provided in different orientations and/or lengths to deliver specific nucleotide insertions or deletions between two target Cas9-nickase sites in human primary cells for therapeutic advantage.

Example 11

Use of Paired Cas9D10A and Cas9H840A Tandem Nickases to Enhance the Proportion of HDR-Specific Edits at a Break Site in Human Primary Cells with Various Donor Configurations This example illustrates the use of pairs of Cas9 nickase mutants to engage preferentially homology-directed repair pathways and block mutagenic repair pathways at break sites in eukaryotic cells. In this example, Cas9D10A and Cas9H840A are used in combination with two specific sgRNAs that deliver the paired nickases to two sites resulting in nicking of the same strand 20-2000 nucleotides apart. The sgRNAs paired with Cas9D10A must be chosen to target protospacer sequences and PAM sequences on one strand. The sgRNAs paired with Cas9H840A must be chosen to target protospacer sequences and PAM sequences on the opposite strand to the Cas9D10A sgRNAs to ensure that the same strand is nicked twice. sgRNPs are assembled separately for each nickase mutant by combining the protein with the selected sgRNA. Donor oligonucleotides are designed to deliver specific nucleotide insertions or deletions at the desired site (FIG. 11) and synthesized by an oligonucleotide manufacturer (e.g. Integrated DNA Technologies, Coralville, Iowa). Cas9D10a-sgRNPs are mixed with Cas9H840A-sgRNPs before transfection and the pair of nickases targeting the same strand transfected together with the donor oligonucleotide using methods described in above examples. Experiments are carried out varying spacing between nickases and varying donor sequence and length as described in Example 8 to identify the combination of reagents leading to the highest frequency of HDR and lowest frequency of mutagenic repair to introduce the intended modification at the desired site.

Although preferred embodiments of the subject methods have been described in some detail, it is understood that obvious variations can be made without departing from the spirit and the scope of the methods as defined by the appended claims.

The invention claimed is:

1. A method for reducing binding and/or cleavage of an off-target nucleic acid by a complex comprising a catalytically active Cas9 protein and a guide polynucleotide, said method comprising:

contacting a first complex with a selected target nucleic acid, wherein said first complex comprises: (i) a catalytically active Cas9 protein and (ii) a first guide polynucleotide that comprises a spacer adapted to bind to said selected target nucleic acid; and contacting a second complex with an off-target nucleic acid, wherein said second complex comprises (i) a catalytically inactive Cas9 protein (dCas9 protein) that does not cleave the off-target nucleic acid and (ii) a second guide polynucleotide that comprises a spacer adapted to bind to said off-target nucleic acid, thereby reducing binding and/or cleavage by said first complex of said off-target nucleic acid.

2. The method of claim 1, wherein the guide polynucleotide is a single-guide RNA (sgRNA).

3. The method of claim 1, wherein said catalytically active Cas9 protein is a *Streptococcus pyogenes* Cas9 protein or an orthologous Cas9 protein.

4. The method of claim 1, wherein said dCas9 protein comprises at least one mutation in one or more endonuclease domains to render the dCas9 protein catalytically inactive.

5. The method of claim 4, wherein said dCas9 protein is a *S. pyogenes* Cas9 protein, or an orthologous Cas9 protein with at least one mutation in one or more endonuclease domains to render the orthologous Cas9 protein catalytically inactive.

6. The method of claim 4, wherein said one or more mutations is in a RuvC-1 domain.

7. The method of claim 4, wherein said one or more mutations is in a HNH domain.

8. The method of claim 4, wherein said mutations are in both RuvC-1 and HNH domains.

9. The method of claim 6, wherein said one or more mutations comprises a D10A mutation, numbered relative to *S. pyogenes* Cas9, or the corresponding mutation in an orthologous Cas9 protein.

10. The method of claim 7, wherein said one or more mutations comprises a H840A mutation, numbered relative to *S. pyogenes* Cas9, or the corresponding mutation in an orthologous Cas9 protein.

11. The method of claim 8, wherein said one or more mutations comprises a D10A mutation and a H840A mutation, numbered relative to *S. pyogenes* Cas9, or the corresponding mutations in an orthologous Cas9 protein.

12. The method of claim 1, wherein said selected target nucleic acid is DNA.

13. The method of claim 12, wherein said selected target nucleic acid is double-stranded DNA.

14. The method of claim 1, wherein the selected target nucleic acid is cleaved to provide a cleavage site, and said method further comprises modifying said selected target nucleic acid.

15. The method of claim 14, wherein said modifying comprises inserting at least a portion of a donor polynucleotide at said cleavage site.

16. The method of claim 14, wherein said modifying comprises deleting one or more nucleotides at said cleavage site.

17. The method of claim 1, wherein said method is performed in a cell.

18. The method of claim 17, wherein said cell is a eukaryotic cell.

19. The method of claim 1, wherein said method is performed in vitro.

* * * * *